US 6,767,720 B1

(12) United States Patent
van Roy et al.

(10) Patent No.: US 6,767,720 B1
(45) Date of Patent: Jul. 27, 2004

(54) CDNAS ENCODING CATENIN-BINDING PROTEINS WITH FUNCTION IN SIGNALLING AND/OR GENE REGULATION

(75) Inventors: Frans van Roy, Destelbergen (BE); Ann van Landschoot, Deftinge (BE); Barbara Janssens, Ghent (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 09/574,779

(22) Filed: May 19, 2000

(30) Foreign Application Priority Data

Dec. 23, 1999 (EP) .............................. 99204512

(51) Int. Cl.[7] .................................. C12P 21/02
(52) U.S. Cl. ................. 435/69.1; 435/320.1; 536/23.1; 536/23.5
(58) Field of Search ............................... 536/23.5, 23.1; 435/69.1, 320.1; 530/350

(56) References Cited

U.S. PATENT DOCUMENTS 5,470,966 A    11/1995   Hirano et al.

FOREIGN PATENT DOCUMENTS

WO    WO 98/42296    10/1998

OTHER PUBLICATIONS

Accession No. AI473697, Database EST, NCI–CGAP, Mar. 9, 1999.*
Accession No. AA908795, Database EST, NCI–CGAP, Apr. 13, 1998.*
Accession No. AI148470, Database EST, NCI–CGAP, Oct. 27, 1998.*
Bowie et al (Science, 1990, 247:1306–1310).*
Burgess et al (J of Cell Bio. 111:2129–2138, 1990).*
Lazar et al (Molecular and Cellular Biology, 1988, 8:1247–1252).*
Wang, J. et al. 2000 J. Biol. Chem. 275 (1): 507–513.*
Vanlandschoot et al (Gen/EMBL #AF003924, submitted May 14, 1997).*
Burgess et al. J. of Cell Bio. 111:2129–2138, 1990.*
Lazar et al. Molecular and Cellular Biology 8:1247–1252, 1988.*
Bowie et al, Science, 247:1306–1310, 1990.*
Behrens et al., Functional Interaction of β–catenin with the transcription factor LEF–1; *Nature*, vol. 382, No. 6592, pp. 638–642, Aug. 15, 1996.
Gallet et al., "The C–terminal domain of armadillo binds to hypophosphorylated Teashirt to modulate Wingless singalling in Drosophila", *EMBO Journal*, vol. 18, No. 8, pp. 2208–2217, Apr. 15, 1999.
Partial European Search Report, EP 99 20 1543, dated Oct 18, 1999, 3 pages.

* cited by examiner

*Primary Examiner*—Larry R. Helms
*Assistant Examiner*—Misook Yu
(74) *Attorney, Agent, or Firm*—TraskBritt

(57) ABSTRACT

The invention relates to the field of drug discovery, diagnosis, prognosis and treatment of cancer and neurological disorders. The invention provides among others access to and insight in protein-protein or protein-DNA interactions in a signal transduction or transcriptional pathway controlling cell growth or development throughout a wide range of cells and tissues of the body, and provides means, such as nucleic acid, protein, cells and experimental animals and methods to identify candidate drugs, for example for use in therapy of cancer or neurological disorders. As an example of an alpha-catenin-binding protein with function in intracellular signalling or gene regulation, the invention provides an isolated and/or recombinant nucleic acid or a functional fragment, homologue or derivative thereof, corresponding to a zinc finger gene with a nucleic acid sequence as shown in FIG. 1 and encoding a zinc finger protein, or fragment thereof, capable of complexing with a neurally expressed catenin.

7 Claims, 28 Drawing Sheets

Fig. 1: (Part 1 of 4)

```
  1 CAACGAGTTG.TAGCCGCGGA.GAGCAGGCGT.CGATGCTGGC.GCCCAAAGCC  50

51 TCCAGCCTGA.GAGTCG[████████████████████████████████████] 100

101 [████████████████████████████████████████████████████] 150

151 [████████████████████████████████████████████████████] 200

201 [████████████████████████████████████████████████████] 250

251 [████████████████████████████████████████████████████] 300

301 [████████████████████████████████████████████████████] 350

351 [██████████]AGGCATTTT.TTACTGTCTA.CAGAAACTTA.TTGTAATTCA 400

401 TTTTTCCTCA.CTCCAGTAGT.AAGAATTATA.CCAAAT[TGA]A.AAGAT ATG AA 450
                                          *         M   N

451 TGAGTATCCT.AAAAAAAGAA.AAAGGAAGAC.TCTACACCCT.TCTCGTTATT 500
     E   Y [ P   K   K   R   K   R   K ] T   L   H   P   S   R   Y
              putative NLS
501 CAGATTCCTC.TGGAATAAGC.AGAATTGCAG.ATGGATTCAA.TGGAATTTTC 550
     S   D   S   S   G   I   S   R   I   A   D   G   F   N   G   I   F 551 TCTGATCATT.GTTACAGTGT.CTGTTCTATG.AGACAGCCAG.ATTTAAAATA 600
     S   D   H   C   Y   S   V   C   S   M   R   Q   P   D   L   K   Y 601 TTTTGACAAC.AAAGATGATG.ATTCTGATAC.CGAGACGTCA.AATGACTTGC 650
     F   D   N   K   D   D   D   S   D   T   E   T   S   N   D   L 651 CAAAATTTGC.AGATGGAATC.AAGGCCAGAA.ACAGAAATCA.GAACTACCTG 700
     P   K   F   A   D   G   I   K   A   R   N   R   N   Q   N   Y   L
                                            peptide
701 GTTCCCAGTC.CTGTACTTAG.AATTCTAGAC.CACACTGCCT.TTTCTACAGA 750
     V   P   S   P   V   L   R   I   L   D   H   T   A   F   S   T   E 751 AAAATCTGCT.GATATTGTAA.TTTGTGATGA.AGAGTGTGAC.TCACCTGAAT 800
     K   S   A   D   I   V   I   C   D   E   E   C   D   S   P   E 801 CAGTCAACCA.GCAAACCCAA.GAGGAGAGTC.CTATAGAAGT.TCACACTGCT 850
     S   V   N   Q   Q   T   Q   E   E   S   P   I   E   V   H   T   A
          ◄──── FVR360R
```

Fig.1 (Part 2 of 4)

```
 851 GAAGATGTTC.CAATTGCTGT.AGAAGTGCAT.GCGATTTCTG.AGGATTATGA  900
       E  D  V   P  I  A  V   E  V  H  A   I  S  E  D   Y  D

901 TATAGAGACA.GAAAACAATT.CCTCTGAGAG.TCTCCAAGAC.CAAACTGATG  950
       I  E  T   E  N  N  S   S  E  S  L   Q  D   Q  T  D
                                                        ← FVR359R
 951 AAGAACCGCC.AGCTAAACTT.TGTAAAATTC.TTGACAAGAG.CCAAGCTTTG 1000
       E  E  P   P  A  K  L   C  K  I   D  K   Q  A  L

1001 AATGTGACTG.CCCAGCAGAA.ATGGCCTTTA.CTGAGAGCTA.ATAGCAGTGG 1050
       N  V  T   A  Q  Q  K   W  P  L   R  A  N   S  S  G

1051 CCTCTATAAA.TGTGAACTTT.GTGAGTTTAA.CAGCAAATAT.TTTTCTGACT 1100
       L  Y   K  C  E  L   C  E  F  N   S  K  Y   F  S  D
         ↳ Zinc finger 1
1101 TAAAGCAGCA.TATGATCCTG.AAGCATAAAC.GTACTGATTC.AAATGTGTGT 1150
       L  K  Q  H   M  I  L  K  H   K  R  T  D  S   N  V  C
                  Zinc finger 1 ↵               ↳ Zinc finger 2
1151 CGAGTATGCA.AGGAAAGTTT.CTCTACCAAT.ATGCTTCTGA.TAGAACATGC 1200
       R  V  C   K  E  S  F   S  T  N   M  L  L  I   E  H  A 1201 CAAACTGCAT.GAAGAGGATC.CCTACATTTG.TAAATACTGT.GATTATAAGA 1250
         K  L  H   E  E  D   P  Y  I  C   K  Y  C   D  Y  K
       Zinc finger 2 ↵      ↳ Zinc finger 3
1251 CAGTAATTTT.TGAGAACCTC.AGCCAGCACA.TTGCAGACAC.CCATTTTAGT 1300
       T  V  I  F   E  N  L   S  Q  H  I   A  D  T   H  F  S
                                                 Zinc finger 3 ↵
1301 GATCACCTCT.ATTGGTGTGA.ACAGTGTGAT.GTACAGTTCT.CCTCAAGCAG 1350
       D  H  L   Y  W  C   E  Q  C  D   V  Q  F   S  S  S
              ↳ Zinc finger 4
1351 TGAACTCTAC.CTACATTTCC.AGGAGCACAG.CTGTGATGAA.CAGTACTTGT 1400
       E  L  Y   L  H  F  Q  E  H   S  C  D  E   Q  Y  L
                           Zinc finger 4 ↵      ↳ Zinc finger 5
1401 GTCAGTTCTG.TGAACATGAA.ACTAATGATC.AGAAGACTT.GCATAGCCAT 1450
       C  Q  F   C  E  H  E   T  N  D   P  E  D   L  H  S  H 1451 GTGGTAAATG.AGCATGCATG.TAAATTAATA.GAGTTAAGTG.ATAAGTATAA 1500
       V  V  N  E  H   A  C  K  L  I   E  L  S   D  K  Y  N
                Zinc finger 5 ↵
1501 CAATGGTGAA.CATGGACAAT.ATAGCCTCTT.AAGCAAAATT.ACCTTTGACA 1550
       N  G  E   H  G  Q   Y  S  L  L   S  K  I   T  F  D 1551 AATGTAAAAA.CTTCTTTGTA.TGTCAAGTAT.GTGGTTTTCG.GAGTAGACTT 1600
       K  C  K  N   F  F  V   C  Q  V   C  G  F   R  S  R  L
                      ↳ Zinc finger 6
1601 CACACAAATG.TTAACAGGCA.TGTTGCTATT.GAACATACAA.AAATTTTTCC 1650
       H  T  N   V  N  R  H   V  A  I   E  H  T   K  I  F  P
                                          Zinc finger 6 ↵
1651 TCATGTTTGT.GATGACTGTG.GGAAAGGCTT.TTCAAGTATG.CTAGAATATT 1700
       H  V  C   D  D  C   G  K  G  F   S  S  M   L  E  Y
       ↳ Zinc finger 7
1701 GCAAGCATTT.AAATTCACAT.TTATCTGAAG.GGATTTATTT.ATGTCAATAT 1750
       C  K  H  L   N  S  H   L  S  E  G  I   Y  L   C  Q  Y
                Zinc finger 7 ↵               ↳ Zinc finger 8
```

Fig. 1 (Part 3 of 4)

```
1751 TGTGAATATT.CAACAGGACA.AATTGAAGAT.CTTAAAATTC.ATCTAGATTT 1800
       C  E  Y  S   T  G  Q   I  E  D   L  K  I   H  L  D  F

1801 CAAGCATTCA.GCTGACTTGC.CTCATAAATG.TAGTGACTGC.TTGATGAGGT 1850
       K  H  S   A  D  L  P   H  K  C   S  D  C   L  M  R
Zinc finger 8                Zinc finger 9
1851 TTGGAAATGA.AAGGGAATTA.ATAAGTCACC.TTCCAGTCCA.TGAGACAACT 1900
       F  G  N  E   R  E  L   I  S  H  L   P  V  H   E  T  T
                                              Zinc finger 9

1901 TTATTCT.CTTTAACTTA.CAGAATGTTA.GTTTAAAATA.ATAAATTCAT 1950

1951 CCTTTTTTTG.GAGATGATTA.AATGGATGAT.TGTAAACACA.ACTTATGAAA 2000

2001 TCTGCCTTTA.ACAAGTAACT.TTTTTAAATT.ATAAAATTTT.ATTGGCATTG 2050

2051 CTCCATTTTC.TGTATATAAA.TATATCTTTA.ATGTGGTATT.TTCAATTGCG 2100

2101 TGATAGTTTG.TAGTTTCAAC.CACTCTTGGT.GACTGTCATC.CTGTTTCTTC 2150

2151 CATATTCTCT.GATTTCATGA.ATTGAAAAGA.AACAAATGTA.TTGAAGAAGT 2200

2201 GAGCTACAGT.TTTCCTTCCT.TAACCATGGG.TGCTAGTAAC.TTTTTAAAAC 2250

2251 TCAAGACAAG.ATTAGTTTTT.TATGTGTGAA.GTCATTAAAT.TATTACACGA 2300

2301 CCAGAACTAA.AATGCAATAT.ACAGTTAAGT.CCACGGATAC.TCCCATTAAT 2350

2351 GAGAAATAAC.ACTAGGAAGC.CACTATTACA.GGAAGAAAAG.ATTTGGTTTT 2400

2401 CATGGCAGTC.TGTTTTTTTA.AAAAAAAATT.TTTGAGCCAC.TATCTATTGT 2450

2451 TGAATATTTT.AAGATGGGAT.GAGGGAGGAA.CTAATAAGGG.CTTACACAAT 2500

2501 AAAAAATAAC.TATATCATAA.CTCATTCATA.ACTTGATGTT.TCATTTCTG 2550

2551 TTGAGGAACC.ATAAATTCAT.TCACAGACTT.A                    2600

2601                                                        2650

2651                                                        2700
```

Fig. 1 (Part 4 of 4)

```
2701 ▒▒▒▒▒▒▒▒▒▒▒▒▒▒▒▒▒▒▒▒▒▒▒▒▒▒▒▒▒▒▒▒▒▒▒▒▒▒▒▒ 2750
2751 ▒▒▒▒▒▒▒▒▒▒▒▒▒▒▒▒▒▒▒▒▒▒▒▒▒▒▒▒▒▒▒▒▒▒▒▒▒▒▒▒ 2800
2801 ▒▒▒▒▒▒▒▒▒▒▒▒▒▒▒▒▒▒▒▒▒▒▒▒▒▒▒▒▒▒▒▒▒▒▒▒▒▒▒▒ 2850
2851 ▒▒▒▒▒▒▒▒▒▒▒▒▒▒▒▒▒▒▒▒▒▒▒TGCCCA.AATTTCTGAT.GTCAAATTGT 2900
2901 TCATTGACAG.AAAACCCACT.GAAGTATTTA.AAGTTAGGAA.GATCTGGGAG 2950
2951 ATAGGGGTTG.CTGGCATGAA.AATGTATAAC.TTACAACATT.TATTAATAAA 3000
3000 ATGATAAATT.AGC 3013
```

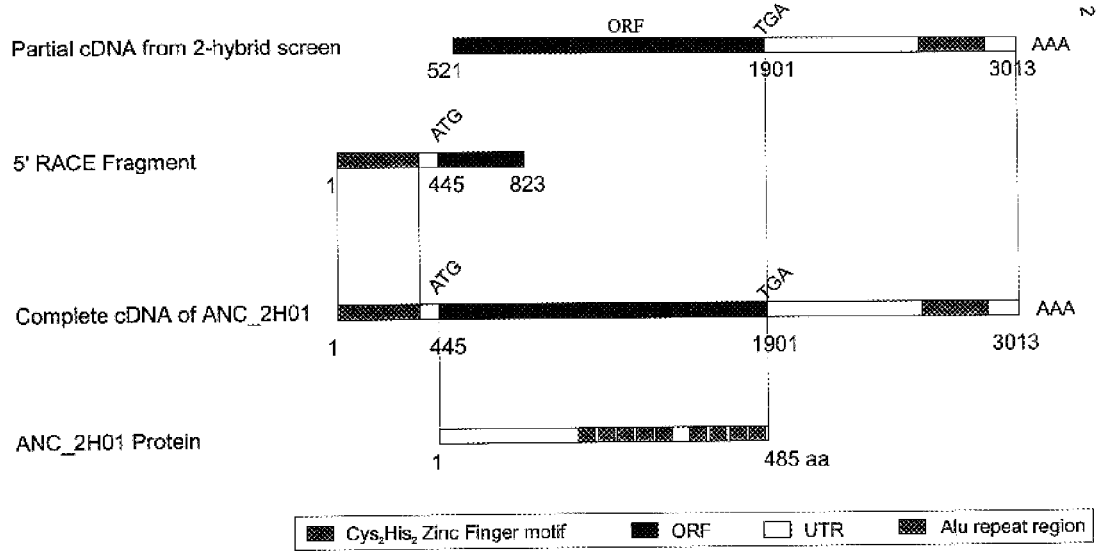

| | | | | | | | | | | | | | | | | | | | | | | | | | |
|---|---|---|---|---|---|---|---|---|---|---|---|---|---|---|---|---|---|---|---|---|---|---|---|---|---|
| 1 | 204 | Y | K | | E | L | | E | F | N | S | K | Y | F | S | D | L | K | Q | | M | I | L | K | | 227 |
| 2 | 233 | N | V | | R | V | | K | E | S | F | S | T | N | M | L | L | I | E | | A | K | L | | | 255 |
| 3 | 259 | Y | I | | K | Y | | D | Y | K | T | V | I | F | E | N | L | S | Q | | I | A | D | T | | 283 |
| 4 | 289 | Y | W | | E | Q | | D | V | Q | F | S | S | S | S | E | L | Y | L | | F | Q | E | | | 311 |
| 5 | 317 | Y | L | | Q | F | | E | H | E | T | N | D | P | E | D | L | H | S | | V | V | N | E | | 340 |
| 6 | 374 | F | V | | Q | V | | G | F | R | S | R | L | H | T | N | V | N | R | | V | A | I | E | | 397 |
| 7 | 403 | H | V | | D | D | | G | K | G | F | S | S | M | L | E | Y | C | K | | L | N | S | | | 425 |
| 8 | 431 | Y | L | | Q | Y | | E | Y | S | T | G | Q | I | E | D | L | K | I | | L | D | F | K | | 454 |
| 9 | 460 | H | K | | S | D | | L | M | R | F | G | N | E | R | E | L | I | S | | L | P | V | | | 482 |

← ANC-2H01 mRNA

Fig. 7
A) HEK293 cells cotransfected with plasmids encoding hBrx-Myc (34 kDa) and hα-catulin-Etag (83 kDa)
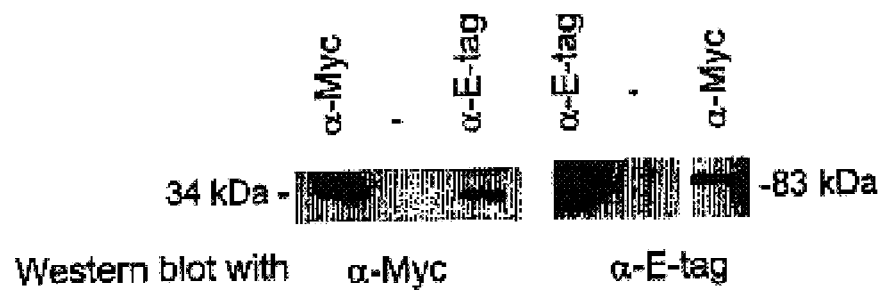
B) HEK293 cells cotransfected with plasmids encoding hBrx-Flag (150 kDa) and hα-catulin-Etag (83 kDa)
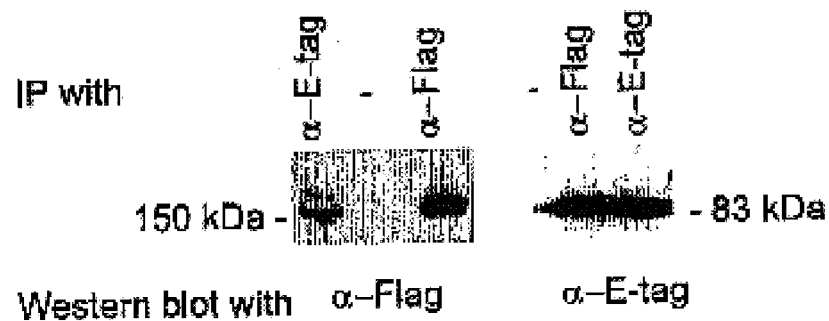

Fig. 10
A
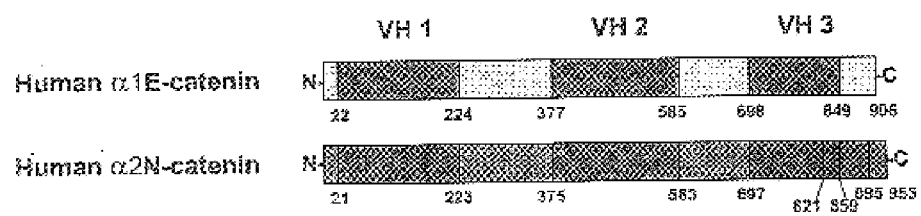
B αE/αN-CHIMERAS
Plasmids:
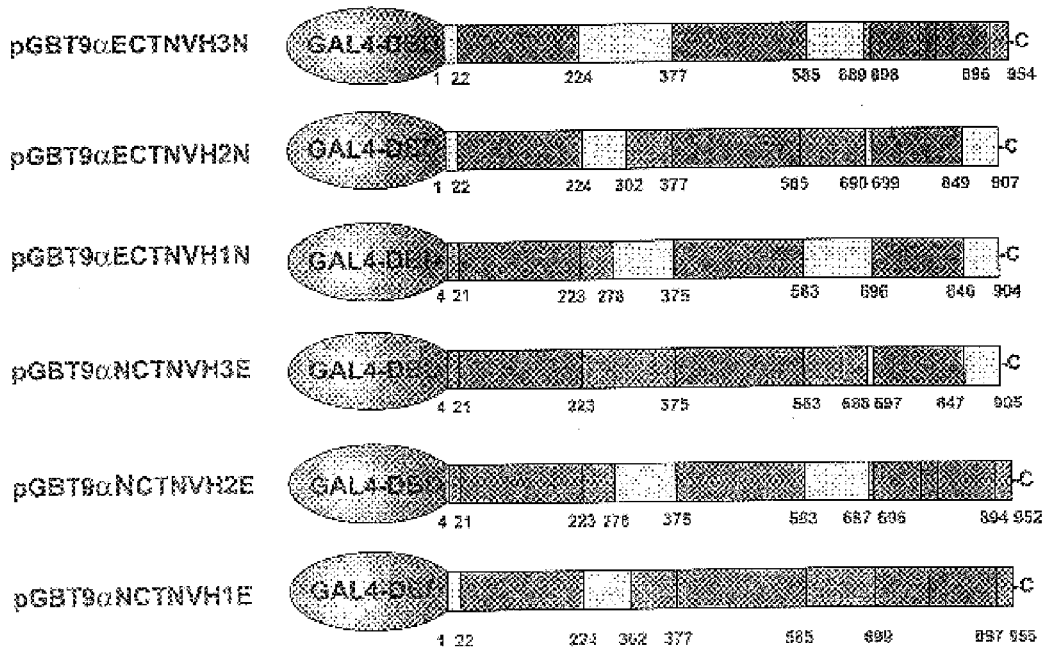

Fig. 11
A
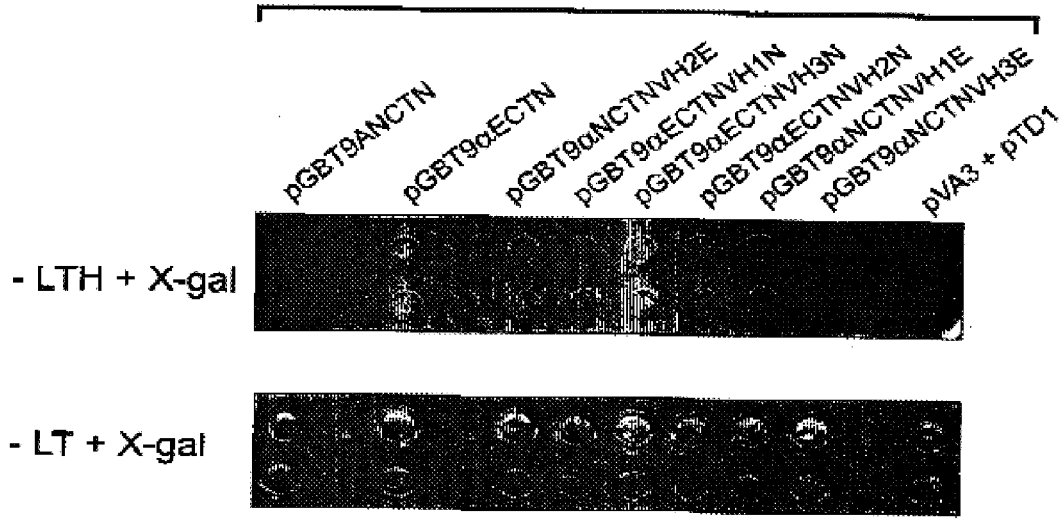
B
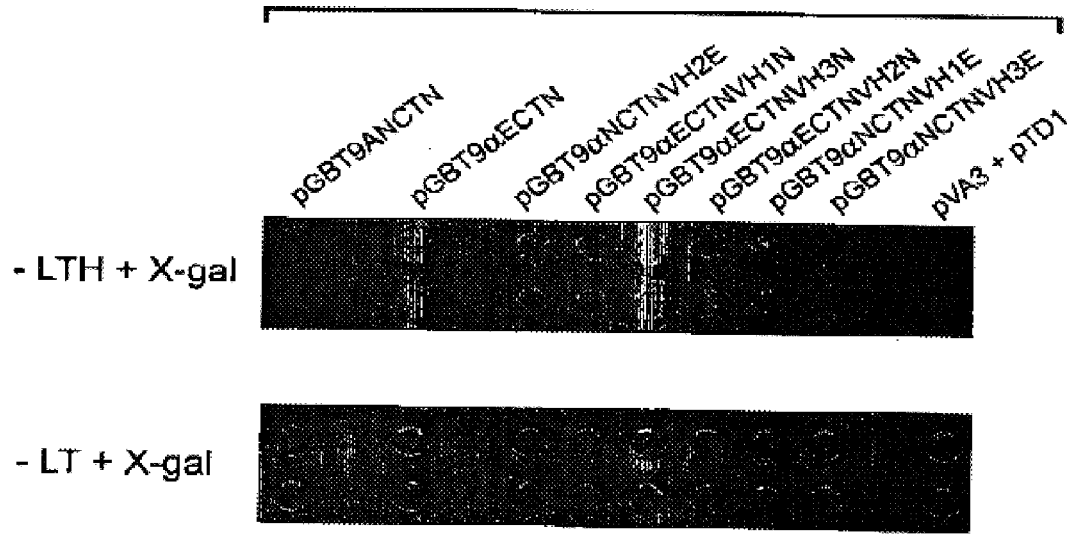

Fig. 18
A
B

Fig. 21 The Brx/proto-Lbc protein

Fig. 26 ttttccgggacatggctgagtgcagcaccccctctcccagaggattgctccccaacacatagccctagagttctcttccgc
tccaacacagaagaggctctcaaaggaggaccttaatgaaaagtgcaataaatgaggtggagatccttcagggtttggt
gagtggaaatctgggaggcacacttgggccgactgtcagcagccccattgagcaagatgtggtcggtcccgttccctgc
cccggagagcagagaccttggaggatttgacagccatcagatgaatgcttcaaaaggaggcgagaaggaagagggagat
gatggccaagatcttaggagaacggaatcagatagtggcctaaaaagagggtggaaatgctaacctggtatttatgcttaa
aagaaacagtgagcaggttgtccagagcgttgttcatctctacgagctcctcagcgctctgcagggtgtggtgctgcagc
aggacagctacattgaggaccagaaactggtgctgagcgagagggcgctcactcgcagcttgtcccgcccgagctccctc
attgagcaggagaagcagcgcagcctggagaagcagcgccaggacctggccaacctgcagaagcagcaggcccagtacc

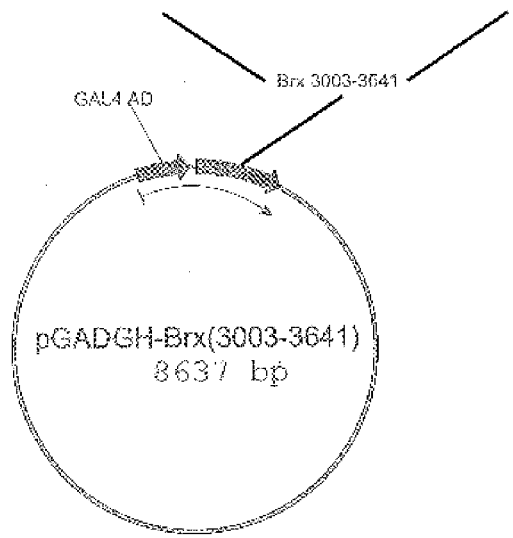

| BAIT | PREY |
|---|---|
| pVA3 | pTD1 |
| pGBT9AECTN | pGADGH-Brx |
| pGBT9ANCTN | pGADGH-Brx |
|  |  |
| pGBT9ACTL | pGADGH-Brx |
| pGBT9 | pGADGH-Brx |
| pVA3 | pGADGH-Brx |
|  |  |
| pGBT9ACTL | pTD1 |

Fig. 28 pLX32H-αct1-E

```
ttccggatctcgatcccggaaattaatacgactcactatagggagaccacaacggtttccctctagaaataattttgtttaactttaagaa
ggagatatacatatgagcgataaaattattcacctgactgacgacagtttttgacacggatgtactcaaagcggacggggcgatcctcgtcg
atttctgggcagagtggtgcggtccgtgcaaaatgatcgccccgattctggatgaaatcgctgacgaatatcagggcaaactgaccgttgc
aaaactgaacatcgatcaaaaccctggcactgcgccgaaatatggcatccgtggtatcccgactctgctgctgttcaaaaacggtgaagtg
gcggcaaccaaagtgggtgcactgtctaaaggtcagttgaaagagttcctcgacgctaacctggccggttctggttctggtgatgacgatg
acaagagcgctgcatctccaggacccgccggcgttggcggcgccggagcagtctacggctccggctcttcgggcttcgccctcgactcggg
actggagatcaaaactcgctcggtggagcagacgctactcccgctggtttctcagatcaccacgcttattaatcataaagataataccaaa
aagtctgataaaactctgcaagcaattcagcgtgtaggacaagctgtcaacttggcagttggaagatttgttaaagtaggagaagctatag
ccaatgaaaactgggatttgaaagaagaaataaatattgcttgtattgaagctaaacaagcaggagaaacaattgcagcacttacagacat
aaccaacttgaaccatctggaatctgatgggcagatcacaattttacagacaaaacaggagtgataaaggctgcaagattacttctttct
tcagtgacaaaagtgttgttgctggcagaccgagtagtcattaaacagataataacatcaagaaataaggttctcgcaactatggaaagac
tagagaaagtgaatagctttcaagagtttgtccaaatattcagtcaatttggaaatgaaatggtggagtttgcacatctgagtggagatag
acaaaatgatttgaaagatgaaaagaaaaaggcaaaaatggcagcagctagggcagttcttgaaaagtgtacaatgatgcttctcacagct
tcaaagacatgtctgaggcatcctaactgcgaatcagcccataaaaacaaagaaggagtatttgaccgtatgaaagtggcattggataagg
tcattgaaattgtgactgactgtaaaccgaatggagagactgacatttcatcctatcagtattttttactggaattaaggaattcaagatgaa
tattgaagctcttcgggagaatctttattttcagtccaaagagaacctttctgtgacattggaagtcatcttggagcgtatggaggacttt
actgattctgcctacaccagccatgagcacagagaacgcatcttggaactgtcaactcaggcgagaatggaactgcagcagttaatttctg
tgtggattcaagctcaaagcaagaaaacaaaaagcatcgctgaagaactggaactcagtattttgaaaatcagtcacagtcttaatgaact
taagaaagaacttcatagtacagcgacacagctggcagcagatctattaaaataccatgctgatcatgtggtttctaaaagcattaaaactt
actggagtagaaggaaattagaagcttttggctgaatatgcctgtaaactctctgaacagaaagagcagcttgttgagacctgtcgattgt
tacgacacatatctgggacagaacctctggaaataacctgtatacatgcagaggagacatttcaggtgactggccaacagataatttctgc
tgctgaaacattgacattgcatccatctagtaaaattgctaaagaaaacctagatgtatttgtgaagcttgggaatcccaaattagtgac
atgtcaacactgctgagagaaatcaatgacgtgtttgaaggaagacgaggagagaagtatggctacctttcacttccaaagccaatgaaga
ataatgcaaacctgaaatcattaaagccagacaagcctgactctgaggagcaagccaagatagcaagcttggacttaagctgggtttgct
cacctctgacgctgactgcgaaattgagaagtgggaagatcaggagaatgagattgttcaatatggacggaacatgtccagtatggcctat
tctctgtatttattactagaggagaggggccactgaaaacttcccaggatttaattcatcaactagaggtttttgctgcagagggtttaa
agcttacttccagtgttcaagctttttcaaaacagctgaaagacgatgacaagcttatgcttctcctggaaataaacaagctaattcctct
atgccaccagctccagacagtaactaagacttctttgcagaataaagtattctcaaaggttgacaagtgtattacgaagacaagatccatg
atggctctcttagtccaacttctttcactttgttataaactgctgagaagcttcagatggaaaataacggatgggtctcagttacaaata
aggacactatggatagtaaaacttccggagcgccggtgccgtatccagatccgctggaaccacgtggcgcctaaggatccgagctcggtac
caagcttatgcatgcggccgcatctagagggcccggatccctcgaggtcgacgaattcgagctcggccgacttggccttcccctttagtgag
ggttaataaacttggtgagcaataactagcataacccctgggcctctaaacgggctcttgagggttttttgctgaaaggaggaactata
tgcgctcatacgatatgaacgttgagactgccgctgagttatcagtgagcaataactagcataaccccttggggcctctaaacgggtcttg
aggggtttttgctgaaaggaggaactatatccggccggatagcttatcgctagaggtcgaaattcacctcgaaagcaagctgataaaccg
atacaattaaaggctccttttggagcctttttttttggagattttcaacgtgaaaaaattattattcgcaattccaagctaattcacctcg
aaagcaagctgataaaccgatacaattaaaggctccttttggagcctttttttttggagattttcaacgtgaaaaaattattattcgcaat
tccaagctctgcctcgcgcgtttcggtgatgacggtgaaaacctctgacacatgcagctccctaggcaattgcatgtgagcaaaaggccag
caaaaggccaggaaccgtaaaaaggccgcgttgctggcgtttttccataggctccgcccccctgacgagcatcacaaaaatcgacgctcaa
gtcagaggtggcgaaacccgacaggactataaagataccaggcgtttccccctggaagctccctcgtgcgctctcctgttccgaccctgcc
gcttaccggatacctgtccgcctttctcccttcgggaagcgtggcgctttctcatagctcacgctgtaggtatctcagttcggtgtaggtc
gttcgctccaagctgggctgtgtgcacgaaccccccgttcagcccgaccgctgcgccttatccggtaactatcgtcttgagtccaacccgg
taagacacgacttatcgccactggcagcagccactggtaacaggattagcagagcgaggtatgtaggcggtgctacagagttcttgaagtg
gtggcctaactacggctacactagaaggacagtatttggtatctgcgctctgctgaagccagttaccttcggaaaaagagttggtagctct
tgatccggcaaacaaaccaccgctggtagcggtggtttttttgttgcaagcagcagattacgcgcagaaaaaaggatctcaagaagatc
ctttgatcttttctacggggtctgacgctcagtggaacgaaaactcacgttaagggattttggtcatgagattatcaaaaaggatcttcac
ctagatccttttaaattaaaaatgaagttttaaatcaatctaaagtatatatgagtaaacttggtctgacagttaccaatgcttaatcagt
gaggcacctatctcagcgatctgtctatttcgttcatccatagttgcctgactccccgtcgtgtagataactacgatacgggagggcttac
catctggccccagtgctgcaatgataccgcgagacccacgctcaccggctccagatttatcagcaataaaccagccagccggaagggccga
gcgcagaagtggtcctgcaactttatccgcctccatccagtctattaattgttgccgggaagctagagtaagtagttcgccagttaatagt
ttgcgcaacgttgttgccattgctgcaggcatcgtggtgtcacgctcgtcgtttggtatggcttcattcagctccggttcccaacgatcaa
ggcgagttacatgatccccccatgttgtgcaaaaaagcggttagctccttcggtcctccgatcgttgtcagaagtaagttggccgcagtgtt
atcactcatggttatggcagcactgcataattctcttactgtcatgccatccgtaagatgcttttctgtgactggtgagtactcaaccaag
tcattctgagaatagtgtatgcggcgaccgagttgctcttgcccggcgtcaacacgggataataccgcgccacatagcagaactttaaaag
tgctcatcattggaaaacgttcttcggggcgaaaactctcaaggatcttaccgctgttgagatccagttcgatgtaacccactcgtgcacc
caactgatcttcagcatcttttactttcaccagcgtttctgggtgagcaaaaacaggaaggcaaaatgccgcaaaaaagggaataagggcg
acacggaaatgttgaatactcatactcttcctttttcaatattatgtaagcagacagttttattgttcatgatgatatatttttatcttgt
gcaatgtaacatcagagattttgagacacaacgtggctttgttgaataaatcgaacttttgctgagttgaaggatcagatcacgcatcttc
ccgacaacgcagaccgttccgtggcaaagcaaaagttcaaaatcaccaactggtccacctacaacaaagctctcatcaaccgtggctccct
cactttctggctggatgatgggggcgattcaggcctggtatgagtcagcaacaccttcttcacgaggcagacctcagcgccggtgatgccgg
ccacgatgcgtccggcgtagaggatctctcacctaccaaacaatgccccctgcaaaaaataaattcatataaaaaacatacagataacca
tctgcggtgataaattatctctggcggtgttgacataaataccactggcggtgatactgagcacatcagcaggacgcactgaccaccatga
aggtgacgctcttaaaattaagccctgaagaagggcagcattcaaagcagaaggctttggggtgtgtgatacgaaacgaagcattggaa
```

Fig. 29A pES31-αct(47-2247)-E

```
gggagtcgctgcgttgccttcgccccgtgccccgctccgcgccgcctcgcgccgcccgccccggctctgactgaccgcgttactcc
cacaggtgagcgggcgggacggcccttctcctccgggctgtaattagcgcttggtttaatgacggctcgtttcttttctgtggctg
cgtgaaagccttaaagggctccgggagggcccttttgtgcggggggagcggctcgggggtgcgtgcgtgtgtgtgcgtgggga
gcgccgcgtgcggcccgcgctgcccggcggctgtgagcgctgcgggcgcggcgcggggcttttgtgcgctccgcgtgtgcgcgaggg
gagcgcggccggggcggtgccccgcggtgcgggggggctgcgaggggaacaaaggctgcgtgcggggtgtgtgcgtggggggtg
agcaggggtgtgggcgcggcggtcgggctgtaacccccccctgcaccccctccccgagttgctgagcacggccggcttcgggt
gcggggctccgtgcgggcgtggcgcggggctcgccgtgccgggcgggggtggcggcaggtgggggtgccgggcggggcgggcc
gcctcgggccggggaggctcggggagggcgcggcggcccggagcgccggcggctgtcgaggcgcggcgagccgcagccattg
cctttatggtaatcgtgcgagagggcgcagggacttcctttgtcccaaatctggcggagccgaaatctgggaggcgccgccgcac
ccctctagcgggcgcgggcgaagcggtgcggcgccggcaggaaggaaatgggcggggagggccttcgtgcgtcgccgccgccg
tccccttctccatctccagcctcggggctgccgcaggggggacggctgccttcgggggggacggggcagggcgggttcggcttctg
gcgtgtgaccggcgggntctaganccctctgctaaccatgttcatgccttcttcttttcctacagctcctgggcaacgtgctggtt
attgtgctgtctcatcattttggcaaagaattcctcgagccaccatggctgcatctccaggacccgccggcgttggcggcgccgga
gcagtctacggctccggctcttcgggcttcgccctcgactcgggactggagatcaaaactcgctcggtggagcagacgctactcc
gctggtttctcagatcaccacgcttattaatcataaagataataccaaaaagtctgataaaactctgcaagcaattcagcgtgtag
gacaagctgtcaacttggcagtttggaagatttgttaaagtaggagaagctatagccaatgaaaactgggatttgaaagaagaaata
aatattgcttgtgtattgaagctaaacaagcaggagaaacaattgcagcacttacagacataaccaacttgaaccatctggaatctga
tgggcagatcacaatttttacagacaaaacaggagtgataaaggctgcaagattacttctttcttcagtgacaaaagtgttgttgc
tggcagaccgagtagtcattaaacagataataacatcaagaaataaggttctcgcaactatggaaagactagagaaagtgaatagc
tttcaagagtttgtccaaatattcagtcaatttggaaatgaaatggtggagtttgcacatctgagtggagatagacaaaatgattt
gaaagatgaaaagaaaaggcaaaaatggcagcagctagggcagttcttgaaaagtgtacaatgatgcttctcacagcttcaaaga
catgtctgaggcatcctaactgcgaatcagcccataaaaacaaagaaggagtatttgaccgtatgaaagtggcattggataaggtc
attgaaattgtgactgactgtaaaccgaattggagagactgacatttcatctatcagtattttttactggaattaaggaattcaagat
gaatattgaagctcttcgggagaatctttattttcagtccaaagagaacctttctgtgacattggaagtcatcttggagcgtatgg
aggactttactgattctgcctacaccagccatgagcacagagaacgcatcttggaactgtcaactcaggcgagaatggaactgcag
cagttaatttctgtgtggattcaagctcaaagcaagaaaacaaaaagcatcgctgaagaactggaactcagtatttgaaaatcag
tcacagtcttaatgaacttaagaagaacttcatagtacagcacacagctggcagcagatctattaaaataccatgctgatcatg
tggttctcaaaagcattaaaacttactggagtagaaggaaatttagaagcttggctgaatatgcctgtaaactctctgaacagaaa
gagcagcttgttgagacctgtcgattgttacgacacatatctgggacagaacctctggaaataacctgtatacatgcagaggagac
atttcaggtgactggccaacagataatttctgctgctgaaacattgacattgcatccatctagtaaaattgctaaagaaaacctag
atgtatttgtgaagcttgggaatcccaaattagtgacatgtcaacactgctgagagaaatcaatgacgtgtttgaaggaagacga
ggagagaagtatggctacctttcacttccaaagccaatgaagaataatgcaaacctgaaatcattaaagccagacaagcctgactc
tgaggagcaagccaagatagcaaagcttggacttaagctgggtttgctcacctctgacgctgactgcgaaattgagaagtgggaag
atcaggagaatgagattgttcaatatggacggaacatgtccagtatggcctattctctgtatttatttactagaggagagggccca
ctgaaaacttcccaggatttaattcatcaactagaggttttttgctgcagagggttttaaagcttacttccagtgttcaagcttttc
aaaacagctgaaagacgatgacaagcttatgcttctcctggaaataaaacaagctaattcctctatgccaccagctccagacagtaa
ctaagacttctttgcagaataaagtatttctaaaggttgacaagtgtattacgaagacaagatccatgatggctctcttagtccaa
cttctttcactttgttataaactgctgaagaagcttcagatggaaaataacggatgggtctcagttacaaataaggacactatgga
tagtaaaacttccggagccgcggtgccgtatccagatccgctggaaccacgtggcgcctaaggatccgagctcggtaccaagctta
agtttaaaccgctgatcagcctcgactgtgccttctagttgccagccatctgttgtttgcccctccccgtgccttccttgaccct
ggaaggtgccactcccactgtcctttcctaataaaatgaggaaattgcatcgcattgtctgagtaggtgtcattctattctggggg
gtggggtggggcaggacagcaagggggaggattgggaagacaatagcaggcatgctggggatgcggtgggctctatggcttctgag
gcggaaagaaccagctgggcttctaggggggtatccccacgcgccctgtagcggcgcattaagcgcggcgggtgtggtggttacgcg
cagcgtgaccgctgccagcgccctagcgcccgctccttcgctttccttccctcgccacgttcgccggctttc
cccgtcaagctctaaatcggggcatccctttagggttccgatttagtgctttacggcacctcgaccccaaaaaacttgattagggt
gatggttcacgtagtgggccatcgcctgatagacggttttttgcccttgacgttggagtccacgttctttaatagtggactctt
gttccaaactggaacaacactcaaccctatctcggtctattcttttgatttataagggatttggggattttcggcctattggttaa
aaaatgagctgatttaacaaaaatttaacgcgaattaattctgtggaatgtgtgtcagttagggtgtggaaagtccccaggctccc
caggcaggcagaagtatgcaaagcatgcatctcaattagtcagcaaccaggtgtggaaagtccccaggctccccagcaggcagaag
tatgcaaagcatgcatctcaattagtcagcaaccatagtccgccccctaactccgcccatcccgcccctaactccgcccagttccg
cccattctccgccccatggctgactaattttttttatttatgcagaggccgaggccgcctctgcctctgagctattccagaagtag
tgaggaggcttttttggaggcctaggcttttgcaaaaagctcccgggagcttgtatatccattttcggatctgatcagcacgtgtt
gacaattaatcatcggcatagtatatcggcatagtataatacgacaaggtgaggaactaaaccatggccaagttgaccagtgccgt
tccggtgctcaccgcgcgcgacgtcgccggagcggtcgagtctggaccgaccggctcgggttctcccgggacttcgtggaggacg
acttcgccggtgtggtccgggacgacgtgaccctgttcatcagcgcggtccaggaccaggtggtgccggacaacaccctggcctgg
gtgtgggtgcgcggccgtggagagctgtacgccgagtggtcggaggtcgtgtccacgaacttccgggacgcctccgggccgccat
gaccggagatcggcgagcagcgtggggcggggagttcgccctgcgcgacccggccggcaactgcgtgcacttcgtggccgaggagc
aggactgacacgtgctacgagatttcgattccaccgccgccttctatgaaaggttgggcttcggaatcgttttccgggacgccggc
tggatgatcctccagcgcggggatctcatgctggagttcttcgcccacccaacttgttattgcagcttataatggttacaaata
aagcaatagcatcacaaatttcacaaataaagcatttttttcactgcattctagttgtggtttgtccaaactcatcaatgtatctt
```

Fig. 29B pES31-αct(47-2247)-E

```
atcatgtctgtataccgtcgacctctagctagagcttggcgtaatcatggtcatagctgtttcctgtgtgaaattgttatccgctc
acaattccacacaacatacgagccggaagcataaagtgtaaagcctggggtgcctaatgagtgagctaactcacattaattgcgtt
gcgctcactgcccgctttccagtcgggaaacctgtcgtgccagctgcattaatgaatcggccaacgcgcggggagaggcggtttgc
gtattgggcgctcttccgcttcctcgctcactgactcgctgcgctcggtcgttcggctgcggcgagcggtatcagctcactcaaag
gcggtaatacggttatccacagaatcagggggataacgcaggaaagaacatgtgagcaaaaggccagcaaaaggccaggaaccgtaa
aaaggccgcgttgctggcgtttttccataggctccgcccccctgacgagcatcacaaaaatcgacgctcaagtcagaggtggcgaa
acccgacaggactataaagataccaggcgtttccccctggaagctccctcgtgcgctctcctgttccgaccctgccgcttaccgga
tacctgtccgcctttctcccttcgggaagcgtggcgctttctcaatgctcacgctgtaggtatctcagttcggtgtaggtcgttcg
ctccaagctgggctgtgtgcacgaaccccccgttcagcccgaccgctgcgccttatccggtaactatcgtcttgagtccaacccgg
taagacacgacttatcgccactggcagcagccactggtaacaggattagcagagcgaggtatgtaggcggtgctacagagttcttg
aagtggtggcctaactacggctacactagaaggacagtatttggtatctgcgctctgctgaagccagttaccttcggaaaaagagt
tggtagctcttgatccggcaaacaaaccaccgctggtagcggtggtttttttgtttgcaagcagcagattacgcgcagaaaaaaag
gatctcaagaagatcctttgatcttttctacggggtctgacgctcagtggaacgaaaactcacgttaagggattttggtcatgaga
ttatcaaaaaggatcttcacctagatcctttttaaattaaaaatgaagttttaaatcaatctaaagtatatatgagtaaacttggtc
tgacagttaccaatgcttaatcagtgaggcacctatctcagcgatctgtctatttcgttcatccatagttgcctgactccccgtcg
tgtagataactacgatacgggagggcttaccatctggccccagtgctgcaatgataccgcgagacccacgctcaccggctccagat
ttatcagcaataaaccagccagccggaagggccgagcgcagaagtggtcctgcaactttatccgcctccatccagtctattaattg
ttgccgggaagctagagtaagtagttcgccagttaatagtttgcgcaacgttgttgccattgctacaggcatcgtggtgtcacgct
cgtcgtttggtatggcttcattcagctccggttcccaacgatcaaggcgagttacatgatccccatgttgtgcaaaaaagcggtt
agctccttcggtcctccgatcgttgtcagaagtaagttggccgcagtgttatcactcatggttatggcagcactgcataattctct
tactgtcatgccatccgtaagatgcttttctgtgactggtgagtactcaaccaagtcattctgagaatagtgtatgcggcgaccga
gttgctcttgcccggcgtcaatacgggataataccgcgccacatagcagaactttaaaagtgctcatcattggaaaacgttcttcg
gggcgaaaactctcaaggatcttaccgctgttgagatccagttcgatgtaacccactcgtgcacccaactgatcttcagcatcttt
tactttcaccagcgtttctgggtgagcaaaaacaggaaggcaaaatgccgcaaaaaagggaataagggcgacacggaaatgttgaa
tactcatactcttccttttcaatattattgaagcatttatcagggttattgtctcatgagcggatacatatttgaatgtatttag
aaaaataaacaaataggggttccgcgcacatttccccgaaaagtgccacctgnnnnnngtcgacattgattattgactagttattaa
tagtaatcaattacgggtcattagttcatagcccatatatggagttccgcgttacataacttacggtaaatggcccgcctggctg
accgcccaacgaccccgcccattgacgtcaataatgacgtatgttcccatagtaacgccaatagggactttccattgacgtcaat
gggtggactatttacggtaaactgcccacttggcagtacatcaagtgtatcatatgccaagtacgccccctattgacgtcaatgac
ggtaaatggcccgcctggcattatgcccagtacatgaccttatgggactttcctacttggcagtacatctacgtattagtcatcgc
tattaccatggnnnnnngtcgaggtgagcccacgttctgcttcactctccccatctcccccccctccccaccccaatttgtatt
tatttattttttaattattttgtgcagcgatggggcgggggggggggcgcgcgccaggcgggcggggcggggcgaggggcg
gggcggggcgaggcggagaggtgcggcggcagccaatcagagcggcgcgctccgaaagttttccttttatggcgaggcggcggcggc
ggcggccctataaaaagcgaagcgcgcggcgggc
```

CDNAS ENCODING CATENIN-BINDING PROTEINS WITH FUNCTION IN SIGNALLING AND/OR GENE REGULATION

CROSS-REFERENCE TO RELATED APPLICATIONS

This application claims priority from pending European Patent Application EP 99204512.0 filed on Dec. 23, 1999, the contents of which are herein incorporated by this reference.

TECHNICAL FIELD

The invention relates to the field of drug discovery, diagnosis and treatment of cancer and neurological disorders. More particularly, the invention relates to a new zinc finger protein binding to a member of the a-catenins/vinculin family and discloses that human a-catulin specifically interacts with Rho-GEF Brx/proto-Lbc.

BACKGROUND

Despite extensive knowledge relating to the multitude of cancer forms (varying in appearance from solid tumours and related metastases in distinct parts of the body to leukaemias of blood cells that circulate throughout the body, and varying from being totally benign to being aggressively malignant), effective treatment of cancer remains difficult and, in general, is restricted to three types of treatments: radiation therapy; chemotherapy; and surgical therapy. Possibilities for a more specific therapy, directed against the underlying cause of a specific cancer, or groups of cancers, are currently virtually non-existant. Extensive efforts are currently being directed at providing such specific therapies through drug discovery processes aimed at identifying candidate drugs for treatment of specific cancers, groups of cancer, or neurological disorders.

Development of cancer often starts with changes in a first cell that lead to the unrestricted development and division of that first cell into an ever dividing population of cells. These changes are often an accumulation of mutations or other alterations in key genes that occur chronologically, whereby the mutated cell population looses its original, often specialised character and acquires more and more of a cancerous nature. The normal processes of growth regulation are generally dysfunctional in the altered cells. Transcription of genes that are normally infrequently expressed in non-cancerous cells may no longer be controlled in cancerous cells.

Activation of transcription of genes by transcription factors that would otherwise be dormant in the specific cell type can, for example, lead to the typical unrestricted growth and neoplastic nature of cancer. Examples are mutations in suppressor genes that function normally by generating proteins that suppress transcriptional pathways which are no longer of use in a specialised cell. Mutated suppressor genes no longer help to keep the growth of a cell under control. Drugs directed against or intervening with the specific protein-protein or protein-DNA interactions in transcriptional and/or signalling pathways controlling cell growth, cell differentiation or development can be considered typical candidate drugs for later use in specific therapies for cancer or neurological disorders, especially when the pathways that such drugs target have gone awry, leading to unrestricted growth or aberrant differentiation of cells. In the case of αN-catenin, which is mainly neurally expressed, a broader or additive interpretation in relationship to neural dysfunctions is obvious.

The cadherin superfamily represents several cadherins which function in cell-cell adhesion, morphogenesis and tissue homeostasis (Takeichi, 1991; Kemler, 1992; Suzuki, 1996). The transmembrane glycoprotein E-cadherin is the best-studied prototype of this family and has been identified as a potent suppressor of invasion (Behrens et al., 1989; Frixen et al., 1991; Vleminckx et al., 1991). Recent studies revealed proof for a tumour suppressor role of human E-cadherin, as the encoding gene behaves according to the two-hit model of Knudson (1985) in infiltrative lobular cancers (Berx et al., 1995 and 1996) and diffuse gastric cancers (Becker et al., 1994 and 1996).

Cadherins function as cell-cell adhesion molecules by homophilic interactions with other cadherin molecules, but linkage to the actin cytoskeleton is also essential. The latter is achieved by the catenins (catena means chain) (Ozawa et al., 1990; Cowin, 1994), which comprise the Armadillo proteins (e.g. β-catenin, plakoglobin and p120$^{ctn}$) and the vinculin-like α-catenins. The Armadillo catenins are proteins, known to be associated with the cytoplasmic domain of cadherins. In turn, the α-catenins link β-catenin and plakoglobin to the actin cytoskeleton.

These catenins were also found to be associated with APC, a cytoplasmic tumour suppressor gene product (adenomatous polyposis coli) (Peifer, 1993; Su et al., 1993). A typical example of a signal transduction pathway (via β-catenin) gone wrong and leading to development of cancer, can be found with APC. The APC protein is linked to the microtubular cytoskeleton. Moreover, in the desmosomes, plakoglobin mediates a link between desmosomal cadherins and the cytokeratin cytoskeleton via desmoplakin (Korman et al., 1989; Kowalczyk et al., 1997).

Two subtypes of α-catenin have been identified, αE-catenin (epithelial form) (Nagafuchi et al., 1991; Herrenknecht et al., 1991) and αN-catenin (neural form) (Hirano et al., 1992). Moreover, for both subtypes two isoforms, resulting from alternative splice events, have been identified (Oda et al., 1993; Uchida et al., 1994; Rimm et al., 1994). A tissue specific distribution for either of the subtypes has been reported. The epithelial αE-catenin is expressed in a wide variety of tissues, but only low levels of expression have been observed in the central nervous system (CNS) (Nagafuchi et al., 1991). In contrast, αN-catenin expression is more restricted to particular tissues including the nervous system, in which it is generally expressed (Hirano et al., 1992; Uchida et al., 1994).

A new homologue of the α-catenins was identified and termed α-catulin (Janssens et al., 1999). The α-catulin cDNA has been found to be expressed in most tissues except in neural tissues. The α-catulin protein shows 25% identity with the alpha-catenins, but provides higher sequence conservation in some putative functional domains.

Recently, key regulators of cadherin-mediated adhesiveness were identifed as proteins of the small-GTPase family. This family consists of the subfamilies Ras and Rho (reviewed in Braga et al., 1999). Ras GTPases are involved in growth control and differentiation. Rho GTPases participate in cytoskeletal reorganisation, activation of kinase cascades, induction of gene transcription and DNA synthesis (reviewed by Mackay and Hall, 1998). The Rho family of GTPases consists of Rho, Rac and CDC42 molecules, showing different specific effects (reviewed in Kaibuchi et al., 1999). Rho is involved in formation of stress fibers and focal adhesions, cell morphology and cell aggregation, including cadherin functionality, cell motility, membrane ruffling, smooth muscle contraction, neurite retraction in neuronal cells and cytokinesis. Rac is involved in membrane ruffling, cell motility, actin polymerization and cadherin-mediated adhesion. Cdc42 participates in filopodia formation.

Inside the cell, these GTPases are normally found associated with GDP and therefore in an inactive state. Activation occurs upon binding to GTP, a process that is tightly regulated by activating GEFs (guanine nucleotide exchange factors) and inactivating GAPs (GTPase activating factors). These transitions between GDP-bound and GTP-bound states are important regulatory processes, as for example constitutively active Rho can induce transformation in tissue culture. Moreover, deletions in Rho-GEFs such as Lbc, Vav and Dbl activate small GTPases (reviewed by Cerione and Zheng, 1996).

For the formation of cadherin-dependent cell-cell contacts, activity of endogenous Rho and Rac is required (Braga et al., 1997). Inhibition of Rho or Rac results in removal of cadherins and other molecules involved in cell-cell adhesion (Takaishi et al., 1997). Interestingly, Rac and some Rac-specific regulatory proteins like Tiam-1 and IQGAP are found to be localized to cell-cell contact sites (Habets et al., 1994; Kuroda et al., 1998). IQGAP is thought to bind to β-catenin in competition with α-catenin (Kuroda et al., 1998). As IQGAP can also bind and crosslink actin filaments, it could thus replace α-catenin in the adhesion complex, but at the same time render the receptors less adhesive.

An example of a signaling molecule from the Rho-GEF family is Brx/proto-Lbc. Brx (Breast cancer nuclear Receptor-binding auXilliary protein) was first identified as a protein able to bind to nuclear hormone receptors, such as the estrogen receptor (ER) (Rubino et al., 1998). It was shown that two C-terminal domains (amino acids 527–950 and 961 to 1429; FIG. 21) of Brx specifically and independently interact with the C-terminal domain of the ER (amino acids 262 to 595), also know as the ligand-binding domain. A 5.3 kb Brx transcript, consistent with the Brx cDNA, is expressed in breast cancer cell lines, normal breast and testis, while larger transcripts of about 9.5 kb are found in human ovary, placenta, heart, lung, skeletal muscle, spleen, pancreas, thymus and peripheral leukocytes. As Brx contains a Dbl-homology (DH) domain and a pleckstrin homology (PH) domain, it was proposed to be a member of the Dbl family of oncoproteins (reviewed in Cerione and Zheng, 1996). As most members of the Dbl family are reported to be exchange factors for RhoA, Brx was proposed to function as a Rho-GEF.

In addition to binding to ER, Brx was shown to bind to other nuclear hormone receptors (NHRs), such as retinoid x-receptor (RXR), peroxisome proliferator-activated receptor (PPAR) and thyroid hormone receptor (THR) (Rubino et al., 1998). After ligand binding, NHRs undergo a conformational change which allows the liganded NHR to bind to DNA and transcription factors, inducing gene activation (reviewed in Beato and Sánchez-Pacheco, 1996). Ligand-mediated activation of NHRs is thought to be regulated by binding of an additional set of proteins. Moreover, NHRs can be activated through signals emanating from the cell surface, such as EGF-induced signaling, suggesting that a second pathway of gene activation by NHR may involve small GTPases. In the presence of estrogen, overexpression of Brx augments reporter activity of an estrogen response element (ERE). Thus Brx, as a Rho-GEF, could be involved in the GTPase pathway to regulate NHR signaling. On the other hand, also the GTPase Cdc42 was shown to be involved in Brx-dependent augmentation of estrogen response (Rubino et al., 1998). Considering that the Brx protein has been found to be highly expressed in hormone-responsive breast epithelium, the expression has also been studied in both normal and neoplastic ovarian tissues, where it was found to be expressed equally (Miller et al., 2000).

By transfecting DNA, derived from lymphoid blast crisis tissue, into NIH3T3 cells, an oncogene called Lymphoid Blast Crisis or Lbc was cloned and found to confer tumorigenicity in nude mice (Toksoz and Williams, 1994). Lbc contains a DH and a PH domain (FIG. 21). Recently, it was shown that the onco-Lbc transcript is a chimera derived from rearrangement between chromosome 15 and chromosome 7 (Sterpetti et al., 1999). From the 3' 242 bp derived from chromosome 7 (bp 2863 to 3106 in FIG. 22), only the first 30 bp are coding sequence. On the non-rearranged chromosome 15, a proto-Lbc gene is present, encoding a protein with a C-terminal domain of 478 amino acid residues that are missing in the onco-Lbc product. The protein sequence of proto-Lbc is largely identical to this of Brx (FIG. 22). The proto-Lbc transcript is found in a wide variety of tissues (Toksoz and Williams, 1994; Sterpetti et al., 1999). It shows high expression in spleen and testis, and lower levels in prostate, ovary, hematopoietic cells, skeletal muscle, lung, heart and small intestine. The cell lines HeLa, MOLT4, Raji, A549, G361, HL60 and SW480 are also positive for proto-Lbc. Transcript lengths vary between 5 and 9 kb, and alternative splicing at the 5' end was repeatedly detected.

Both proto- and onco-Lbc are able to promote the formation of GTP-bound RhoA, although the onco-Lbc seemed to be slightly more efficient. After transfection into NIH 3T3 cells, proto-Lbc was only weakly transforming, whereas the activity of onco-Lbc was about 15 times higher (Sterpetti et al., 1999). Deletion of the a-helical and proline-rich regions (see FIG. 21) conferred 5 times higher transforming activity to proto-Lbc, but the DH and PH domains turned out to be absolutely necessary for transformation. This suggests that the proto-Lbc-specific C-terminal domain is important in negative regulation of both oncogenic and Rho-GEF activity. The onco-Lbc protein was recently found to be responsible for Rho-induced cell-rounding after thrombin stimulation of astrocytoma cells, thus providing for the first time a link between G protein-coupled receptors and Rho-mediated cytoskeletal response (Majumdar et al., 1999). Proto-Lbc also shows this effect, albeit at lower levels. The DH domain, but not the PH domain, is necessary to obtain this effect. This confirms that the DH domain confers Rho-GEF activity. The latter activity has been demonstrated for both onco-Lbc and proto-Lbc proteins (Sterpetti et al., 1999). The PH domain is probably important for subcellular localization of the protein. Moreover, Sterpetti et al. (1999) reported that the proto-Lbc protein associates with a particulate intracellular fraction, whereas onco-Lbc is completely cytosolic. A summary of functional domains in the Brx/proto-Lbc protein is given in FIG. 21. The ER binds to a central as well as to the C-terminal region. The a-helical region could be implicated in dimerisation or protein-protein association, as a homologous region is found in caldesmon, myosin, plectin and trichohyalin. The Pro-rich sequence is a potential SH3-binding site. The invention provides evidence that α-catulin is binding to the C-terminal activity-regulating domain of Brx/proto-Lbc.

One of the most intriguing discoveries in the field of cadherins and catenins is the recently described association of LEF-1 (lymphocyte enhancer-binding factor-1), an architectural transcription factor (Love et al., 1995), with β-catenin (Behrens et al., 1996). The interaction between β-catenin and LEF-1 leads to nuclear translocation of these two proteins, implicating a central role for β-catenin in the transcriptional regulation of target genes, which can lead to tumorigeneity (Huber et al., 1996; Peifer, 1997). Among the target genes induced by the β-catenin/LEF-1 complex are the myc proto-oncogene (He et al., 1998) and the cyclin D1 gene (Tetsu and McCormick, 1999).

Cadherin-catenin-cytoskeleton complexes are key elements of cell-cell adhesion and regulation of motility, the importance of nuclear signalling by catenins is gaining interest and may be critical in tumorigeneity, invasion and metastasis. However, despite the existing knowledge regarding cadherins and catenins, it was not previously known what proteins are capable of translocating catenins to the nucleus, or how catenins might exert their effect on intracellular signalling and on the transcription of genes in the cell. With the means and methods of the current invention a key step has become apparent. Moreover, through the identification of such a step in the translocation of catenins to the nucleus, it has now become possible to develop means and methods for interfering with said process in, for instance, tumorigeneity, invasion and metastasis of cells.

SUMMARY OF THE INVENTION

The invention provides access to and insight into protein-protein or protein-DNA interactions in a transcriptional pathway controlling cell growth or development throughout a wide range of cells and tissues of the body. The invention further provides means, such as nucleic acids, proteins, cells, experimental animals, and methods to identify candidate drugs, for example, for use in therapy of cancer and/or neurological disorders.

In the context of this application, "nucleic acid" is used to mean both RNA and DNA, in single or double-stranded fashion, as well as nucleic acid hybridising thereto is meant.

As it is used in the context of this application, "Homologue" means a related nucleic acid that can be found in another species.

As it is used in the context of this application, the term "Derivative" means a nucleic acid that has been derived by genetic modifications, such as deletions, insertions, and mutations from a distinct nucleic acid or fragment thereof.

As it is used in the context of this application, "Corresponding" means having a nucleic acid sequence homology of at least 80%, more preferably of at least 90%. The sequence similarities, obtained by the BLAST algorithm (Altschul et al., 1990) are given by P-scores (the more negative, the higher the similarity), not by percentages. Nevertheless, nucleotide sequence homology can be expressed as percentages (numbers of identical nucleotides per 100 nucleotides).

The terms "α-catenin/vinculin family" relate to a family of proteins comprising vinculin, α-catulin (VR15) and α-catenins such as αE-catenin and αN-catenin. In this regard it should be clear that "functional homologues of α-catenin" comprise other members of the α-catenin/vinculin family that are not 100% identical to vinculin, α-catulin, αE-catenin or αN-catenin, but are homologous to vinculin, α-catulin, αE-catenin or αN-catenin and can be denominated as "vinculin like" or "α-catulin-like" or "'α-catenin-like".

The invention also provides an isolated and/or recombinant nucleic acid or a functional fragment, homologue or derivative thereof, corresponding to a catenin-binding protein with function in signal transduction or gene regulatory pathways, more specifically to an isolated and/or recombinant nucleic acid or a functional fragment, homologue or derivative thereof, corresponding to, for example, a gene encoding a GTPase Exchange Factor (GEF) for Rho family members, and with nucleic acid sequence as shown in FIG. 26 (SEQ. I.D. NO. 132), being part of the Brx/proto-Lbc sequences and encoding a Rho-GEF protein or fragment thereof, said protein capable of complexing or interacting with catenin or fragments thereof.

The invention provides an isolated and/or recombinant nucleic acid or a functional fragment, homologue or derivative thereof, corresponding to a catenin-binding protein with function in signal transduction or gene regulatory pathways more specifically to an isolated and/or recombinant nucleic acid or a functional fragment, homologue or derivative thereof, corresponding to, for example, a zinc finger gene with a nucleic acid sequence as shown in FIG. 1 (SEQ. I.D. NO. 1) and encoding a zinc finger protein, or fragment thereof, said protein capable of complexing or interacting with catenin or fragments thereof.

As used in the context of this application "Functional fragment" means a nucleic acid or part thereof that is functionally or structurally related to or hybridising with a distinct nucleic acid or fragment thereof. Typical examples of such a functional fragment as provided by the invention are DNA binding elements and/or subcellular localisation signals.

For example, further characterisation of nucleic acid according to the invention revealed the presence of nucleic acid encoding protein fragments encoding $Cys_2His_2$ zinc fingers with DNA binding properties. In addition, in yet another functional fragment, a nuclear localisation signal (NLS, such as PKKRKRK) (SEQ ID NO: 151) has been found.

The invention also provides a nucleic acid according to the invention wherein said protein is capable of nuclear translocation of αN-catenin but not αE-catenin. Co-expression of a zinc finger protein as provided by the invention or a functional fragment thereof with particular catenins, such as αN-catenin, leads to a translocation of this catenin into the nucleus. A zinc finger protein as provided by the invention protein can, for example, be isolated in a two-hybrid screening, using human αN-catenin or another catenin as a bait, and is herein also called a catenin-binding protein.

BRIEF DESCRIPTION OF THE DRAWINGS

FIG. 1. Sequence of the full-size human ANC_2H01 cDNA (SEQ ID NO: 1). Dots separate blocks of 10 nucleotides. Sequences of primers used in the 5' RACE experiment are indicated by named arrows. The predicted amino acid sequence of the ORF is indicated in bold (one-letter code). The start codon is boxed in and is preceded by an in-frame stop codon (shaded box). The Alu repeat regions in the 5'UTR and the 3'UTR are shaded and boxed in. Also indicated are the nine zinc finger motifs (SEQ. I.D. NO.s 3–11). The amino acid sequence of the peptide used to raise polyclonal antibodies is underlined (SEQ. I.D. NO. 2). The sequence of the putative NLS is also boxed in.

FIG. 2. Cloning of the full-size cDNA encoding the ANC_2H01 protein. ORF=Open Reading Frame; UTR= Untranslated region; ATG=start codon; TGA=stop codon; AAA=poly A tail; aa=amino acid residues FIG. 3. Alignment of the nine zinc finger motifs (ZF 1–9) of the ANC_2H01 protein (SEQ ID NOS: 3–11), respectively. Numbers indicate the number of the codon. The amino acids are in the one-letter code.

FIG. 5. Northern blot analysis of ANC_2H01 mRNA in three human tumor cell lines. 28S and 18S are ribosomal size markers.

FIG. 6. The expression of ANC_2H01 mRNA in various human tissues was studied by use of a human RNA master blot (Clontech). Hybridization was as described in Materials and Methods.

FIG. 7. Co-immunoprecipitation of Brx with α-catulin. (A) HEK293 cells were transiently co-transfected with constructs pES31-αctl(47-2247)-E and pCS2MT-Brx(3003-3641), encoding the hα-catulin-Etag (83 kDa) and hBrx-Myc (34 kDa) fusion proteins, respectively. After immunoprecipitation (IP) with anti-Myc-tag and anti-E-tag antibodies as indicated, the precipitates were subjected to SDS-PAGE followed by Western blotting with the same antibodies, as indicated. After IP of the E-tagged α-catulin, the Myc-tagged Brx can be detected and vice-versa, thus proving the interaction between these proteins. (B) HEK293 cells were transiently transfected with constructs pES31-αctl(47-2247)-E and pBK-RSV-Brx (142-4290), encoding the hα-catulin-Etag (83 kDa) and hBrx-Flag (150 kDa) fusion proteins, respectively. After IP with anti-Flag-tag and anti-E-tag antibodies as indicated, the precipitates were subjected to SDS-PAGE followed by Western blotting with the same antibodies, as indicated. After IP of the E-tagged α-catulin, the Flag-tagged Brx can be detected and vice-versa, thus proving the interaction between these proteins. As a negative control, only protein-G-Sepharose beads without addition of primary antibodies were used to treat the lysates (shown as '−'). In that case, none of the proteins were precipitated.

FIG. 10. (A) Schematic representation of the vinculin homology domains (VH) in the α1E-catenin and the α2N-catenin protein. α2 isoforms differ from the α1 isoforms by an alternatively used exon nearby the carboxyterminus (black box). (B) Schematic representation of the coding potential of the αE/αN-chimeric cDNAs inserted into the pGBT9 two-hybrid vector. GAL4-DBD=GAL4 DNA-binding domain FIG. 11. *The Saccharomyces cerevisiae* strain Y190 was cotransformed with: (A) plasmid pGAD424ANC2H01-FL encoding full-length ANC_2H01 fused to the GAL4-AD, in combination with a plasmid encoding αN-catenin, αE-catenin or αE/αN-catenin chimeras fused to the GAL4-DBD (FIG. 10), and (B) the initial two-hybrid clone pGAD10ANC2H01 encoding part of ANC_2H01 fused to the GAL4-AD, in combination with plasmids encoding αN-catenin, αE-catenin or αE/αN-catenin chimeras fused to the GAL4-DBD (FIG. 10). The plates contained the medium composition indicated at the left completed with 40 mM 3-AT and 80 mg/ml X-gal. GAL4-AD=GAL4 transcription activation domain; GAL4-DBD=GAL4 DNA-binding domain; −LT=SD medium lacking Leu and Trp; −LTH=SD medium lacking Leu, Trp and His. pVA3 and pTD1 are plasmids used as a positive control in the two-hybrid system (Matchmaker™, Clontech).

FIG. 18. Amino acid alignment of human αN- and αE-catenin from position 120 to 300 (A) (SEQ ID NOS: 135 and 136) and from position 359 to 598 (B) (SEQ ID NOS; 137 and 138). Amino acid residues shaded in black are identical between αN- and αE-catenin; amino acid residues shaded in gray are not identical but structurally or functionally interchangeable between αN- and αE-catenin; amino acid residues in white are neither identical nor interchangeable between αN- and αE-catenin. Arrows indicate amino acid positions corresponding to the restriction sites used to construct the αE/αN-catenin chimeras. Regions of αN-catenin that are necessary for the specific interaction with ANC_2H01 are between the SstII and the NdeI restriction sites (respectively corresponding to amino acid positions 134 and 279) and between the NruI and PstI restriction sites (respectively corresponding to amino acid positions 374 and 549).

FIG. 21. Alignment of Brx, proto-Lbc and onco-Lbc cDNA sequences (GenBank Accession numbers AF126008, AF127481 and U03634), with the obtained two-hybrid clone ACTL2H_K_E2. Lines indicate cDNA sequence, boxes represent open reading frames. All sequences are identical to the consensus Brx/proto-Lbc sequence represented at the top, except for bp 889 to 950 in Proto-Lbc, bp 1396 to 1587 and bp 2864 to 3106 in Onco-Lbc. Positions are indicated in nucleotides.

FIG. 26. The isolated prey plasmid: pGADGH-Brx(3003-3641), with the sequence of the Brx-specific 638-bp insert (SEQ ID NO: 132) shown.

FIG. 28. Sequence of the pLX32H-αct1-E clone (SEQ ID NO: 133), constructed by Dr. Nico Mertens (Department of Molecular Biology, VIB).

FIG. 29. Sequence of the pES31-αct1(47-2247)-E clone (SEQ ID NO: 134). The pES31 vector was constructed by Dr. Nico Mertens (Department of Molecular Biology, VIB).

DETAILED DESCRIPTION OF THE INVENTION

Figure 4:
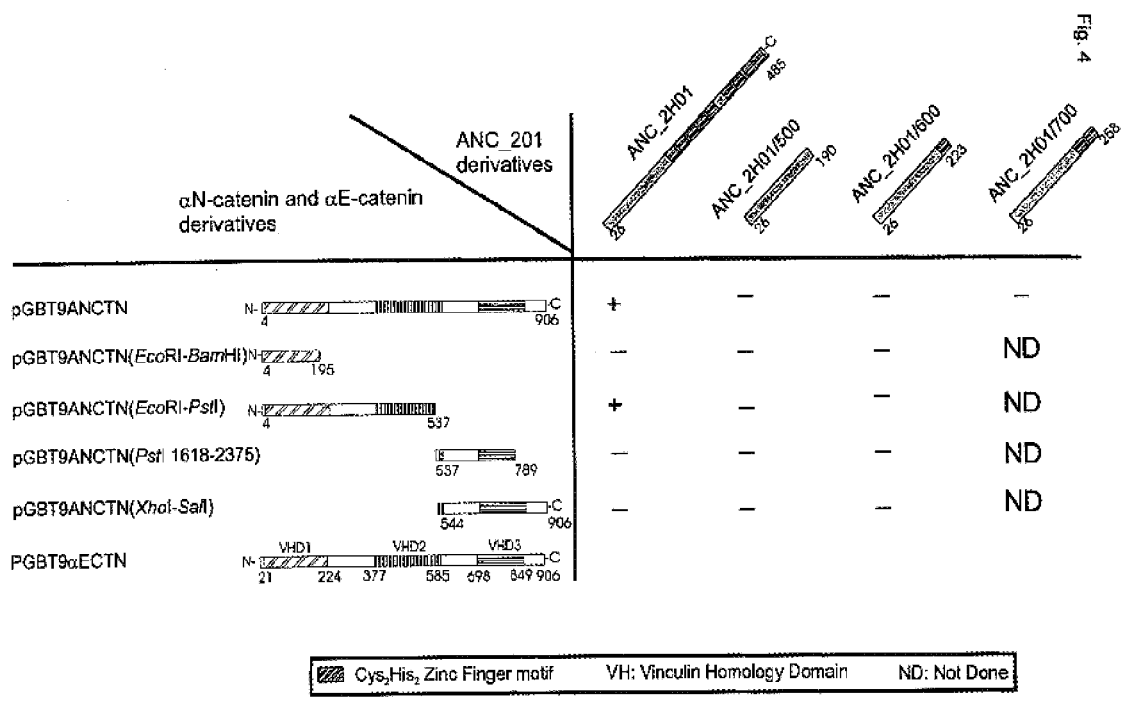
FIG. 4. Analysis of interaction of different parts of αN-catenin and full-length αE-catenin with ANC_2H01 and different parts thereof. VH: Vinculin Homology domain; ND: Not Done.

Up to now, there has been no report of zinc finger proteins binding to catenin or αN-catenin. Furthermore, the invention provides a nucleic acid or derivative thereof corresponding to a nucleic acid or functional fragment thereof encoding a zinc finger protein or other signalling or gene regulatory protein capable of interacting or binding with α-catenins, for example, αN-catenin or an α-catulin. For example, the invention provides a zinc finger protein encoded by said nucleic acid interacting with catenin, such as, for example, with αN-catenin. The catenin protein, forming a complex together with the zinc finger protein, is involved in signalling and gene regulation in, for example, transcriptional pathways.

In a preferred embodiment, the invention provides a nucleic acid according to the invention which is a cDNA molecule, as, for example, described in the experimental part of this description.

Furthermore, the invention provides an expression vector comprising a nucleic acid according to the invention. An example of such a vector can be found in the experimental part of the description. It is within the skills of the artisan to provide vectors that have been provided with single or multiple nucleic acid changes, deletions and/or insertions or other mutations of a nucleic acid sequence.

Furthermore, the invention provides a cell capable of expressing the zinc finger protein or functional fragments thereof as provided by the invention. For example, the invention provides a cell comprising a genome in which a nucleic acid sequence corresponding to a nucleic acid according to the invention has been modified. Such a modification can comprise, for example, a site-directed, or transposon-directed, or chemically induced mutation of a nucleic acid encoding a (fragment) of a gene encoding an catenin-binding zinc finger protein, be it in the intronic or exonic sequences of said gene.

The invention also provides a cell comprising a nucleic acid according to the invention that has been introduced via recombinant means known to the skilled artisan, such as, for example, via homologous recombination techniques or by using a vector according to the invention. An example of such a cell according to the invention is provided in the experimental part of the description wherein said cell is a yeast cell, such as for use in a two-hybrid interaction assay.

The invention also provides a cell capable of expressing a catenin-binding protein or derivative or fragment thereof, said protein comprising a catenin binding domain or capable of complexing with catenin. Such a cell provided by the invention is for example derived of a cell comprising a genome in which a nucleic acid sequence corresponding to a nucleic acid according to the invention has been modified or derived from a cell comprising a nucleic acid according to the invention. Expression of proteins in recombinant cells is, in itself, a technique available to the average artisan. An example is provided in the experimental part of this application, wherein yeast cells expressing a catenin-binding protein are provided.

Furthermore, the invention provides an animal comprising a cell according to the invention. Such an animal is for example a transgenic animal obtained by modifying an embryonic stem cell. Stem cell modifications, as well as modifications of other cells, are known to the average skilled artisan. Such an animal is, for example, a homozygous knock-out animal or a heterozygous animal, such as a cross between a knock-out animal with a wild type animal, or is otherwise modified in a nucleic acid fragment in its genome that corresponds to a nucleic acid provided by the invention. In a preferred embodiment of the invention, said animal is a mouse.

The invention also provides a zinc finger protein or derivative or fragment thereof, said protein capable of complexing with catenin, preferably with αN-catenin. Preferably, such a protein is derived by recombinant techniques and encoded by a nucleic acid according to the invention. Proteins, be it natural proteins, or recombinant versions thereof, can easily be isolated by a skilled artisan when, for example, at least a part of the amino acid sequence, or a specific antibody directed against the protein, is provided. The invention provides such an isolated or recombinant catenin-binding zinc finger protein, or (poly) peptide, or derivatives, or fragments thereof. In addition, the invention provides an antibody specifically directed against such a protein or (poly)peptide or derivative or fragment thereof according to the invention. It is within the skills of the average skilled artisan to provide a (synthetic) antibody directed against a protein or fragment thereof once, for example, the amino acid sequence or the isolated protein is provided.

The invention also provides a method for identifying a candidate drug comprising use of a cell, or an animal, or a protein, or an antibody according to the invention. Candidate drugs, often first selected or generated via combinatorial chemistry, can now be tested and identified using a method provided by the invention. Such a candidate drug or compound can for example be tested on and selected for its effect on zinc finger protein regulated nuclear translocation of catenin as measured, for example, according to the experimental part of the description. For example, a test compound or drug which inhibits the nuclear translocation of catenin is a candidate drug for therapy of cancer or neurological disorders. The mRNA encoding the zinc finger protein is found in all human tissues examined so far, with a low expression level in most of the tissues and a stronger mRNA signal in pituitary gland and adrenal gland. Lung, placenta, fetal liver and fetal lung also showed expression of the mRNA, but lower than the pituitary gland and the adrenal gland (see section Multiple tissue RNA dot blot). The partial cDNA encoding the zinc finger protein was isolated from a human kidney cDNA library and the 5'RACE fragment was obtained using mammary gland mRNA. On the other hand, αN-catenin is known to be mainly neurally expressed. Furthermore, the invention provides a method for diagnosing cancer or neurological disorders comprising use of a nucleic acid, a cell or an animal, or a protein or an antibody according to the invention. A test or compound which inhibits either interaction of the zinc finger protein with αN-catenin or the interaction of the zinc finger protein with DNA-target sequences, is also considered as a candidate drug for therapy of cancer or neurological disorders. Other applications are simplified by discrimination between different types of cancer or neurological disorders, aiming at for instance improved diagnosis, prognosis and therapy.

The invention further provides a method for modulating binding of Brx/proto-Lbc with α-catulin, or for modulating the activity of Brx/proto-Lbc by α-catulin, or for modulating the activity of α-catulin by Brx/proto-Kbc, as is discussed further in the Examples section included herein.

The invention is further explained in the Examples section included below, and though the present invention is discussed herein with respect to specific examples, the examples provided herein are provided for illustrative and explanatory purposes only. The scope of the present invention is to be defined by the appended claims.

EXAMPLES

The present invention relates to the isolation (in a yeast two-hybrid screen) of a novel human zinc finger protein associated with a member of the α-catulin/vinculin family, preferably with a human isoform of α-catenin, termed αN-catenin. The interaction we observed is αN-catenin specific, since the epithelial αE-catenin does not interact with the zinc finger protein using the two-hybrid system. The cDNA of the isolated $Cys_2His_2$-type zinc finger protein was completed using 5= RACE technology. In human cells transfected with the former cDNA, the full-length zinc finger protein localizes to the nucleus. In human cells transfected with a cDNA of αN-catenin, this protein is expressed in the cytoplasm. When these two cDNAs are co-expressed, both proteins colocalize in the nucleus. These results indicate the formation of a complex between the zinc finger protein and αN-catenin and a subsequent translocation to the nucleus. To date, there has been no report of a nuclear zinc finger protein binding to αN-catenin, nor of nuclear localization of the latter. The presence of the zinc finger domain at the carboxy-terminus, consisting of 9 $Cys_2His_2$ zinc fingers with putative DNA binding properties, shows that the isolated zinc finger protein might bind to specific DNA sequences. Taking together with the knowledge that αN-catenin is expressed mainly in the neural system, it might play a role in the transcriptional regulation of target genes, in particular in tumors and in the neural system. Moreover, we report the isolation (again, in a yeast two-hybrid screen) of a fragment of the Brx/proto-Lbc protein interacting with human α-catulin, which is homologous to both α-catenin and vinculin.

Material and Methods
Bacterial Strains and Cell Lines

*Escherichia coli* DH5α (supE44, hsdR17, deoR, recA1, endA1, lacZDM15) and *E. coli* HB101 (supE44, mcrB, mrr, hsdS20, recA1) were used for transformations, plasmid propagation and isolation. The bacteria were grown in LB medium supplemented with 100 μg/ml ampicillin. For selection of the two-hybrid cDNA-library plasmid, transformed HB101 bacteria were grown on minimal M9 medium, supplemented with 50 μg/ml ampicillin, 40 μg/ml proline, 1 mM thiamine-HCl and 1% of the appropriate amino acid drop out solution. After selection, the bacteria were maintained in LB medium supplemented with 50 μg/ml ampicillin. Most cell lines used were obtained from the American Type Culture Collection (ATCC, Rockville, Md.): colon adenocarcinoma cells DLDI (CCL-221) and HCT116 (CCL-247); ileocecal adenocarcinoma HCT8 (CCL-244); SV-40 virus transformed lung fibroblasts WI-38 VA13 subline 2RA (CCL-75.1; abbreviated below as VA13); prostate adenocarcinoma PC3 (CRL-1435); epidermoid carcinoma A431 (CRL-1555). The MCF-7/AZ cell line is derived from the MCF-7 (HTB-22) human mammary carcinoma cell line (Bracke et al., 1991). The mouse cell line Neuro2A (neuroblastoma-derived) was also obtained from the ATCC.

The HEK293T, a human embryonic kidney cell line transfected with SV40 large T-antigen (SV40 tsA1609) (Graham et al., 1977; DuBridge et al., 1987), was kindly provided by Dr. M. Hall (University of Birmingham, UK), and was used for transient eukaryotic expression. HEK293T cells were grown at 37° C. with 5% $CO_2$ in Dulbecco minimal essential medium (DMEM, Gibco BRL Life Technologies, Paisly, UK) supplemented with 10% FCS, 0.03% glutamine, 100 U/ml penicillin, 100 mg/l streptomycin and 0.4 mM sodium pyruvate.

GLC34 and GLC8 are cell lines derived from small cell lung carcinomas, established as described by de Leij et al. (1985), and were kindley made available by Dr. Charles Buys and Dr. Lou de Leij (University of Groningen, the Netherlands). MKN45 is a gastric carcinoma cell line (Motoyama and Watanabe, 1983).

The KC8 bacterial strain was used for selectively rescuing either the AD or DNA-BD vector from yeast after a GAL4 or LexA two-hybrid library screening. This KC8 strain has the following genotype: hsdR, leuB600, trpC9830, pyr::Tn5 (conferring kanamycin-resistance), hisB463, lacDeltaX74, strA, galU, galK. It carries the trpC, leuB, and hisB mutations for complementation to yeast TRP1, LEU2, and HIS3 wild-type genes, respectively. Tranformed KC8 bacteria were grown on minimal M9 medium, supplemented with 50 μg/ml ampicillin, 50 μg/ml proline, 1 mM thiamine-HCl and an amino acid mixture lacking Trp.

Plasmids and Gene Assembly

Restriction enzymes were purchased from Gibco BRL Life Technologies (Paisley, UK) or from New England Biolabs (Beverly, Mass., USA). Restriction enzymes were used according to manufacturers' recommendations. All PCR reactions were performed using Vent™ (Biolabs) DNA polymerase. The primers for PCR amplification were either home made (University of Ghent) or obtained from Gibco BRL. The standard PCR mixture, in a reaction volume of 100 μl, contained template cDNA (plasmid), 25 pmol of both specific primers, 200 μM dXTPs and the PCR buffer supplied with Vent™ DNA polymerase. Unless otherwise stated, no additional $MgSO_4$ was added. VentTm DNA polymerase was used at 1 U/reaction. The DNA amplification was performed in the PTC-200 Peltier Thermal Cycler PCR System (MJ Research, Watertown, Mass.). The PCR program started with a DNA denaturating step at 94° C. for 3 min, followed by 80° C. for 1 min. Cycling conditions were 94° C. for 1 min, 50–60° C. for 30 sec and 72° C. for 2 min. This was repeated for a total of 35 cycles and was followed by a final extension step at 72° C. for 10 min.

Construction of the Plasmid Encoding the αN-catenin GAL4-DBD Hybrid Protein for Two-hybrid Screening For the two-hybrid screen the almost full-length cDNA of human αN-catenin (residues 4–906) was fused in frame to the GAL4 DNA binding domain in the pAS2 vector (Matchmaker™, Clontech, Palo Alto, Calif.). This construct was called pAS2ANCTN and was created using amplification by polymerase chain reaction (PCR) and restriction fragments. For construction of this pAS2ANCTN two-hybrid bait plasmid, we used the expression plasmid pPNhANCTN, which contains the human αN-catenin coding sequence flanked by part of the 5' and 3'UTR. The cDNA for αN-catenin was kindly provided by Dr. C. Petit (Institut Pasteur, Paris; Claverie et al., 1993). Using a specific sense primer completed with the XmaI restriction site (underlined) 5'-ACCCCCCGGGGGCAACTTCACCTATCATTC-3' (=FVR137F; Table 4) (SEQ. I.D. NO. 62) and a compatible antisense primer 5'-GCCGCCGCCTTCCTTTTCATTTCCGCTCTT-3' (=FVR138R; Table 4) (SEQ. I.D. NO. 63), we amplified a PCR fragment from the pPNhANCTN plasmid containing the XmaI restriction site at the 5' end. This PCR fragment was digested with XmaI and BanI and ligated together with a BanI-HindIII fragment of the αN-catenin cDNA in the XmaI-HindIII digested pAS2 vector. The in-frame cloning was confirmed by DNA sequence analysis using the vector specific forward primer 5'-ATCATCGGAAGAGAGTAGTA-3' (=FVR175F; Table 2) (SEQ. I.D. NO. 57). To check for the insertion of the complete fragment, the constructed plasmid was also sequenced with a vector specific reverse primer 5'-AAAATCATAAATCATAAGAA-3' (=FVR217R; Table 2) (SEQ. I.D. NO. 59). The plasmid was assayed for expression of the fusion protein in yeast using Western blot analysis with an antibody directed against the GAL4 DNA binding domain (anti GAL4 DBD rabbit polyclonal antiserum, UBI, Lake Placid, N.Y.).

Construction of the Plasmids Encoding Fragments of αN-catenin Fused to the GAL4-DBD Several restriction fragments of pAS2ANCTN were subcloned into the pGBT9 (Clontech, Palo Alto, Calif.; Bartel et al., 1993) to construct plasmids encoding different parts of the αN-catenin protein fused to the GAL4 DNA binding domain. An EcoRI-BamHI fragment (encoding residues 4–193), an EcoRI-PstI fragment (encoding residues 4–535), a PstI fragment (encoding residues 535–787) and a XhoI-SalI fragment (encoding residues 543–906) were isolated and ligated in frame with the GAL4 DNA binding domain in the pGBT9 vector digested with the appropriate restriction enzymes. The plasmids were designated pGBT9ANCTN (EcoRI-BamHI), pGBT9ANCTN(EcoRI-PstI), pGBT9ANCTN(PstI 1618-2375) and pGBT9ANCTN-(XhoI-SalI), respectively. The in-frame cloning of the fragments was confirmed by DNA sequence analysis using the vector specific forward primer 5'-ATCATCGGAAGAGAGTAGTA-3' (=FVR175F; Table 2) (SEQ. I.D. NO. 57). The inserts were also sequenced with the vector-specific reverse primer (=FVR217R; Table 2) 5'-AAAATCATA-AATCATAAGAA-3'(SEQ. I.D. NO. 59).

Construction of the Plasmid Encoding αE-catenin Fused to the GAL4-DBD

A human fetal kidney 5' Stretch cDNA library (Clontech, Palo Alto, Calif.) in vector λDR2 was screened with a $^{32}$P-labeled αE-catenin-specific probe. This resulted in the isolation of the pDR2αECTN plasmid (phages were converted in vivo into the pDR2-derived plasmids according to the manufacturers protocol), containing the full-length cDNA of αE-catenin. The plasmid was digested with SalI, SphI and Eco47III. The SalI/SphI and the Eco47II/SphI fragments were ligated into the SmaI/SalI digested pGBT9 vector. The two-hybrid plasmid was called pGBT9αECTN and was analysed for in-frame cloning by DNA sequence analysis using the vector-specific forward primer FVR175F (Table 2). The insertion of the fragments was confirmed by sequencing the 3' end using the vector-specific primer FVR217R (Table 2).

Construction of the Plasmid pJ6 αE-catenin for Eukaryotic Expression

A human fetal kidney 5' Stretch cDNA library (Clontech, Palo Alto, Calif.) in vector αDR2 was screened for αE-catenin and several clones were obtained, of which the largest were pDR2αECAT1 (940-3433) and pDR2αECAT3 (100-2349). To complete the cDNA, the very 5' end of αE-catenin was amplified from DLD1 cDNA using the primers FVR53F (5'-CTTCGGGCCTCTGGAATTTA-3') (SEQ. I.D. NO. 128) and FVR73R (5'-CGACATCAGGGTGCTGTAGG-3') (SEQ. I.D. NO. 129) and cloned into the HincII sites of the pGEM11 vector. Part of this product was excised by SfiI (blunted with T4 polymerase) and XbaI and ligated into the pDR2αECAT3 cut with SalI (blunted with Pfu polymerase) and XbaI, to obtain pDR2αECAT3* (37–2349).

From pDR2αECAT3*, a fragment was isolated with SacI (blunted) and NgoAIV and inserted in the pDR2αECAT1 restricted with BamHI (blunted) and NgoAIV, after which pDR2αECATFL (37–3433) was obtained.

The vector PJ6omega (ATTC) was prepared by restriction with EcoRI and completely filling in the BglII site with T4 polymerase. Full-length αE-catenin cDNA was excised from pDR2αECTNFL(37–3433) with EcoRI and SalI (the latter also blunted with Pfu polymerase). In this way, the construct PJ6αECTN(37–3433) was obtained.

Construction of the Plasmids Encoding the Amino-terminal Part of ANC_2H01 Fused to the GAL4-AD The ANC_2H01 clone, isolated from the human kidney cDNA library by performing a two-hybrid screen with αN-catenin as a bait, was digested with BamHI. The 700-bp fragment was isolated and subcloned into the BamHI digested pGAD 10 vector (Clontech, Palo Alto, Calif.). The cDNA insert encodes for the amino-terminal part plus two of the nine zinc fingers. The in-frame cloning was confirmed by DNA sequence analysis. We designated the plasmid ANC_2H01/BamHI.

Using amplification by PCR with compatible primers containing an additional restriction site, we subcloned parts of the ANC_2H01 cDNA encoding for the amino-terminal part of the protein, lacking any functional zinc finger. For this construct, PCR amplification from the initial ANC_2H01 two-hybrid clone was performed using the forward primer 5'-GCACTATGGCCAGAAACAGAAATCAGA-3' (=FVR345F; Table 1) (SEQ. I.D. NO. 18), compatible with the reverse primer 5'-G GAATTCTGGGCAGTCACATTCAAAG-3' (=FVR346R; Table 1) (SEQ. I.D. NO. 19), which included an EcoRI restriction site (underlined). The amplified fragment was digested with XbaI/EcoRI. A second fragment was isolated as a BamHI/XbaI fragment of ANC_2H01. Both fragments were ligated in the two-hybrid vector pGAD10 double digested by BamHI/EcoRI. We named the final plasmid ANC_2H01/500.

Another construct, containing a cDNA fragment encoding the amino-terminal part of the initial ANC_2H01 plus half of the first zinc finger, was made using the same strategy. We amplified a PCR fragment from ANC_2H01 using the same forward primer (=FVR345F; Table 1) that was compatible with the reverse primer 5'-G GAATTCCATATGCTGCTTTAAGTCAG-3' (=FVR347R; Table 1) (SEQ. I.D. NO. 20), in which an EcoRI site (underlined) was included. The plasmid was called ANC_2H01/600. The in-frame cloning and the insertion of the fragments were confirmed by DNA sequence analysis, using primers FVR 174F (Table 2) and FVR 192R (Table 2) for each of the constructed plasmids.

Construction of the Plasmid for Eukaryotic Expression of Epitope Tagged Protein

We constructed an expression vector for eukaryotic expression of the ANC_2H01 full-length protein fused to the E-tag. We used the NotI-KpnI fragment of the vector pEFHOBES (a kind gift from M. Van de Craen, Department of Molecular Biology, VIB-University of Ghent, Belgium), consisting of the expression vector pEF-BOS (Mizushima and Nagata, 1990), in which the E-tag derived from plasmid pCANTAB5E (Pharmacia), is inserted. To construct the expression vector pEFBOSANC_2H01E, which encodes for the ANC_2H01 protein fused at its amino-terminal side to the E-tag, a three points ligation was set up. The first fragment was amplified from the cloned 5' RACE product (in pGEMT) by using the forward primer 5'-ATAAGAAT GCGGCCGCTATGAATGAGTATCCTAAAA-3' (=FVR662F; Table 1) (SEQ. I.D. NO. 42) which contains a NotI restriction site (underlined) and a compatible reverse primer (=FVR663R; Table 1) 5'-CGGATACAGCATAGCGTAGAAAAGGCAGTGT GGTC-3'(SEQ. I.D. NO. 43). The amplified fragment was digested with NotI and AlwNI. The second fragment was obtained by digestion of the initial two-hybrid clone of ANC_2H01 with XhoI and NcoI and ligation of this fragment into the XhoI-NcoI digested vector pJRD 184 (Heusterspreute et al., 1985; John Davis, personal communication). This clone was finally used for the isolation of the AlwNI-KpnI fragment of the ANC_2H01 cDNA. Both fragments were ligated into the NotI-KpnI fragment of the vector pEFHOBES. The in-frame cloning was confirmed by DNA sequence analysis with the ANC_2H01-specific primer 5'-TCTGTTTCTGGCCTTGATTC-3' (=FVR310R; Table 1) (SEQ. I.D. NO. 17).

Another three points ligation was set up to fuse the ANC_2H01 protein carboxyterminally to the E-tag. The vector used was the pDNATRADE (gift from Dr. W. Declercq and B. Depuydt, Department of Molecular Biology, VIB-University of Gent, Belgium), which was digested with the NotI and HindIII restriction enzymes. The HindIII site was completely filled in. The second fragment was amplified from the initial two-hybrid clone ANC_2H01 using the forward primer 5'-ATCGTCAGCGACATAGGTCAATGGAATTTTCT CTGAT-3' (=FVR660F; Table 1) (SEQ. I.D. NO. 40) and the compatible reverse primer 5'-ATAAGAAT GCGGCCGCTGTTGTCTCATGGACTGGAAG-3' (=FVR661 R; Table 1) (SEQ. I.D. NO. 41), containing a NotI restriction site (underlined). The obtained PCR fragment was digested with AlwNI and NotI restriction enzymes. The third fragment was obtained from the digestion of pGEMTRACE1C with Bsu361 and AlwNI. The constructed plasmid was called pDNA-ANC_2H01E.

Construction of Plasmids Encoding αN/αE-catenin Chimeras Fused to the GAL4-DBD

We constructed six different plasmids in which different parts of either αN-catenin cDNA or αE-catenin cDNA were exchanged with the homologous part of, respectively, the αE-catenin cDNA or the αN-catenin cDNA. This was done by a combination of PCR products and restriction fragments. A first fragment was amplified from the pGBT9ANCTN plasmid by using the forward primer 5'-CG GAATTCCCGGGGGCAACTTC-3' (=FVR1241; Table 6) (SEQ. I.D. NO. 73) which contains an EcoRI restriction site (underlined), and a compatible reverse primer 5'- TCAT-TAAGAGCATATGCCAGCT -3' (=FVR1243; Table 6) (SEQ. I.D. NO. 74) which includes a new NdeI restriction site (underlined). The PCR product was digested with the appropriate restriction enzymes and subsequently ligated into the EcoRI-NdeI digested pGBT9αECTN plasmid. This construct was named pGBT9αNCTNVH1E referring to the vinculin-homologous domain 1 (VH1) of αN-catenin that is replaced by that of αE-catenin (FIG. 10).

To construct pGBT9αECTNVH1N, a fragment was amplified from the pGBT9αECTN plasmid using the forward primer 5'-AATTCCCGGGCGCCCAGCTAGC-3' (=FVR1244; Table 6) (SEQ. I.D. NO. 75) comprising an XmaI restriction site (underlined) and a compatible reverse primer 5'-TCCTCCAGGGACGGCCGAAAGC-3' (=FVR1245; Table 6) (SEQ. I.D. NO. 76) which includes an EagI restriction site (underlined). Subsequently, the amplified fragment was digested with the appropriate restriction enzymes and ligated into the fragment obtained by XmaI-EagI digestion of pGBT9ANCTN. The constructed plasmid is called pGBT9αECTNVH1N and contains the cDNA of αE-catenin in which the VH1 domain of αE-catenin is replaced by that of αN-catenin (FIG. 10).

The vinculin-homologous domain 2 of αN-catenin (VH2N) was amplified from the pGBT9ANCTN plasmid using the forward primer 5'-AGGTTC CGGCCGTCCCTGCA-3' (=FVR1246; Table 6) (SEQ. I.D. NO. 77) and a compatible reverse primer 5'-GGAATATC GGTACCTGCTCAGC-3' (=FVR1247; Table 6) (SEQ. I.D. NO. 78), including, respectively, an EagI and a KpnI restriction site (underlined). A second fragment containing the vinculin-homologous domain 3 of αE-catenin (VH3E) was generated by PCR from the pGBT9αECTN plasmid, using the forward primer 5'-AACA GGTACCCAGCTTCCAGG-3' (=FVR1252; Table 6) (SEQ. I.D. NO. 83) which includes a KpnI restriction site (underlined) and the reverse primer 5'-CTTGGCTGCAG GTCGACTCT-3' (=FVR1253; Table 6) (SEQ. I.D. NO. 84), containing a SalI restriction site (underlined). These two PCR fragments were digested with the appropriate restriction enzymes and subsequently ligated into the EagI-SalI digested pGBT9αNCTNVH1E. The constructed plasmid contains the cDNA of αE-catenin in which the VH2 is replaced by that of αN-catenin and is therefore named pGBT9αECTNVH2N (FIG. 10). These same two digested PCR fragments were ligated into the EagI-SalI digested pGBT9ANCTN plasmid to obtain the pGBT9αNCTNVH3E plasmid, in which the VH3 domain of αN-catenin is replaced by that of αE-catenin (FIG. 10).

A PCR fragment was generated from the pGBT9αECTN plasmid using a forward primer 5'-ACTGG CATATGCACTCAATAAC-3' (=FVR1250, Table 6) (SEQ. I.D. NO. 81), containing an NdeI restriction site (underlined), and a compatible reverse primer 5'-CCTGGAAGCTGGGTACCTGTTC-3' (=FVR1251; Table 6) (SEQ. I.D. NO. 82), including a KpnI restriction site (underlined). A second fragment was generated by PCR from pGBT9ANCTN using the forward primer 5'-GCTGAGCAGGTACCGATATTCC-3' (=FVR1248F; Table 6) (SEQ. I.D. NO. 79) and a reverse primer 5'-TTGGCTGCAGGTCGACGGTATC-3' (=FVR1249R; Table 6) (SEQ. I.D. NO. 80), including, respectively, a KpnI and a SalI restriction site (underlined). These two PCR fragments were digested with the appropriate restriction enzymes and ligated into the NdeI-SalI digested pGBT9αECTNVH1N plasmid to obtain the pGBT9αNCTNVH2N (FIG. 10). To construct the pGBT9αECTNVH3N plasmid, these same two PCR fragments were ligated into the NdeI-SalI digested pGBT9αECTN (FIG. 10).

The in-frame cloning of all the different fragments was confirmed by DNA sequence analysis of the constructs, using primers FVR51, FVR54, FVR157, FVR160, FVR217, FVR738, FVR 1157 and FVR1311 (Table 6).

Figure 12:
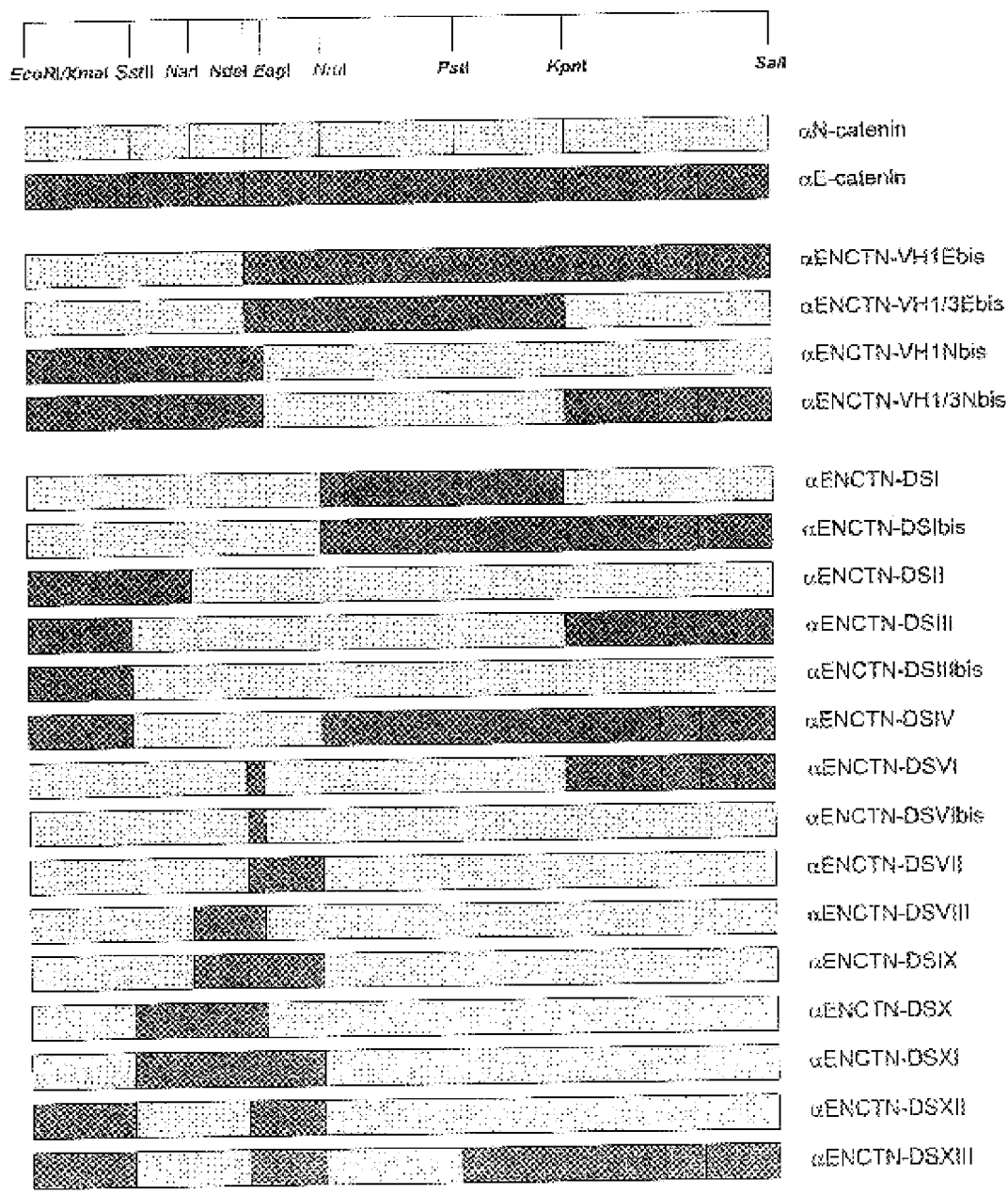
FIG. 12. Schematic representation of the coding potential of the αE/αN-chimeric cDNAs inserted into the pGBT9 two-hybrid vector. The restriction sites used for the cloning of the different constructs are indicated on top. The position of the alternatively used exon at the carboxyterminus of both αE- and αN-catenin is indicated as a shaded box in the αE-catenin-derived sequences.

Subsequent to the construction of these first six plasmids encoding αN/αE-catenin chimeras fused to the GAL4-DBD, we constructed another 19 plasmids in which several domains of the αN-catenin cDNA were replaced by the homologous domains of the αE-catenin cDNA and vice versa (FIG. 12).

The PGBT9αECTNVH1bis plasmid was constructed by insertion of two PCR fragments into the EagI-SalI digested pGBT9αNCTN. A first PCR fragment was amplified from the pGBT9αECTN, using the forward primer 5'-CTTT CGGCCGTCCCTGGA-3' (=FVR1428F; Table 6) (SEQ ID NO: 87) which includes an EagI restriction site (underlined and in bold) and the reverse primer 5'-CCTGGAAGCTG GGTACCTGTTC-3' (=FVR1251R; Table 6) (SEQ ID NO: 82), including a KpnI restriction site (underlined and in bold). A second fragment was generated by PCR from the pGBT9αECTN using the forward primer (=FVR1252F; Table 6) 5'-AACAGGTACCCAGCTTCCAGG-3' (SEQ. I.D. NO. 83) which includes a KpnI restriction site (underlined and in bold) and the reverse primer (=FVR1253R; Table 6) 5'-CTTGG CTGCAGGTCGACTCT-3' (SEQ ID NO: 84), containing a SalI restriction site (underlined and in bold). Both PCR fragments were digested with the appropriate restriction enzymes and ligated into the above-mentioned digested vector.

Another plasmid, pGBTαNCTNVH2Ebis, was also constructed by insertion of two PCR fragments into the EagI-SalI digested pGBT9αNCTN. A first PCR fragment was amplified from the pGBT9αECTN, using the forward primer 5'-CTTTCGGCCGTCCCTGGA-3' (=FVR1428F; Table 6) (SEQ ID NO: 87) which includes an EagI restriction site (underlined and in bold) and the reverse primer (=FVR1251R; Table 6) 5'-CCT-GGAAGCTG GGTACCTGTTC-3' (SEQ ID NO: 82), including a KpnI restriction site (underlined and in bold). A second fragment was generated by PCR from pGBT9αNCTN using the forward primer 5'-GCTGAGCAGGTACCGATATTCC-3' (=FVR1248F; Table 6) (SEQ. I.D. NO. 79) and a reverse primer 5'-TTGGCTGCAGGTCGACGGTATC-3' (=FVR1249R; Table 6) (SEQ ID NO: 80), including, respectively, a KpnI and a SalI restriction site (underlined and in bold). These two PCR fragments were digested with the appropriate restriction enzymes and ligated into the EagI-SalI digested pGBT9αNCTN.

The pGBT9αNCTNVH1Ebis was obtained by insertion of a PCR fragment into the NdeI-KpnI digested pGBT9αECTNVH3N plasmid. The PCR fragment was amplified from the pGBT9αNCTN by using the forward primer 5'-TGCTGGCATATGCTCTTAATGAGT-3' (=FVR1427F; Table 6) (SEQ ID NO: 86) which includes a NdeI restriction site (underlined and in bold) and the reverse primer (=FVR1247R; Table 6) 5'-GGAATATC GGTACCTGCTCAGC-3' (SEQ ID NO: 78), including, a KpnI restriction site (underlined and in bold). Before ligation, the PCR fragment was digested with the appropriate restriction enzymes.

To obtain plasmid pGBT9αECTNVH2Nbis, a first fragment was generated by PCR from the pGBT9αANCTN by using the forward primer 5'-TGCTGG CATATGCTCTTAATGAGT-3' (=FVR1427F; Table 6) (SEQ ID NO: 86) which includes a NdeI restriction site (underlined and in bold) and the reverse primer (=FVR1247R; Table 6) 5'-GGAATATC GGTACCTGCTCAGC-3' (SEQ ID NO: 78), including a KpnI restriction site (underlined and in bold). A second PCR fragment was amplified from plasmid pGBT9αECTN using the forward primer 5'-AACA GGTACCCAGCTTCCAGG-3' (=FVR1252F; Table 6) (SEQ. I.D. NO. 83) which includes a KpnI restriction site (underlined and in bold), and the reverse primer (=FVR1253R; Table 6) 5'-CTTGG CTGCAGGTCGACTCT-3' (SEQ ID NO: 84), containing a SalI restriction site (underlined and in bold). Both PCR fragments were digested with the appropriate restriction enzymes and ligated into the NdeI-SalI digested pGBT9αECTN plasmid.

The plasmid pGBT9αENCTN-DSI was obtained via a three points ligation. A first fragment was generated by digestion of the pGBT9αNCTNVH2E with an NdeI and a KpnI restriction enzyme. A second fragment was generated by PCR from the pGBT9αNCTN plasmid, using the forward primer 5'-TGCTGGCATATGCTCTTAATGAGT-3' (=FVR1427F; Table 6) (SEQ ID NO: 86) which includes a NdeI restriction site (underlined and in bold) and the reverse primer (=FVR1545R; Table 6) 5'-CTGTCTCCTTAGA TCGCGAGTTTTC-3' (SEQ ID NO: 91), containing an NruI restriction site (underlined and in bold). Another PCR fragment was generated from the pGBT9αECTN plasmid using a forward primer 5'-TGACCAAGAAGACTCGCGACTT-3' (=FVR1543F, Table 6) (SEQ ID NO: 89), containing an NruI restriction site (underlined and in bold), and a compatible reverse primer (=FVR125IR; Table 6) 5'-CCTGGAAGCTGGGTACCTGTTC-3' (SEQ ID NO: 82), including a KpnI restriction site (underlined and in bold). These two PCR fragments were ligated into the NdeI-KpnI digested pGBT9αNCTNVH2E.

To construct the plasmid pGBT9αENCTN-DSIbis, a fragment was generated by digestion of the pGBT9αENCTN-DSI with an EcoRI and a KpnI restriction enzyme. This fragment was ligated into the EcoRI-KpnI digested pGBT9αNCTNVH3E plasmid.

To obtain the pGBT9αENCTN-DSII plasmid, two PCR fragments were ligated into the XmaI-EagI digested pGBT9αNCTN plasmid. A first PCR fragment was generated from the pGBT9αECTN plasmid using a forward primer 5'-AATTCCCGGGCGCCCAGCTAGC-3' (=FVR1244F, Table 6) (SEQ. I.D. NO. 75), containing an XmaI restriction site (underlined and in bold), and a compatible reverse primer 5'-GATTCCTCTA GCGGCCGCCATCTGATCA-3' (=FVR1781R; Table 6) (SEQ ID NO: 99), including a NotI restriction site (underlined and in bold). A second fragment was generated by PCR from pGBT9αNCTN using the forward primer 5'-TTATTATATTGCGGCCGCTAGAGGGGCT-3' (=FVR1779F; Table 6) (SEQ ID NO: 97) and a reverse primer 5'-CTGTCTCCTTAGATCGCGAGTTTTC-3' (=FVR1545R; Table 6) (SEQ ID NO: 91), including, respectively, a NotI and an NruI restriction site (underlined and in bold). These two PCR fragments were digested with the appropriate restriction enzymes and ligated into the XmaI-EagI digested pGBT9αNCTN.

To construct the pGBT9αENCTN-DSIII, a PCR fragment was amplified from the pGBT9αECTN plasmid using a forward primer 5'-AATTCCCGGGCGCCCAGCTAGC-3' (=FVR1244F, Table 6) (SEQ. I.D. NO. 75), containing an XmaI restriction site (underlined and in bold), and a compatible reverse primer (=FVR1553R; Table 6) 5'-AAATCAGCAAACGAGTAACCGCGGAGAGC-3' (SEQ ID NO: 94), including an SstII restriction site (underlined and in bold). This PCR fragment was digested with the appropriate restriction enzymes and ligated into the XmaI-SstII digested pGBT9αNCTN-VH3E plasmid.

The pGBT9αENCTN-DSIIIbis plasmid was constructed by insertion of the NheI-KpnI fragment derived from the pGBT9αENCTN-DSIII plasmid into the NheI-KpnI digested pGBT9αECTNVH3N plasmid.

To construct the pGBT9αENCTN-DSIV plasmid, an SstII-KpnI fragment obtained by restriction digest of the pGBT9αENCTN-DSI plasmid with the appropriate restriction enzymes, was ligated into the SstII-KpnI digested pGBT9αENCTN-DSIII plasmid.

The pGBT9αENCTN-DSVI plasmid was constructed using two digestion fragments. The first fragment was obtained by digestion of the pGBT9αECTNVH1N plasmid with an XmaI and an NdeI restriction enzyme. This fragment was ligated into the XmaI-NdeI digested pGBT9-αECTNVH2N vector.

The pGBT9αENCTN-DSVIbis plasmid was obtained by ligation of the XmaI-KpnI fragment of the pGBTαENCTN-DSVI plasmid into the XmaI-KpnI digested pGBT9αNCTNVH2E plasmid.

A PCR fragment was generated from the pGBT9αECTN plasmid using a forward primer 5'-ACTGG CATATGCACTCAATAAC-3' (=FVR1250F, Table 6) (SEQ. I.D. NO. 81), containing an NdeI restriction site (underlined and in bold), and a compatible reverse primer (=FVR1546R; Table 6) 5'-GCAAGTCGCGAGTCTTCTT-3' (SEQ ID NO: 92), including an NruI restriction site (underlined and in bold). A second fragment was generated by PCR from pGBT9ANCTN using the forward primer 5'-AAAAC TCGCGATCTAAGGAGAC-3' (=FVR1544F; Table 6) (SEQ ID NO: 90) and a reverse primer 5'-GGAATATC GGTACCTGCTCAGC-3' (=FVR1247R; Table 6) (SEQ ID NO: 78), including, respectively, an NruI and a KpnI restriction site (underlined and in bold). These two PCR fragments were digested with the appropriate restriction enzymes and ligated into the NdeI-KpnI digested pGBT9-αNCTNVH2E plasmid to obtain the pGBT9αENCTN-DSVII derivative.

The plasmid pGBT9αENCTN-DSVIII was obtained via a three points ligation. A first fragment was generated by digestion of the pGBT9αNCTN plasmid with XmaI and EagI restriction enzymes. A second fragment was generated by PCR from the pGBT9αNCTN plasmid, using the forward primer 5'-CGGAATTCCCGGGGGCAACTTC-3' (=FVR1241F; Table 6) (SEQ. I.D. NO. 73) which includes a XmaI restriction site (underlined and in bold) and the reverse primer (=FVR1780R; Table 6) 5'-ATATTTAAT GCGGCCGCCATCTGATCA-3' (SEQ ID NO: 98), containing a NotI restriction site (underlined and in bold). Another PCR fragment was generated from the pGBT9αECTN plasmid using a forward primer (=FVRI 778F, Table 6) 5'-TTATTATATGGCGGCCGCTAGAGGAATC-3' (SEQ ID NO: 96), containing a NotI restriction site (underlined and in bold), and a compatible reverse primer 5'-AAGA CGGCCGAAAGCGCTCC-3' (=FVR1554R; Table 6) (SEQ ID NO: 95), including an EagI restriction site (underlined and in bold). These two PCR fragments were ligated into the XmaI-EagI digested pGBT9αNCTN.

The pGBT9αENCTN-DSIX plasmid was constructed using two digestion fragments. The first fragment was obtained by digestion of the pGBT9αENCTN-DSVIII plasmid with XmaI and NdeI restriction enzymes. Subsequently, this fragment was ligated into the XmaI-NdeI digested pGBT9αENCTN-DSVII vector.

To obtain plasmid pGBT9αENCTN-DSX, a first fragment was amplified by PCR from the pGBT9αECTN plasmid, using a forward primer 5'-TTGCTCT CCGCGGTTACC-3' (=FVR1552F; Table 6) (SEQ ID NO: 93) which includes an SstII restriction site (underlined and in bold) and the reverse primer 5'-AAGA CGGCCGAAAGCGCTCC-3' (=FVR1554R; Table 6) (SEQ ID NO: 95), containing an EagI restriction site (underlined and in bold). The second fragment was obtained by digestion of the pGBT9αNCTN plasmid with SstII and EagI restriction enzymes.

The pGBT9αENCTN-DSXI plasmid was obtained by ligation of the XmaI-NdeI fragment of the pGBTαENCTN-DSX plasmid into the XmaI-NdeI digested pGBT9αENCTN-DSVII plasmid.

The pGBT9αENCTN-DSXII plasmid was obtained by ligation of the ClaI-SstII fragment of the pGBTαENCTN-DSVII plasmid into the ClaI-SstII digested pGBT9αENCTN-DSIII plasmid.

To obtain plasmid pGBT9αENCTN-DSXIII, a PCR fragment was amplified from the pGBT9αECTN plasmid using a forward primer 5'-GCAGCTCGAGTCATTCACGTAG-3' (=FVR2116F, Table 6) (SEQ ID NO: 100), containing an XhoI restriction site (underlined and in bold), and a compatible reverse primer (=FVR1251R; Table 6) 5'-CCTGGAAGCTGGGTACCTGTTC-3' (SEQ ID NO: 82), including a KpnI restriction site (underlined and in bold). This PCR fragment was digested with the appropriate restriction enzymes. A second fragment was generated by an NdeI-XhoI digestion of the pGBT9αENCTN-DSXII plasmid. The two fragments were inserted into the NdeI-KpnI digested pGBT9αENCTN-DSXII plasmid.

Construction of Plasmids Encoding about Full-length ANC-2H01 to Either the GAL4-DBD or GAL4-AD To construct the two-hybrid plasmid, which encodes about the full-length ANC_2H01 protein fused to the GAL4-DBD, a three points ligation was set up. The first fragment was amplified from the cloned 5' RACE product (in PGEMT) by using the forward primer 5'-G GAATTCCTGAATGAGTATCCTAAAAAA-3' (=FVR1237F; Table 1) (SEQ ID NO: 48) which contains a new EcoRI restriction site (underlined), and a compatible reverse primer 5'-ATGCATGCTGTAGAAAAGGCAGTGTGGT-3' (=FVR1238R; Table 1) (SEQ ID NO: 49). The amplified fragment was digested with EcoRI and AlwNI. A second fragment was generated by PCR from the initial two-hybrid clone ANC_2H01 using the forward primer 5'-CGTCGCGGCCCTGCAGATGGATTCAATGGA-3' (=FVR124OF; Table 1) (SEQ ID NO: 50) and a compatible reverse primer 5'-TCCC CCCGGGGGATGAATTTATTATTTTA-3' (=FVR1242R, Table 1) (SEQ ID NO: 51), extended with an XmaI restriction site (underlined). The latter PCR fragment was digested with AlwNI and XmaI. Both digested PCR fragments were ligated into the EcoRI-XmaI fragment of the vectors pGBT9 and pGAD424. These constructed plasmids were called pGBT9ANC_2H01FL and pGAD424ANC_2H01FL, respectively. The in-frame cloning of the fragments was confirmed by DNA sequence analysis for both plasmids.

Construction of Plasmids Encoding Either the Aminoterminal or the Carboxyterminal Part of ANC_2H01 Fused to GAL4-DBD or the GAL4-AD A fragment was amplified from the expression vector pEFBOSANC_2H01E using the forward primer 5'-TCC CCCGGGTATGAATGAGTATCCTAAAAAA-3' (=FVR1411F; Table 1) (SEQ ID NO: 52), extended with an XmaI restriction site (underlined), and the compatible reverse primer 5'-AAAA GTCGACGGCCACTGCTATTAGCTCTC-3' (SEQ ID NO: 53) extended with a SalI restriction site (underlined) (=FVR1412R; Table 1). The fragment was digested with the XmaI and SalI restriction enzymes and ligated into the XmaI-SalI digested pGBT9 vector or the pGAD424 vector. The constructed two-hybrid plasmids encode the aminoterminal, non-zinc finger part of ANC_2H01 fused to the GAL4-DBD or the GAL4-AD, respectively. The plasmids are called pGBTANC_2H01-AT and pGAD424ANC_2H01-AT.

In order to fuse the carboxyterminal, zinc finger part of ANC_2H01 to the GAL4-DBD, another fragment was amplified from the pDNA-ANC_2H01E plasmid, using the forward primer 5'-G GAATTCTTCTATAAATGTGAACTTTGT-3' (=FVR1413F; Table1) (SEQ ID NO: 54), which includes an EcoRI restriction site, and the compatible reverse primer 5'-AAAAGTCGACAAGTTAAAGAGAATAATCAA-3' (SEQ ID NO: 55), extended with a SalI restriction site (=FVR1414R). This PCR fragment was digested with the EcoRI and SalI restriction enzymes and subsequently ligated into the EcoRI-SalI fragment of pGBT9. This plasmid was named pGBT9ANC_2H01-ZF.

The same strategy was followed to construct the pGAD424ANC-2H01-ZF. Hereto, the EcoRI-SalI digested PCR fragment was ligated into the EcoRI-SalI digested pGAD424 vector.

Construction of Plasmids Encoding Various Fragments of the Zinc Finger Domain of ANC_2H01 Fused to the GAL4-DBD For the construction of the pACT2ANC2H01ZF1–3 plasmid, the pGEX4T2ANC2H01-Zn1–3 plasmid was digested with the EcoRI and SalI restriction enzymes. Subsequently, this fragment was ligated into the EcoRI-XhoI digested pACT2 vector (Clontech, Palo Alto, Calif.). The pACT2ANC2H01ZF1–5 plasmid, encoding a GAL4AD-fusion protein with the first five zinc fingers of ANC_2H01, was obtained by ligation of an EcoRI-SalI restriction fragment of the pGEX4T2ANC2H01-ZN1–5 plasmid into the EcoRI-XhoI digested pACT2. The same strategy was followed to construct the pACT2ANC2H01Zn4–5 plasmid. The pGEX4T2-ANC2H01Zn-4–5 was digested with the EcoRI and SalI restriction enzymes and the fragment was ligated into the pACT2 vector digested with the appropriate restriction enzymes. Ligation of the EcoRI-SalI restriction fragment of the pGEX4T2-ANC2H01Zn4–9 plasmid into the EcoRI-XhoI digested pACT2 vector resulted in the construction of the pACT2ANC2H01ZF4–9 plasmid. Finally, the pACT2ANC2H01ZF6–9 plasmid was obtained by insertion of the EcoRI-SalI fragment of the pGEX4T2ANC2H01Zn6–9 plasmid into the pACT2 vector.

Construction of Plasmids Encoding Fragments of ANC_2H01 Fused to GST

Seven constructs were designed, that contained different parts of the ANC_2H01 cDNA fused to the GST (glutathione-S-transferase) in the pGEX-vectors (Amersham Pharmacia Biotech, UK). All fragments were obtained by PCR amplification with the pGBT9-ANC_2H01FL as template. A fragment coding for the aminoterminal part of ANC_2H01 (amino acid residues 1 to 209) was PCR-amplified using the forward primer 5'-CGT GGATCCGAAAAGATATGAATGAGTAT-3' (=FVR1043F, Table 9) (SEQ ID NO: 103), containing a BamHI restriction site, and the reverse primer 5'-CCT CTCGAGCAAAGTTCACATTTATAGAG-3' (=FVR1044R, Table 9) (SEQ ID NO: 104), containing an XhoI restriction site (650 bp). The BamHI/XhoI restriction fragment was cloned into the BamHI/XhoI digested pGEX-5X-1 vector. The resulting plasmid was called pGEX-5X-1-ANC_2H01AT. All other ANC_2H01 cDNA fragments were PCR-amplified using forward primers containing an EcoRI restriction site and reverse primers containing an XhoI restriction site. A fragment coding for the carboxyterminal, zinc finger containing part of ANC_2H01 (amino acid residues 203 to 485) was PCR-amplified using the forward primer 5'-G GAATTCGCCTCTATAAATGTGAACTT-3' (=FVR1045F, Table 9) (SEQ ID NO: 105) and the reverse primer 5'-CCG CTCGAGAAGTTAAAGAGAATAATCAA-3' (=FVR1046R, Table 9) (SEQ ID NO: 152). The EcoRI/XhoI restriction fragment was cloned into the EcoRI/XhoI digested pGEX-4T-2 vector. The resulting plasmid was called pGEX-4T-2-ANC_2H01 Zn. A fragment coding for the zinc fingers 1 to 3 of ANC_2H01 (amino acid residues 203 to 288) was PCR-amplified using the forward primer 5'-GGAATTCGCCTCTATAAATGTGAACTT-3' (=FVR1045F, Table 9) (SEQ ID NO: 105) and the reverse primer 5'-CCGCTCGAGAGAGGTGATCACTAAAATG-3' (=FVR1304R, Table 9) (SEQ ID NO: 106). The EcoRI/XhoI restriction fragment was cloned into the EcoRI/XhoI digested pGEX-4T-2 vector. The resulting plasmid was called pGEX-4T-2-ANC_2H01 Zn1–3. A fragment coding for the zinc fingers 1 to 5 of ANC_2H01 (amino acid residues 203 to 350) was PCR-amplified using the forward primer 5'-GGAATTCGCCTCTATAAATGTGAACTT-3' (=FVR1045F, Table 9) (SEQ ID NO: 105) and the reverse primer 5'-CCTCTCGAGCTTATCACTTAACTCTATTA-3' (=FVR1305R, Table 9) (SEQ ID NO: 106). The EcoRI/XhoI restriction fragment was cloned into the EcoRI/XhoI digested pGEX-4T-2 vector. The resulting plasmid was called pGEX-4T-2-ANC_2H01 Zn1–5. A fragment coding for the zinc fingers 4 to 5 of ANC_2H01 (amino acid residues 288 to 350) was PCR-amplified using the forward primer 5'-GGAATTCTCTATTGGTGTGAACAGTGT-3' (=FVR1306F, Table 9) (SEQ ID NO: 108) and the reverse primer 5'-CCTCTCGAGCTTATCACTTAACTCTATTA-3' (=FVR1305R, Table 9) (SEQ ID NO: 107). The EcoRI/XhoI restriction fragment was cloned into the EcoRI/XhoI digested pGEX-4T-2 vector. The resulting plasmid was called pGEX-4T-2-ANC_2H01Zn4–5. A fragment coding for the zinc fingers 4 to 9 of ANC_2H01 (amino acid residues 288 to 485) was PCR-amplified using the forward primer 5'-GGAATTCTCTATTGGTGTGAACAGTGT-3' (=FVR1306F, Table 9) (SEQ ID NO: 108) and the reverse primer 5'-CCG CTCGAGAAGTTAAAGAGAATAATCAA-3' (=FVR1046R, Table 9) (SEQ ID NO: 152). The EcoRI/XhoI restriction fragment was cloned into the EcoRI/XhoI digested pGEX-4T-2 vector. The resulting plasmid was called pGEX-4T-2-ANC_2H01Zn4–9. A fragment coding for the zinc fingers 6 to 9 of ANC_2H01 (amino acid residues 371 to 485) was PCR-amplified using the forward primer 5'-GGAATTCTCTATTGGTGTGAACAGTGT-3' (=FVR1307F, Table 9) (SEQ ID NO: 109) and the reverse primer 5'-CCG CTCGAGAAGTTAAAGAGAATAATCAA-3' (=FVR1046R, Table 9) (SEQ ID NO: 152). The EcoRI/XhoI restriction fragment was cloned into the EcoRI/XhoI digested pGEX-4T-2 vector. The resulting plasmid was called pGEX-4T-2-ANC_2H01Zn6–9.

The in-frame cloning and the insertion of the fragments were confirmed by DNA sequence analysis, using the vector-specific primers FVR357 and FVR358 (Table 9). Construction of Plasmids Encoding the Full-length ANC_2H01, the Amino Terminal or the Carboxyterminal Part of ANC_2H01 for mRNA Preparation Either the full-length ANC_2H01 or an aminoterminal part or a carboxyterminal part of ANC_2H01 was cloned into the pCS2+ vector (Turner and Weintraub, 1994), or the pCS2+MT vector (containing an aminoterminal Myc tag). The carboxyterminal, zinc finger containing part of ANC_2H01 was cloned using two fragments. The 5' fragment (633 bp) was obtained by PCR-amplification on the pGBT9ANC_2H01FL plasmid with the forward primer 5'-CCATCGATGGATTATAAATGTGAACTTTGTGA-3' (=FVR1691F, Table 10) (SEQ ID NO: 117), containing a ClaI restriction site, and the reverse primer 5'-CATATCCAAGCCTTTCCCACAGTCATCA-3' (=FVR1690R, Table 10) (SEQ ID NO: 116). This fragment was digested with the restriction enzymes ClaI and AccI, yielding a 549-bp fragment. The 3' fragment (371 bp) was obtained by restriction enzyme digestion of the pGAD424ANC_2H01FL plasmid with AccI and SalI. These two fragments were ligated into the ClaI/XhoI digested pCS2+ vector. The resulting plasmid was called pCS2+ANC_2H01ZF. The plasmid pCS2+MTANC_2H01ZF, containing an aminoterminal Myc tag, was cloned likewise, using the same 3' fragment. The 5' fragment (633 bp), however, was obtained by PCR-amplification on the pGBT9ANC_2H01FL plasmid with the forward primer 5'-CATGCCATGGTCTATAAATGTGAACTTTGTGA-3' (=FVR1689F, Table 10) (SEQ ID NO: 115), containing an NcoI restriction site, and the same reverse primer as above (=FVR 1690R, Table 10). These two fragments were ligated into the NcoI/XhoI digested pCS2+MT vector. The aminoterminal part of ANC_2H01 and the full-length ANC_2H01 were also cloned in the pCS2+ vector using two ANC_2H01 cDNA fragments. For both constructs, the 5' fragment (309 bp) was obtained by PCR-amplification on the pDNA-ANC_2H01E plasmid with the forward primer 5'-CCGGAATTCATGAATGAGTATCCTAAAAA-3' (=FVR1686F, Table 10) (SEQ ID NO: 112), containing an EcoRI restriction site, and the reverse primer 5'-TGAGTACGTAGAAAAGGCAGTGTGGTC-3' (=FVR1687R, Table 10) (SEQ ID NO: 113). This fragment was digested with the restriction enzymes EcoRI and AlwNI, yielding a 131-bp fragment. The 3' fragments were obtained by, respectively, an AlwNI/SalI restriction enzyme digest of pGAD424ANC_2H01AT (483-bp fragment) and pGAD424ANC_2H01FL (1395-bp fragment). The 131-bp 5' fragment and the 483-bp or 1395-bp 3' fragment were ligated into the pCS2+ vector to yield, respectively, the plasmids pCS2+ANC_2H01AT and pCS2+ANC_2H01FL. For the cloning of the corresponding Myc-tagged constructs, pCS2+MTANC_2H01AT and pCS2+MTANC_2H01FL, the same 3' fragments were used. The 5' fragment (305 bp), however, was obtained by PCR-amplification on the pGBT9ANC_2H01FL plasmid with the forward primer 5'-CATGCCATGGATGAGTATCCTAAAAAAAGA-3'

(=FVR1688F, Table 10) (SEQ ID NO: 114), containing an NcoI restriction site, and the same reverse primer as above (=FVR1687R, Table 10). The two fragments were ligated into the NcoI/XhoI-digested pCS2+MT vector.

The in-frame cloning and the insertion of the fragments were confirmed by DNA sequence analysis, using the vector-specific primers FVR63F and FVR736R (Table 10) and the ANC_2H01-specific primers FVR274F, FVR512R, FVR513F, and FVR1686F (Table 1).

Construction of Plasmids Encoding Either Full-length ANC_2H01 or ANC 2H01 with an Aminoterminal Deletion, Each Fused to eGFP Full-length ANC_2H01 cDNA was cloned into the pEGFP-C1 vector (Clontech, Palo Alto, Calif.) by using two restriction enzyme fragments. The 5' fragment was obtained through restriction enzyme digestion of the pCS2+ANC2H01AT plasmid with BamHI and HindIII (568 bp). The 3' fragment was obtained through restriction enzyme digestion of the pEFBOS-ANC_2H01E plasmid with HindIII and PstI (1320 bp). These two fragments were ligated into the BglII/PstI-digested pEGFP-C1 plasmid. The resulting plasmid was called pEGFP-C1-ANC_2H01FL.

A truncated fragment of ANC_2H01, coding for a protein lacking amino acid residues 1 to 25, was likewise cloned into the pEGFP-C1 vector using two fragments. The 5' fragment (484 bp) was obtained through restriction enzyme digestion of the pGAD10ANC_2H01/BamHI plasmid with BamHI and HindIII. The 3' fragment (977 bp) was obtained through restriction enzyme digestion of the pGAD424ANC_2H01FL plasmid with HindIII and PstI. These two fragments were ligated to the BglII/PstI-digested pEGFP-C1 plasmid. The resulting plasmid was called pEGFP-C1-ANC_2H01ΔNLS.

The in-frame cloning and the insertion of the correct fragments were confirmed by DNA sequence analysis, using the vector-specific primers FVR1474R and FVR1467F (Table 11) and the ANC_2H01-specific primer FVR274F (Table 1) for each of the constructed plasmids.

Construction of Full-length ANC_2H01 or αN-catenin, Each Fused to Mitochondrial Membrane Anchor Sequences The ANC_2H01 cDNA was fused to a mitochondrial membrane anchor in two steps. In the first step, the full-length ANC_2H01 cDNA was cloned in the pcDNA3 vector (Invitrogen Corporation, Carlsbad, Calif.) as two restriction enzyme fragments. The 5' fragment (618 bp) was obtained by restriction enzyme digestion of the plasmid pEFBOSANC_2H01E with BamHI and HindIII. The 3' fragment (908 bp) was obtained by restriction enzyme digestion of the plasmid pDNAANC_2H01E with HindIII and NotI. These two fragments were ligated into the BamHI/NotI digested pcDNA3 vector. The resulting vector was called pcDNA3-ANC_2H01E. In the second step, the mitochondrial membrane anchor was cloned into the pcDNA3-ANC_2H01E plasmid. The mitochondrial membrane anchor originated from *Listeria monocytogenes* (Bubeck et al., 1997), and was provided on a plasmid called lppNT/ActaNt-Mito/pUHD (a gift from Dr. M. Petit, Centrum voor Menselijke Erfelijkheid, KULeuven, VIB-4). It was specifically PCR-amplified using the forward primer 5'-ATCGTACTCGAGCCCCGGGGGAAC-3' (=FVR1844F, Table 12) (SEQ ID NO: 120) and the reverse primer 5'-AGCCTCTGGGCCCATCACAACAGG-3' (=FVR1845R, Table 12) (SEQ ID NO: 121), containing, respectively, an XhoI and an ApaI restriction site. This yielded a product of 243 bp. The XhoI/ApaI-digested PCR fragment was subsequently ligated into the XhoI/ApaI-digested pcDNA3-ANC_2H01E plasmid. The resulting plasmid was called pcDNA3-ANC_2H01E-MAS.

The αN-catenin was likewise fused in frame with the mitochondrial membrane anchor by use of two restriction enzyme fragments. The 5' fragment (2150 bp) was obtained by restriction enzyme digestion of the plasmid pPNhαNCTN with EcoRI and EcoRV. The 3' fragment (741 bp) was a restriction enzyme digested PCR-amplified product using the forward primer 5'-ATCATTGTACTGGCCAAGCAGATG-3' (=FVR1872F, Table 12) (SEQ ID NO: 122) and the reverse primer 5'-GTCCTACTCGAGGAAGGAATCCATT-3' (=FVR1873R, Table 12) SEQ ID NO: 123), containing, respectively, an EcoRV and an XhoI restriction site. These two fragments were ligated to the EcoRI/XhoI-digested pcDNA3-ANC_2H01E-MAS vector fragment (5,607 bp). The resulting plasmid was called pcDNA3-αNCTN-MAS.

The in-frame cloning and the insertion of the fragments were confirmed by DNA sequence analysis, using the vector-specific primers FVR63F and FVR736R (Table 10) and the αN-catenin-specific primers FVR1479F and FVR1248F (Table 6) or the ANC_2H01-specific primers FVR274F and FVR310R (Table 1).

Figure 23:
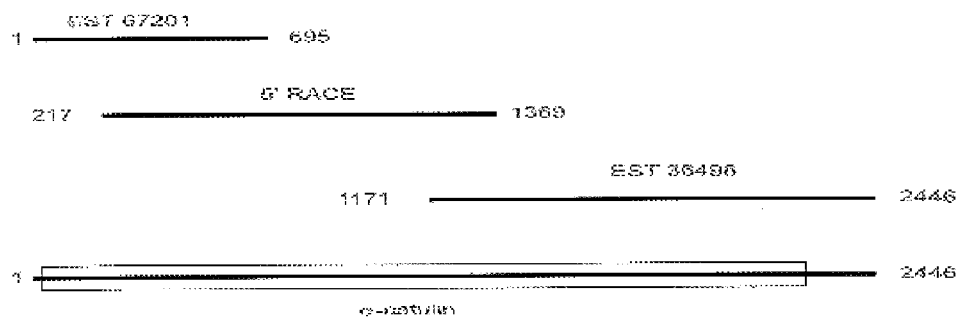
FIG. 23. The full-length α-catulin cDNA sequence was built from 3 clones: the 5' EST clone 67201, a 5' RACE product and the EST clone 36498. The open reading frame (bases 44 to 2248) is boxed.

Construction of a Plasmid Encoding the Full-length Alpha-catulin Fused to the GAL4-DBD The full-length α-catulin (αct1) cDNA sequence (Genbank Accession number U97067) was isolated by us in 3 steps (see FIG. 23). First, we identified some EST sequences of which clone 36498 contains the largest insert (1284 bp), showing homology but not identity to other α-catenin sequences. By a 5' Marathon™ RACE (Clontech, Palo Alto, Calif., U.S.A.) experiment this sequence was extended towards the 5' end with 1152 bp more nucleotides. The RACE product was obtained with primer FVR 415 (5'-TCCCAGATATGTGTCGTAACAATCG-3') (SEQ ID NO: 153) and with nested primer FVR 416 (5'-GGCCAGTCACCTGAAATGTC-3') (SEQ ID NO: 154) on human mammary gland cDNA. Finally, the sequence of this RACE product was overlapping at the 5' side with the EST clone 67201 (695 bp), providing the start of the open reading frame.

In order to obtain a clone with this full-length sequence, these 3 clones were assembled in the pGEM11 vector (Clontech). First, the EST67201 insert was isolated by a SmaI-MunI digest and ligated into the SmaI-MunI opened vector pGEMT-αct1RACE. In this way, the construct pGEMT-αct1(1-1369) was obtained. Part of the EST36498 sequence (1,003 bp) was obtained by a BglII restriction digest yielding the complete 3' part of the open reading frame but only part of the 3' untranslated region. This fragment was inserted in the previous construct pGEMT-αct1(1–1369), opened with BglII. This resulted in a clone containing the complete open reading frame of α-catulin: pGEMT-αct1(1–2264).

Figure 24:
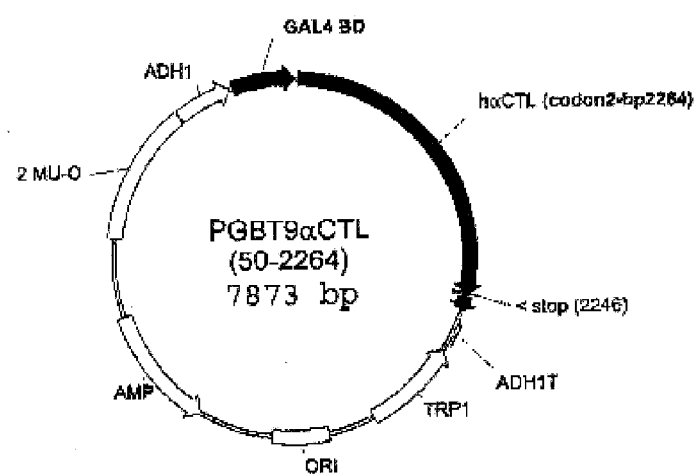
FIG. 24. The pGBT9-αctl(50-2264) clone, used as bait plasmid in a two-hybrid screening.

This clone was used as a template to generate a PCR product with primers FVR711 (5'-AGGGGGCAGTGGCTGAAGAAAGAAGATATC-3') (SEQ ID NO: 155) (containing an EcoRV site) and FVR725 (5'-TATTAGATATCGCCTCTCCCGGACCCGCC-3') (SEQ ID NO: 156). In a 3-points ligation this PCR product, cut with EcoRV +MunI, was ligated together with a MunI-SalI fragment of pGEMT-αct1(1–2264) into the BamHI (blunted)-SalI restricted two-hybrid vector pGBT9 (Clontech), in frame with the GAL4 DNA-binding domain. The obtained constructed was called pGBT9-αct1(50–2264) (FIG. 24). All clones were checked by DNA sequence analysis.

Construction of Eukaryotic Expression Plasmids Encoding Parts of α-catulin or Brx A construct was made for eukaryotic expression of α-catulin, in frame with a C-terminal E-tag. The eukaryotic expression vector pES31 was constructed by Dr. Nico Mertens (Department of Molecular Biology, University of Ghent), by combining the pcDNA3 (Invitrogen, Groningen, The Netherlands) and pCAGGS (Niwa et al., 1991) vectors, adding to this a Bcl1-IgMKL signal sequence followed by a Eco47III restriction site. A PCR product of human α-catulin was obtained with primers NM 120 (5'-AGCGCTGCATCTCCAGGACCCGCCGGCGTTG-3' (SEQ. I.D. NO. 130), introducing an Eco47III site at position 47 of the cDNA) and NM121 (5'-CGCGGATCCTTATCCGGAAGTTTTACTATCCATAGTGTGC-3' (SEQ. I.D. NO. 131), introducing a BspEI site at position 2247 of the cDNA), using the construct pGEMT-αct1 (1–2264) as a template. This PCR product was digested with Eco47III and BspEI and inserted in the prokaryotic expression vector pLX32HE, restricted with the same enzymes (vector and construct made by Dr. Nico Mertens). This yielded plasmid pLX32H-αct1-E (sequence in FIG. 28) (SEQ. I.D. NO. 133). From this construct, the insert including the C-terminal E-tag was excised with the restriction enzymes Eco47III and KpnI, and ligated in the NcoI and KpnI sites of the pES31 vector, of which the NcoI site was completely filled in with T4 polymerase. Thus the construct pES31-αct1(47–2247)-E was obtained, encoding amino acid residues 2–735 of the human α-catulin fused to the E-tag, predicted to encode a protein of 83.5 kDa (sequence in FIG. 29) (SEQ. I.D. NO. 134).

The construct pCS2MT-Brx(3003–3641) was obtained from the original two-hybrid plasmid, pGADGH-Brx (3003–3641) by excising the insert with EcoRI and XhoI and inserting it in the eukaryotic expression vector pCS2MT (Roth et al., 1991), restricted with the same enzymes. pCS2MT-Brx(3003–3641) encodes a 34-kDa fusion protein of 6 consecutive aminoterminal Myc epitope tags (9 kDa) and part of the Brx protein (predicted MW of 25 kDa).

The construct pBK-RSV-Brx (142–4290), encoding human Brx amino acid residues 47–1428 with an aminoterminal Flag-tag (predicted MW 150 kDa), was kindly provided by Dr. James Segars (Rubino et al., 1998).

Yeast Strains and Media

The *Saccharomyces cerevisiae* strain HF7c (Mata, ura3-52, his3-Δ200, ade2-101, lys2-801, trp1-901, leu2-3, 112, gal4-542, gal80-538, lys2::GAL1-HIS3, URA3::GAL4 17-mers)-CYC1-LacZ) (Matchmaker™, Clontech, Palo Alto, Calif.) was used for most assays. The HF7c yeast strain carries two reporter genes, HIS3 and LacZ, both integrated into the yeast genome and under the control of GAL4 responsive elements, respectively, the GAL1 UAS and the $UAS_{G-17mer}$. It has also two auxotrophic markers, trp1 and leu2, which are used for plasmid selection upon transformation. Yeast cultures were grown at 30° C. in either complete YPD medium (1% yeast extract, 2% peptone and 2% glucose) or in SD minimal medium (0.5% yeast nitrogen base without amino acids, 2% glucose, and 1% of the appropriate amino acid drop out solution).

The *Saccharomyces cerevisiae* strain Y190 (Mata, ura3-52, his3-200, ade2-101, lys2-801, trp1-901, leu2-3, 112, gal4Δ, gal80Δ, $cyh^{539}2$, LYS2::$GAL1_{UAS}$-$HIS3_{TATA}$-HIS3, URA::$GAL1_{UAS}$-$GAL1_{TATA}$-lacZ) (Matchmaker™, Clontech, Palo Alto, Calif.) was used to perform control experiments. The Y190 strain exhibits a significant level of constitutive leaky expression of the HIS3 reporter gene. This background can be repressed by including 40 mM 3-aminotriazole (3-AT) in the medium. This strain also contains an integrated LacZ reporter gene under the control of the GAL4 responsive elements in the GAL1 UAS and GAL1 minimal promoter. This results in a high level of LacZ expression when induced by a positive two-hybrid interaction. In vivo assay on agar plates can be performed with this strain, unlike strain HF7c for which colony transfer to filters is needed (see below).

Yeast Transformation and β-galactosidase Filter Assay

Plasmids encoding the GAL4 hybrid proteins were introduced into the HF7c yeast reporter strain by the lithium acetate (LiAc) transformation procedure (Gietz et al., 1992, MATCHMAKER Yeast protocol Handbook). Transformants were selected for the presence of the plasmids by growing on appropriate media at 30° C. They were allowed to grow until the colonies were large enough to perform a β-galactosidase filter assay, usually 3–4 days. The transformed cells were then transferred onto a 82-mm nitrocellulose membrane (Sartorius, Goettingen, Germany), permeabilized by freezing the membranes in liquid nitrogen for one minute and followed by thawing at room temperature. The membranes are soaked with 1.5 ml of Z-buffer containing 5-bromo-4-chloro-3-indolyl-β-D-galactosidase (X-gal) and incubated at 30° C. until the appearance of blue colonies. This takes usually 30 min to 12 hours. The membranes are then dried, analyzed and stored.

Using the Y190 strain, the β-galactosidase assay was done in vivo, on agar plates containing SD minimal medium lacking Trp, Leu and His (1,5% agar, 0.5% yeast nitrogen base without amino acids, 2% glucose, and 1% of the appropriate amino acid drop out solution), completed with 0.07 M potassium phosphate pH=7, 40 mM 3-AT and X-gal (80 mg/ml).

Two-hybrid cDNA Library Screening and DNA Sequence Analysis

The plasmid pAS2ANCTN was used to screen a human kidney cDNA library, cloned in the GAL4 activation domain vector pGAD10 (Clontech, Palo Alto, Calif.). The plasmids were introduced into the HF7c yeast strain by using sequential transformation by the lithium acetate (LiAc) method described by Gietz et al. (1992) The interaction screen was carried out in the yeast strain HF7c on media lacking leucine, tryptophan, histidine, and containing 5 mM 3-aminotriazole (3-AT). The β-galactosidase activity in yeast was measured using a β-galactosidase filter assay.

Yeasts harboring interacting proteins were used for plasmid isolation. The obtained plasmid mixture was transformed into *Escherichia coli* HB101 electrocompetent cells. HB101 has a defect in the leuB gene which can be complemented by LEU2 from yeast. So, this strain can be used for selection of the library plasmid, which carries the yeast LEU2 transformation marker. From these transformants, the library plasmids were isolated and introduced into *Escherichia coli* DH5α. Plasmids isolated from this strain were further characterized by DNA sequence. This was done by the dideoxy chain termination method (Sanger, 1981) using fluorescent dye terminators in a 373A or a 377 automated DNA sequencer (Applied Biosystems, Foster City, Calif.). The sequences were further analyzed by BLAST search (Altschul et al., 1990) and the DNAstar software packages (DNASTAR Inc, Madison, USA), and by the Staden gap4 software (Bonfield et al., 1995). To sequence the cDNA insert of the library plasmid, two primers were designed on the pGAD10 vector sequence flanking the cDNA insert: a forward primer 5'-ACCACTACAATGGATGATGT-3' (=FVR174F; Table 2) (SEQ. I.D. NO. 56) and a reverse primer 5'-TAAAA-GAAGGCAAAACGATG-3' (=FVR192R; Table 2) (SEQ. I.D. NO. 58).

Two-hybrid cDNA Library Screening with a Full-length α-catulin bait

Figure 25:
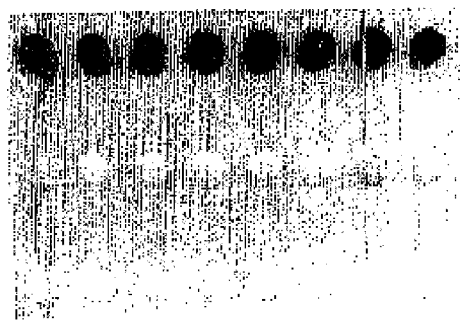
FIG. 25. Confirmation of the specific interaction between full-length α-catulin (plasmid) pGBT9-α- ctl) and a fragment of Brx/proto-Lbc (plasmid pGADGH_ACTL2H_K_E2) by cotransformation in the yeast strain Y190. Bait plasmids pVA3 and pGBT9 served as negative controls.

Plasmid pGBT9-αct1(50–2264) was used for a two-hybrid screening of a human HeLa prey library cloned in the pGADGH vector (Clontech), as described above in Materials and Methods, but using the yeast strain Y190. Clones obtained by growth on −LTH selective plates containing 40 mM 3AT were checked for β-galactosidase activity. From positive clones, yeast DNA was isolated and transformed by electroporation into the KC8 bacterial strain. This strains contains a defect in the LeuB gene, allowing selection for presence of a pGADGH library plasmid. Isolated pGADGH clones were checked for the presence of inserts by HindIII restriction digest and retransformed into Y190 yeast cells, in combination with either the pGBT9-αct1(50–2264) plasmid or the pVA3 and pGBT9 plasmids, the latter serving as negative controls for auto-activation. A positive clone ACTL2H_K_E2 showing specific interaction (FIG. 25) was then further characterized by sequence analysis as described, after introduction into the E. coli DH5α strain. The obtained sequences were analyzed by BLAST (Altschul et al., 1990) and by the DNAstar software packages (DNASTAR Inc, Madison, U.S.A.).

Northern Blot Analysis

The total length of the complete mRNA encoding the zinc finger protein was estimated by Northern blot analysis. Total mRNA of various human cell lines was isolated by using RNA-zol B (Wak Chemie-Medical, Bad Homburg, Germany). Total mRNA (15 μg) was glyoxylated, size fractioned on a 1% agarose gel and transferred to a Hybond-N+ membrane (Amersham). The probe was radioactively labeled using random priming (RadPrime DNA labeling system; Gibco BRL Life Technologies, Gent, Belgium). The probe used was a 700-bp BamHI fragment of the isolated two-hybrid clone ANC_2H01, and covered the amino-terminal part and two of the 9 zinc fingers. Hybridizations were performed as described elsewhere (Bussemakers et al., 1991).

Mutliple Tissue RNA Dot Blot Analysis

A human RNA Master Blot™ was purchased from Clontech and hybridized according to the manufacturer's instructions. The probe was a 700-bp BamHI restriction fragment of the originally isolated two-hybrid clone ANC_2H01. The labeling was executed by use of the Strip-EZ™ DNA labeling kit (Ambion). Hybridization conditions were as described for the Northern blot analysis. The ExpressHyb™ hybridization solution was purchased from Clontech. The blot was exposed for 7 days to a P-imager screen (Molecular Dynamics).

RT-PCR

For RT-PCR, cDNA was synthesized in a 20 ml reaction containing 200 U Superscript™ II RNase H-reverse transcriptase (Gibco-BRL Life Biotechnologies), 50 mM Tris HCl (pH 8.3), 75 mM KCl, 3mM MgCl2, 10 mM DTT, 0.5 mM dXTPs, 20 U RNase block I (Stratagene, La Jolla, Calif.), and 220 pmol oligo-dT or random hexamers. The reaction was performed at 37° C. during 1 h, followed by a 6 min incubation at 90° C. to inactivate enzymes. The cDNA was then incubated for 20 min with 2 U RNase H (Gibco-BRL Life Biotechnologies). Subsequently, a PCR reaction was performed by using ANC_2H01-specific primers. The standard PCR mixture contained 1 ml template cDNA, 25 pmol of the ANC_2H01-specific primers, 200 mM dXTPs and the buffer supplied with the AmpliTaq Gold DNA polymerase (Perkin Elmer Cetus). The PTC-200 Peltier Thermal Cycler PCR System (MJ Research, Watertown, Mass.) was used. Cycling conditions were 94° C. for 10 min, 94° C. for 30 sec, 55–65° C. for 30 sec and 72° C. for 1 min. This was repeated for a total of 38-40 cycles and followed by a final extension step of 10 min at 72° C. A set of ANC_2H01-specific primers was used (FVR1686F/FVR1687R; Table 10) to amplify a 309-bp fragment. A PCR using GAPDH-specific primers (FVR1986F and FVR1987R; Table 13) was performed as a positive control.

To look for the expression of αN-catenin in the cell lines examined, we performed an RT-PCR using the αN-catenin-specific primers (FVR 1762F and FVRI 826R; Table 13).

Western Blot Analysis

Cells were lysed by boiling in sample buffer in the presence of 5% β-mercaptoethanol (Laemmli, 1970). The proteins were fractionated by SDS-PAGE and transferred to an Immobilon-P membrane (Millipore, Bedford, Mass.). The blot was then blocked with 5% nonfat dry milk in PBS$^A$ containing 0.01% Tween-20. This was followed by an incubation with the primary antibody for 3 h and after extensive washing, an alkaline phosphatase-conjugated secondary antibody was added for again a 3-hour incubation. Finally, the substrate NBT/BCIP (nitroblue tetrazolium plus 5-bromo-4-chloro-3-indolyl phosphate) for the secondary antibody was then applied to visualize the specific proteins on the membrane. The staining reaction was stopped by rinsing the blot with water.

Alternatively, a horseradish-peroxidase-conjugated secondary antibody was used for an incubation of at least 1 hour. The specific proteins were detected by chemiluminescence with the ECL Western blot detection reagents (Amersham Pharmacia, UK).

Antibodies

The following antibodies were used in Western blot and immunocytochemistry experiments. The monoclonal antibody directed against the E-tag was purchased from Pharmacia and was used in a 1/300 dilution for Western blot analysis and a 1/1000 dilution for immunocytochemistry. The secondary antibody used for Western blot analysis was the anti-mouse alkaline phosphatase-conjugated antibody (dilution 1/500; Sigma Chemical Company, St Louis), or the anti-mouse horseradish-peroxidase-conjugated antibody (dilution 1/3,000; Amersham Pharmacia Biotech, UK). We used an anti-mouse Cy5-conjugated antibody as a secondary antibody for immunostaining (dilution 1/200, Amersham Pharmacia Biotech, UK), or the anti-mouse Alexa594-conjugated antibody (dilution 1/300; Molecular Probes, Oregon).

The polyclonal antibody directed against αN-catenin was purchased from Santa Cruz Biotechnology and used for Western blot analysis (dilution 1/100) as well as for immunocytochemistry (dilution 1/200, Santa Cruz Biotechnology, Inc., California). The secondary antibody applied in Western blot analysis was the anti-goat alkaline phophatase-conjugated antibody (dilution 1/7500, Sigma Chemical Company, St Louis), or the anti-goat horseradish-peroxidase-conjugated antibody (dilution 1/80,000; Sigma Chemical Company, St Louis). For immunocytochemistry, we used the anti-goat FITC-conjugated antibody (dilution 1/75, Chemicon International Inc., Temecula, Calif.).

The polyclonal antibody directed against human and mouse αE-catenin was used for Western blot analysis (dilution 1/4000, Sigma Chemical Company, St Louis). The secondary antibody used was the anti-rabbit alkaline phosphatase-conjugated antibody (dilution 1/5000, Sigma), or the anti-rabbit horseradish-peroxidase-conjugated antibody (dilution 1/3,000; Amersham Pharmacia Biotech, UK). For immunocytochemistry, we used the anti-rabbit FITC-conjugated antibody (dilution 1/100; Southern Biotechnology Associates, Birmingham).

To detect E-cadherin in HEK293T cells by Western blot analysis, we applied the mouse HECD1 anti-E-cadherin monoclonal antibody from Zymed (dilution 1/250, Zymed Laboratories, Inc., San Francisco, Calif.) followed by the secondary anti-mouse alkaline phophatase-conjugated antibody (dilution 1/5000, Sigma).

The anti-Pan-cadherin antibody (dilution 1/500, Sigma), recognizing at least E-cadherin, N-cadherin, P-cadherin, VE-cadherin, R-cadherin and T-cadherin, was also used in Western blot analysis. The secondary antibody used was the anti-rat alkaline phosphatase-conjugated antibody (dilution 1/5000, Sigma).

For the detection of the GAL4 DNA binding domain fusion proteins, a rabbit anti-GAL4 DNA binding domain antiserum was applied (dilution 1/1000; UBI). For the detection of the GAL4 activation domain fusion proteins, a rabbit anti-GAL4 activation domain antiserum was used (dilution 1/1000, UBI). The secondary antibody used in Western blot analysis was anti-rabbit alkaline phosphatase-conjugated antibody (dilution 1/5000, Sigma).

The monoclonal antibody M3 directed against the Flag-tag (Santa Cruz Biotech, Santa Cruz, Calif.) was used in a dilution of 1/2,000 for Western blotting. The monoclonal antibody 9E10 directed against the Myc-tag (Oncogene, Cambridge, UK) was used in a dilution of 1/1,000 for Western blotting. The secondary antibody used was the anti-mouse HRP-coupled antibody (dilution 1/3,000, Sigma Chemical Company, St Louis). Detection on Western blot was performed with the ECL system (Amersham Pharmacia Biotech, UK).

5'RACE

In order to complete the cDNA of the clone isolated by the two-hybrid screen, we used 5' RACE technology (GIBCO BRL, Life Technologies, Gent, Belgium). The lacking 5' fragment was isolated using a gene specific primer 5'-GCGGTTCTTCATCAGTTTGG-3' (GSP1=FVR359R; Table 1) (SEQ. I.D. NO. 21) to synthesize the first strand of the cDNA. We performed a PCR with the primer set GSP2 5'-CTCTTGGGTTTGCTGGTTGA-3' (=FVR360R; Table 1) (SEQ. I.D. NO. 22) and anchor primer 5'-GAATTCG-TCGACTAGTACGGGIIGGGIIGGGIIG-3' (=FVR239F; Table 3) (SEQ. I.D. NO. 60), followed by a nested PCR with the gene specific primer GSP2 (=FVR360R; Table 1) and primer UAP 5'-GAATTCGTCGACTAGTAC-3' (=FVR240F; Table 3) (SEQ. I.D. NO. 61). This yielded 3 fragments from human mammary gland mRNA and 2 from human uterus mRNA. No fragments could be amplified from human fetal brain mRNA or human small intestine mRNA. The fragments were further characterized by cloning into pGEM®-T cloning system (Promega, Madison, Wis.) and by subsequent DNA sequence analysis using the M13 forward (5'-CGCCAGGGTTTTCCCAGTCACGAC-3'; FVR283; Table 5) (SEQ. I.D. NO. 64) and M13 reverse primer (5'-TCACACAGGAAACAGCTATGAC-3'; FVR284; Table 5) (SEQ. I.D. NO. 65). The specificity of the fragments was determined using the DNAstar software packages (DNASTAR Inc, Madison, USA), and by the Staden gap4 software (Bonfield et al., 1995). The RNA from normal tissue was purchased from Clontech (Clontech, Palo Alto, Calif.).

Transfection Procedure of HEK293T Cells

HEK293T cells (Graham et al., 1977; Wigler et al., 1978) were transiently transfected with the pPNhANCTN and/or the pEFBOSANC_2H01E plasmid by a $Ca_3(PO_4)_2$ transfection procedure. The cultured HEK293T cells were trypsinized and reseeded at 300.000 cells/ml 24 h before transfection. Two hours before transfection, fresh medium was added to the cells. For a 6-well plate, 2 μg of plasmid DNA per well was used, while for a culture flask of 25 $cm^2$ 5 μg of plasmid DNA was applied. The sterile, ethanol precipitated plasmid DNA (purified on a Qiagen DNA purification column, Qiagen Inc., Calif., USA) was dissolved in 0.1×TE (Tris-EDTA) buffer, pH 7.5. The appropriate amount of plasmid DNA was mixed with an equal volume of a mixture comprising 1 volume 125 mM $CaCl_2$/HEPES, pH 7.05 and 4 volumes 0.1×TE. The DNA mixture was added very slowly to 1×HEPES/2×BS (buffered saline). Upon shaking mildly, the DNA-$Ca_3(PO_4)_2$ precipitate was formed and could then be added to the medium covering the cells. The incubation of the cells was done at 37° C. for 24 h. The DNA-transfection mixture was then removed and replaced by fresh medium consisting DMEM, supplemented with 10% FCS, 0.03% glutamine, 100 U/ml penicillin, 100 mg/l streptomycin and 0.4 mM sodium pyruvate.

Immunocytochemistry

HEK293T cells were reseeded and grown on glass coverslips and transfected with either the plasmid encoding αN-catenin, or with the plasmid encoding the E-tagged ANC_2H01 protein or with both plasmids. The cells were incubated according to the transfection protocol. When confluent monolayers were formed, cells were fixed with ice-cold methanol for 15 min at −20° C. The cells were washed with PBSA. Subsequently, the cells were incubated for 1 h at 37° C. with either a polyclonal antibody against αN-catenin (goat anti-αN-catenin, Santa Cruz Biotechnology), or an antibody against the E-tag (Pharmacia) or both. After extensive washing with $PBS_A$, the appropriate FITC- or Cy5-labeled secondary antibodies were applied for 1 h at 37° C. All antibodies applied were diluted in $PBS_A$ containing 0.04% gelatin. Finally, coverslips with cells were mounted with Vectashield (Vector Laboratories, Burlingame, Calif.). The cells were examined with a Zeiss LSM 410 confocal laser-scanning immunofluorescence microscope (Carl Zeiss, Jena, Germany).

Raising of Polyclonal and Monoclonal Antibodies Against ANC_2H01

We are raising a polyclonal antibody against the ANC_2H01 protein by immunization of rabbits with a ANC_2H01-specific synthetic peptide, that was synthesized and purified by the VIB-Department of Medical Protein Chemistry. This peptide corresponds to the aa residues 73–87 (sequence $NH_2$-DGIKARNRNQNYLVP-COOH) (SEQ ID NO: 158) and was chosen on the basis of the Protean program of the DNAstar software packages (DNASTAR Inc, Madison, USA). The peptide was extended with an additional cysteine residue at the carboxyterminus. Via this cysteine residue, the peptide was conjugated to keyhole limpet hemocyanin (KHL, Sigma). Three rabbits were each immunized with 200 μg peptide, mixed with Titermax (Sigma Chemical Company, St Louis, Mo.).

Figure 13:
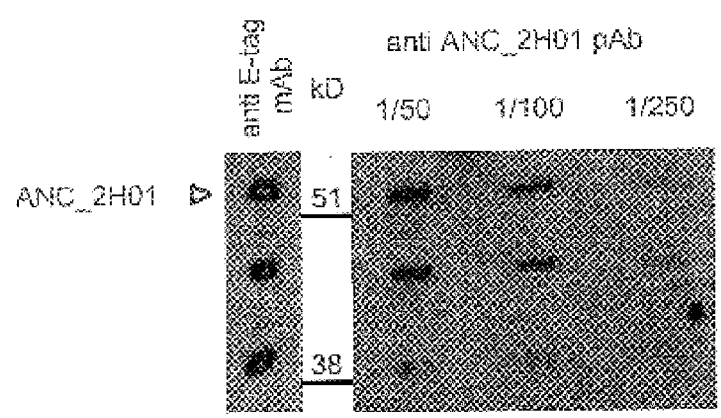
FIG. 13. Detection of ANC_2H01 protein by use of the anti-ANC_2H01 polyclonal antibody at three different dilutions. HEK293T cells were transfected with the pEFBOSANC_2H01 E plasmid and lysates were analysed by Western blot analysis. A development with anti-E-tag antibody is shown at the left and serves as a positive control.

After two and four weeks, the rabbits were boosted with the peptide mixed again with Titermax (Sigma Chemical Company, St Louis, Mo.). Six weeks later, serum was tested by ELISA. Western blot experiments were done to test the antigen specificity of the antibody (FIG. 13). Subsequently, the ANC_2H01-specific antibodies were affinity-purified. About 2 mg peptide was coupled to 1 ml p-hydroxymercuribenzoate (Sigma Chemical Company, St Louis, Mo.) in 20 mM Tris, pH 8.0. After washing (0.5 M NaCl, 10 mM Tris pH 7.5), elution was done with 100 mM glycine, pH 2.5 followed by a neutralizing step (1 mM Tris, pH 8.0).

Monoclonal antibodies will be generated against a KHL-coupled peptide. The peptide was used to generate polyclonal antibodies and corresponds to the aa residues 73–87 (sequence NH$_2$-DGIKARNRNQNYLVP-COOH) (SEQ ID NO: 156). Three mice were each immunized with 50 mg peptide mixed with Titermax (Sigma Chemical Company, St Louis, Mo.).

PAC Screening

The isolation of a human genomic DNA clone comprising the ANC_2H01gene was done by PCR screening of a PAC clone library RPCI1 (Ioannou and de Jong, 1996). Pools of human PAC library clones were obtained from the UK HGMP Resource Center (Hinxton, Cambridge, UK) and were screened by PCR, using primers FVR513F (Table 1) and FVR514R (Table 1). A 338-bp PCR fragment was amplified on ANC_2H01 cDNA. Out of these pools of human PAC library clones, one positive clone was identified and an aliquot of this clone was streaked out on a LB-agar plate containing kanamycin and single colonies were re-examined by PCR. A positive colony was then grown and used for DNA isolation.

Fluorescence In Situ Hybridization Analysis (FISH)

FISH analysis using PAC clone 167O24 specific for the ANC_2H01 gene was performed according to standard procedures (Kievits et al., 1990) with some minor modifications. The DNA of the PAC clone was biotinylated using a BioNick-kit (Gibco BRL) according to the manufacturer's protocol. Fluorescence image results were captured by a Photometrics Image Point CCD camera (Photometrics-GmbH, Munchen, Germany) mounted on a Zeiss Axiophot microscope (Carl Zeiss, Jena, Germany). Image processing was performed and chromosome G-banding was obtained by reverse DAPI-banding using the MacProbe v3.4.1 software (Perceptive Scientific International LTD., League City, Tex., USA).

CASTing

CASTing (Cyclic Amplification and Selection of Target sequences (Wright et al., 1991) is used to determine any DNA sequences to which the ANC2H01 protein binds specifically. The first step is the construction of a plasmid to obtain the protein of interest fused to GST. Using this GST-part, the protein can be immobilized on a gluthatione column. We have cloned the zinc finger domain of ANC_2H01 into the pGEX4T vector (Pharmacia).

Coimmunoprecipitation

HEK293T cells were transiently cotransfected with either the pPNhαNCTN and pEFBOSANC_2H01E plasmids or with the pJ6αECTN and pEFBOSANC_2H01E plasmids. After 48 h, cells were lysed in a buffer containing 50 mM Tris-HCl (pH 7.4), 150 mM NaCl, 0.5% NP-40, 200 µM ZnCl$_2$, 10 mM DTT (supplemented with the protease inhibitors aprotinin, leupeptin, Pefablok, and the phosphatase inhibitors NaF, Na$_3$VO$_4$, β-glycerophosphate). Lysates were cleared in a microfuge for 8 min. Protein concentration was determined using the Bio-Rad D$_c$ Protein Assay (Bio-Rad Laboratories, Hercules, Calif.). Amounts of 400 µg protein were incubated for three h with 4 µg anti-E-tag, anti-αN-catenin or anti-αE-catenin antibodies or without antibody. Immune complexes were precipitated for one h by the addition of a 50-µl 50% Protein-G-Sepharose slurry (Amersham Pharmacia Biotech, UK), followed by four wash steps with lysis buffer. The affinity gel was resuspended in 50 µl SDS-containing sample buffer, and boiled for 5 min. Proteins were fractionated by SDS-PAGE, and evaluated in a Western blot experiment.

RESULTS

Example 1:

The ANC-2H01 Protein Interacting with αN-Catenin

Two-hybrid cDNA Library Screening

For the initial two-hybrid screen, almost the full-length αN-catenin cDNA was fused to the GAL4 DNA binding domain in the pAS2 vector (Clontech) and assayed for interaction with proteins encoded by a GAL4 activation domain cDNA library from human kidney (Clontech). About 3×10$^5$ clones were screened and examined for interaction with αN-catenin on the basis of induction of two genes: the selection gene HIS3 and the reporter gene LacZ. One clone, that exhibited the desired HIS3-positive, β-galactosidase-positive phenotype, was isolated out of this screen and was further examined. The clone contained an insert of about 2,500-bp (FIG. 2). The cDNA insert of the clone was completely sequenced using universal and specific walking primers (see Table 1). The cDNA insert revealed an open reading frame (ORF) of 459 amino acids. The insert contained a stop codon, a poly-A signal, a poly-A tail, but no start codon could be detected. Analysis of the encoded protein revealed the presence of 9 Cys$_2$His$_2$ zinc fingers at the carboxy-terminal half of the protein (FIGS. 1 to 3). Zinc fingers of the Cys$_2$His$_2$-type, originally discovered in TFIIIA (Hanas et al., 1983a+1983b; Miller et al., 1985), often function in nucleic acid binding and, more particularly, in sequence specific recognition of DNA, which is pivotal for the function of transcription factors. The 3' untranslated region (UTR) contained an Alu repeat region of 286 nucleotides (FIGS. 1 and 2). The two-hybrid clone isolated in this screen was called ANC_2H01 (for Alpha-N-catenin 2-hybrid clone 01).

Coimmunoprecipitation

Figure 14:
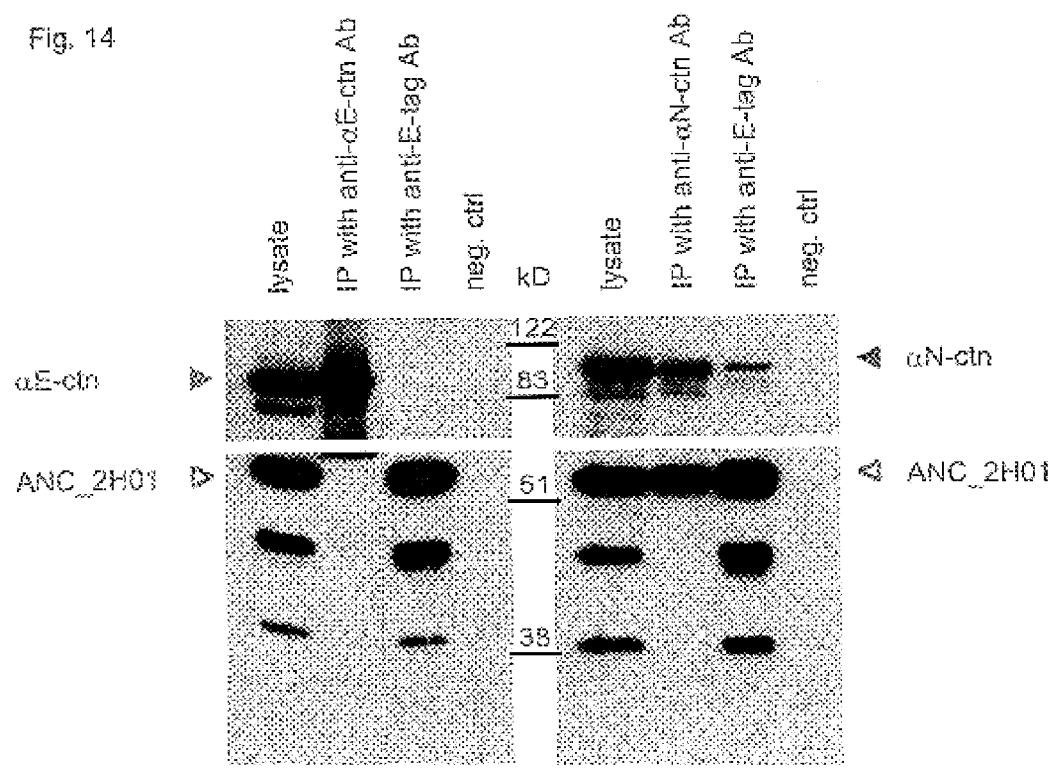
FIG. 14. Co-immunoprecipitation of E-tagged ANC_2H01 with αN-catenin, but not with αE-catenin in HEK293T cells transiently transfected with the plasmids pJ6αECTN and pEFBOSANC_2H01E (left panel) or pPNhαNCTN and pEFBOSANC_2H01E (right panel). The specific antibodies (Ab) used for the immunoprecipitation are shown on top of the boxes. After PAGE, the gel was blotted. This blot was cut in two parts. The lower part (proteins with approximate molecular weight <60kDa) was probed with anti-E-tag antibody. The upper left part (proteins >60 kDa) was probed with the anti-α-catenin antibody (Sigma). The upper right part (proteins >60 kDa) was probed with the anti-αN-catenin antibody (Santa Cruz).

The specific interaction between ANC_2H01 and αN-catenin was confirmed in a coimmunoprecipitation experiment. HEK293T cells were transiently cotransfected with the pEFBOSANC_2H01 plasmid and either the pPNhαNCTN or pJ6αECTN plasmid. αN-catenin could be coimmunoprecipitated with ANC_2H01, using the anti-E-tag antibody, and ANC_2H01 could be coimmunoprecipitated with αN-catenin, using the anti-αN-catenin antibody (FIG. 14). Furthermore, αE-catenin could not coimmunoprecipitate ANC_2H01, using the anti-α-catenin antibody, and could not be coimmunoprecipitated by ANC_2H01, using the E-tag antibody.

Mitochondrial Targeting of αN-catenin and ANC_2H01

Figure 15:
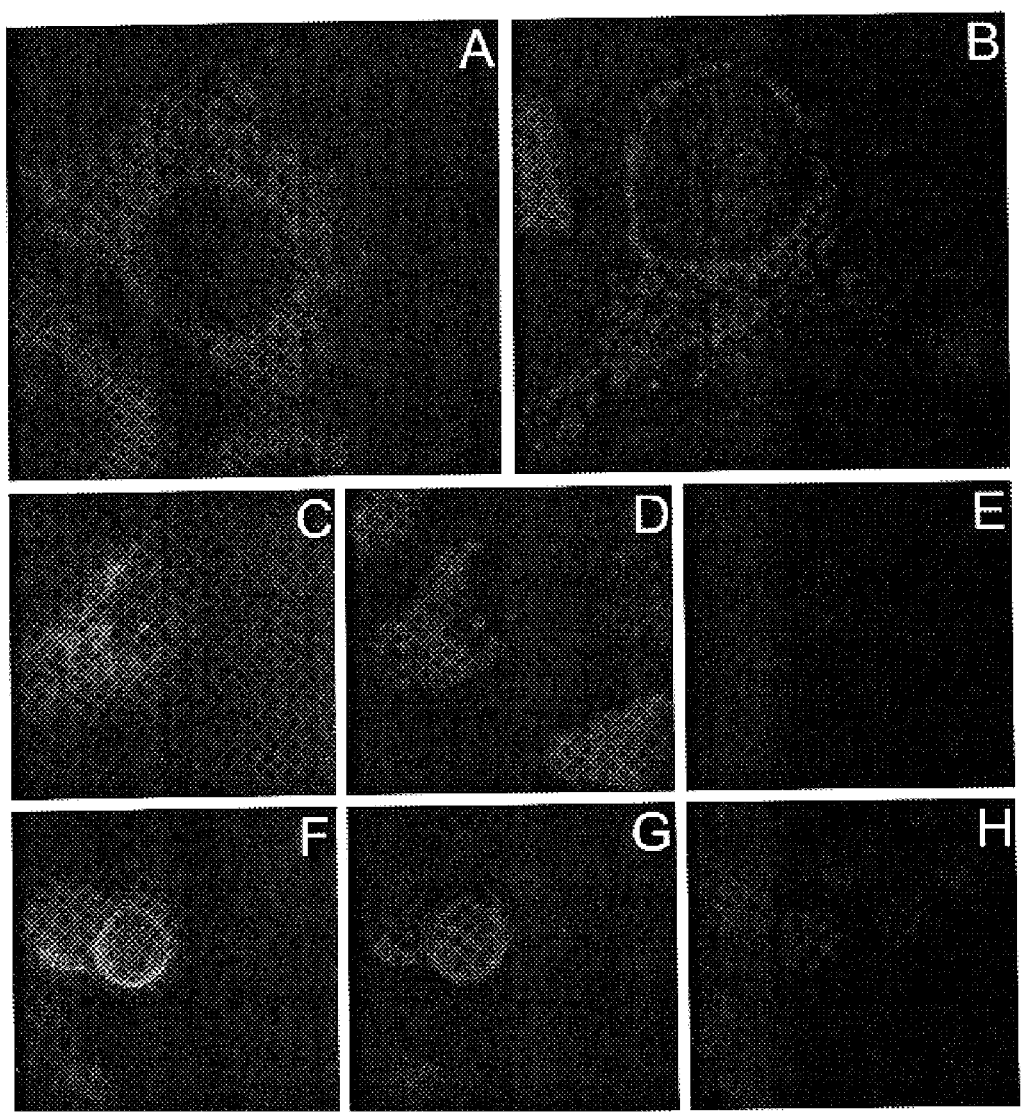
FIG. 15. Mitochondrial colocalisation of human αN-catenin and ANC_2H01, when one of the two proteins is tagged with a mitochondrial anchor sequence (MAS). (A) Mitochondrial staining in MCF7/AZ cells; (B) mitochondrial localisation of ANC_2H01 in MCF7/AZ cells after transfection with pcDNA3-EANC_2H01-MAS, showing that the MAS indeed retains the ANC_2H01 protein outside the nucleus; (C, D, E) double transfection of HEK293T cells with pcDNA3-EANC_2H01-MAS+pPNhαNCTN; (F, G, H) double transfection of HEK293T cells with pEFBOS-EANC_2H01+pcDNA3-αNCTN-MAS. ANC_2H01-mito (panel C) and ANC_2H01 (panel F) proteins were detected by anti-E-tag antibodies, followed by Alexa594-conjugated secondary antibodies; αN-catenin (panel D) and αN-catenin-mito (panel G) proteins were detected by the anti-α-catenin antibodies (Sigma), followed by FITC-conjugated secondary antibodies. DAPI staining was done to reveal the nuclei in the same cell fields (panels E and H).

HEK293T cells were transiently cotransfected either with pcDNA3-EANC_2H01-MAS and pPNhαNCTN or with pEFBOSANC_2H01E and pcDNA3αNCTN-MAS. Subcellular localisation of the proteins was assayed by immunocytochemistry experiments. We could show in the former case, that αN-catenin colocalized with the mitochondrial-targeted ANC_2H01 to the mitochondria (FIG. 15 C–E). In the latter case, ANC_2H01 colocalized with the mitochondrial-targeted αN-catenin to the mitochondria (FIG. 15 F–H). These results additionally support the hypothesis of a specific interaction between ANC_2H01 and αN-catenin.

Retransformation of ANC_2H01 in the Two-hybrid System

The primary purpose of this test is to check the specificity of the interaction between ANC_2H01 and αN-catenin. The isolated two-hybrid clone was retransformed into the HF7c strain. This ANC_2H01 clone was combined with either one of the following: the original bait plasmid pAS2ANCTN, the empty vector pAS2, the pGBT9ANCTN plasmid, the empty vector pGBT9 and pLAM5', a plasmid encoding an irrelevant protein (lamin C) fused to the GAL4 DNA binding domain. The ANC_2H01 exhibited the desired HIS3-positive β-galactosidase-positive phenotype upon combination with either pAS2ANCTN or pGBT9ANCTN. No interaction was seen when combination with either one of the empty vectors pGBT9 or pAS2, nor when combined with pLAM5'. Therefore, the initial observation was confirmed, which means that the interaction between ANC_2H01 and αN-catenin is specific.

Delineation of the Domains Mediating the Interaction Between ANC_2H01 and αN-catenin Proteins By the use of the two-hybrid system, we tried to analyze which part of the ANC_2H01 protein is responsible for the interaction with αN-catenin. Three different fragments of the initial two-hybrid clone ANC_2H01 were subcloned in the pGAD10 vector and were designated, respectively, ANC_2H01 /BamHI, ANC_2H01/600 and ANC_2H01/500 (FIG. 4). These three cDNA fragments each include the amino-terminal part of ANC_2H01. No interactions, however, could be observed between these different parts of ANC_2H01 and the αN-catenin protein (FIG. 4).

Figure 16:
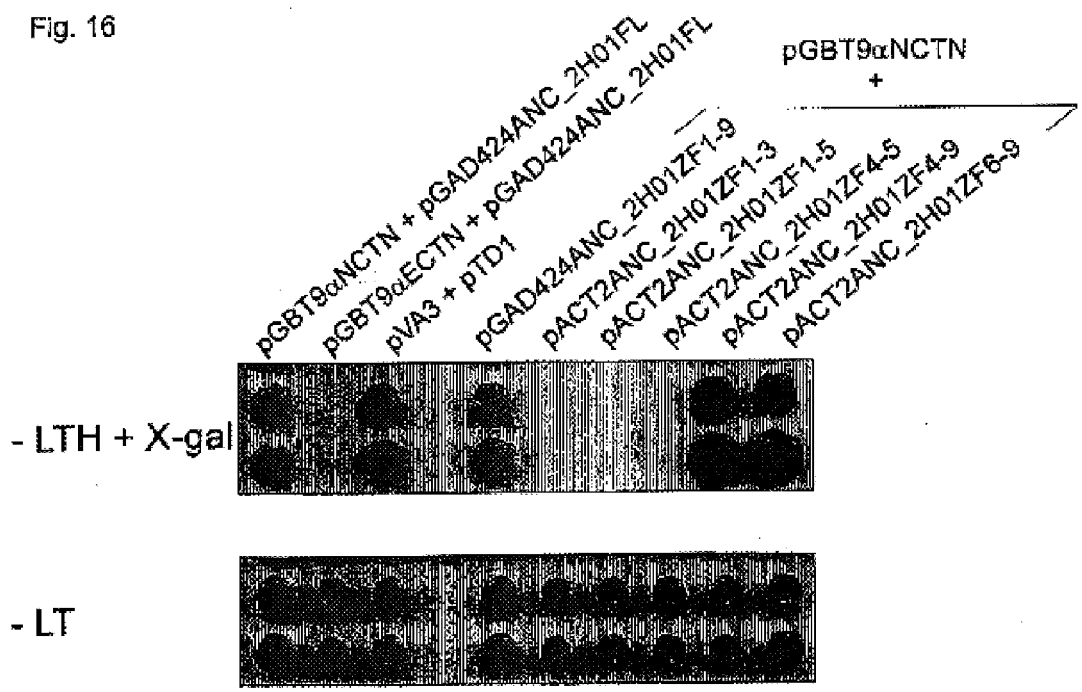
FIG. 16. The *Saccharomyces cerevisiae* strain Y190 was cotransformed with plasmid pGBT9-αNCTN, encoding αN-catenin, fused to the GAL4-DBD, in combination with a plasmid encoding fragments of ANC_2H01 fused to the GAL4-AD. The plates contained the medium composition indicated at the left completed with 40 mM 3-aminotriazole and 80 mg/ml X-gal. GAL4-AD=GAL4 transcription activation domain; GAL4-DBD=GAL4 DNA binding domain; −LT=SD medium lacking Leu and Trp; −LTH=SD medium lacking Leu, Trp and His; pVA3: plasmid encoding murine p53$_{(72-390)}$ fused to the GAL4-DBD; pTD1: plasmid encoding SV40 large T-antigen$_{(84-708)}$ fused to the GAL4-AD; pGBT9αECTN: plasmid encoding αE-catenin fused to the GAL4-DBD.

Subsequently, the zinc finger domain of ANC_2H01 was cloned behind and in frame with the GAL4-AD. Cotransformation of this plasmid with the pGBT9αNCTN plasmid into yeast cells, revealed a HIS3/LacZ positive phenotype. Using various fragments of the zinc finger domain of ANC_2H01 fused to the GAL4-AD, we could restrict the αN-catenin binding domain of ANC_2H01 to the zinc finger fragment 6–9 (FIG. 16). Indeed, after cotransformation of either the pACT2ANC2H01 ZF1–3, the pACT2-ANC2H01 ZF1–5 or the pACT2ANC2H01-ZF4–5 plasmid with pGBT9αNCTN, we could not observe any interaction between these zinc finger fragments and the αN-catenin protein. Only when the pACT2-ANC2H01ZF4–9 or the pACT2ANC2H01-ZF6–9 plasmid was challenged into the two-hybrid system, interaction was revealed by expression of the reporter genes.

By cloning different parts of αN-catenin into the pGBT9 vector, we delineated the domain responsible for association with ANC_2H01 to amino acid residues 4–537 of αN-catenin. The transformants harboring the plasmid pGBT9ANCTN(EcoRI-PstI) together with the ANC_2H01 plasmid exhibited the HIS3-positive, β-galactosidase-positive phenotype in the two-hybrid system (FIG. 4). All other combinations of αN-catenin fragments and ANC_2H01 did not result in the expression of the two reporter genes. Besides the interaction with the initial ANC_2H01 clone, we also looked in the two-hybrid system for the interaction of the various αN-catenin fragments with ANC_2H01/BamHI, ANC_2H01/600 and ANC_2H01/500. However, we could not observe any interaction between the different fragments of αN-catenin and any of the truncated ANC_2H01 fusion proteins (FIG. 4).

As αE-catenin is an isoform of αN-catenin, the cDNA for αE-catenin was cloned in frame with the GAL4 DNA binding domain into the pGBT9 two-hybrid vector. This clone was then assayed for interaction with ANC_2H01 and truncated derivatives in the two-hybrid system. However, no interaction was observed when both plasmids were cotransformed into the HF7c strain (FIG. 4).

Northern Blot Analysis

Figures 5, 6:
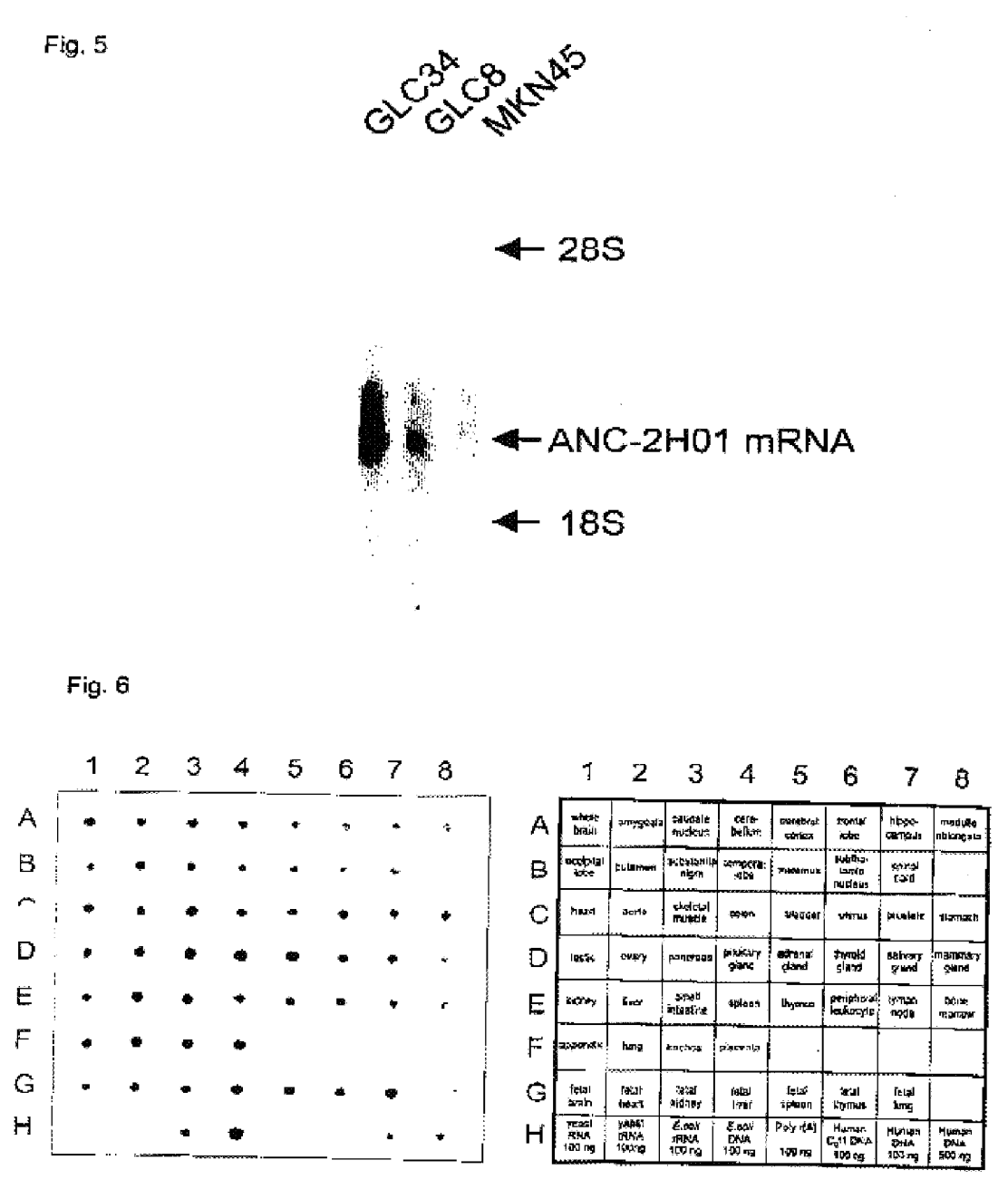

In order to estimate the length of the complete mRNA of ANC_2H01, we performed a Northern blot analysis. Total RNA of various human cell lines was hybridized with a $^{32}$P-labeled 700-bp BamHI fragment of the ANC_2H01 cDNA. A very weak signal could be detected in some cell lines, but most of the lanes lacked specific signal. However, a stronger signal was seen in the lanes with GLC34 and GLC8 RNA (FIG. 5). The positions of 28S and 18S ribosomal RNA on the blot were visualized using methylene blue staining. Using these positions as markers, we could estimate the size of the ANC_2H01 mRNA to be about 3,000 bp. The cDNA insert of the original ANC_2H01 two-hybrid clone was about 2,500 bp, and contained a stop codon, a poly-A signal and a poly-A tail (FIG. 2). However, a start codon could not be detected. This implies that we were lacking a 5' fragment of about 500 bp.

Multiple Tissue RNA Dot Blot Analysis

To survey tissue-specific expression of ANC_2H01, a multiple tissue RNA dot blot analysis was performed with a commercially available human RNA dot blot (Clontech). The ANC_2H01 mRNA showed a ubiquitus expression (FIG. 6). However, the strongest expression was observed for pituitary gland and adrenal gland mRNA. Lung, placenta, fetal liver and fetal lung also showed increased expression of the mRNA.

5'RACE

To isolate the lacking 500-bp 5' fragment of the ANC_2H01 cDNA, we used the 5' RACE technology (Gibco BRL). For this purpose, we used human mRNAs derived from mammary gland, fetal brain, uterus and small intestine (Clontech). Using a gene specific primer, an ANC_2H01 specific cDNA strand was synthesized. Using two nested primers sets (set #1 and set #2; see Table 1), we isolated 5 fragments from mammary gland and uterus mRNA. No fragments were amplified using the fetal brain or the small intestine mRNA. The 5' RACE fragments were cloned into the pGEM®-T cloning system and characterized by DNA sequence analysis. One of the inserts derived from mammary gland mRNA turned out to be specific for ANC_2H01. The four other 5'RACE products were non-specific. From further sequence analysis using walking primers (see Table 1) the size of the 5' RACE fragment was determined to be 823 bp (FIG. 2). This 823-bp fragment contained 520 bp as new 5' sequence and 303 bp as contained within the initial ANC_2H01 two-hybrid clone (FIG. 2). The 5' RACE fragment contained a start codon and 26 more codons that were not covered by the original ANC_2H01 two-hybrid clone (FIG. 1). In addition to the Alu repeat region detected in the 3'UTR of the cDNA, the 5'UTR also contains an Alu repeat region (FIG. 1 and FIG. 2).

The ANC_2H01 Gene Product is a Zinc Finger Protein

Scrutiny of the entire sequence of the ANC_2H01 cDNA revealed several interesting features. The cDNA has a total length of 3,013 bp. The 5'UTR was as long as 445 nt. The context of the start codon suits an adequate Kozak initiator sequence (Kozak, 1996). The 3' region contains a poly-A signal and a poly-A tail, indicating that also the 3'UTR is completely isolated and has a size of 1,112 nt. The 3'UTR as well as the 5'UTR contain one Alu repeat region (see FIG. 1). The cDNA encodes a protein of 485 amino acid residues (aa). The deduced molecular mass of the protein is 53.46 kDa. The protein contains nine zinc fingers in its carboxy-terminal half. All of these zinc fingers are of the $Cys_2His_2$ type (FIG. 3). They are clustered into two domains and followed by 3 aa only before the translational stop codon. The first five $Cys_2His_2$ zinc fingers are separated from the last four zinc fingers by 33 aa. Within each cluster, each zinc finger motif is only 3 to 5 aa apart from the following zinc finger. The presence of the 9 $Cys_2His_2$ type zinc fingers indicates that the protein binds double stranded DNA. In addition, a putative nuclear localisation signal (PKKRKRK (SEQ ID NO: 151); for review Görlich and Mattaj, 1996) is present in the protein at the amino-terminal side (residues 5–11; FIG. 1).

Further characterization of the isolated clone included a BLASTN search analysis (Altschul et al., 1990). The complete cDNA of ANC_2H01 did not correspond with any cloned full-size cDNA in the public-domain databases. However, several EST (Expressed Sequence Tag) clones with high degree of sequence similarity (low P-score) are present in the databases. These ESTs are from human origin (Table 7), as well as mouse origin (Table 8).

The ANC_2H01 Protein Localizes to the Nucleus and Translocates αN-catenin into the Nucleus HEK293T cells were transiently transfected with the pPNhANCTN plasmid and/or the pEFBOSANC_2H01E plasmid by a $Ca_3(PO_4)_2$ transfection procedure. The subcellular localization of the αN-catenin and the ANC_2H01 protein were analyzed by immunocytochemistry. The epitope tagged zinc finger protein could be specifically stained with a monoclonal antibody against the E-tag. To detect αN-catenin a commercial polyclonal antibody was used. The zinc finger protein ANC_2H01 localized to the nucleus upon transient expression in HEK293T cells. This nuclear staining was seen as well in cells transfected with the pEFBOSANC_2H01E plasmid alone as in cells that were transfected with both expression plasmids. In contrast, the αN-catenin protein was localized into the cytoplasm of cells transfected with plasmid pPNhANCTN only. When combined with the expression plasmid encoding the E-tagged ANC_2H01 protein, αN-catenin localized to the nucleus. So, a translocation of αN-catenin into the nucleus occurs, when the interacting zinc finger protein ANC_2H01 was co-expressed.

The same strategy was followed for αE-catenin and ANC_2H01. The pJ6αE-catenin was either transfected alone, or in combination with the pEFBOSANC_2H01E. The αE-catenin protein was always expressed in the cytoplasm, even upon co-expression with the zinc finger protein ANC_2H01. This is in agreement with the two-hybrid results, showing no interaction between αE-catenin and the novel zinc finger protein ANC_2H01.

RT-PCR

Figure 17:
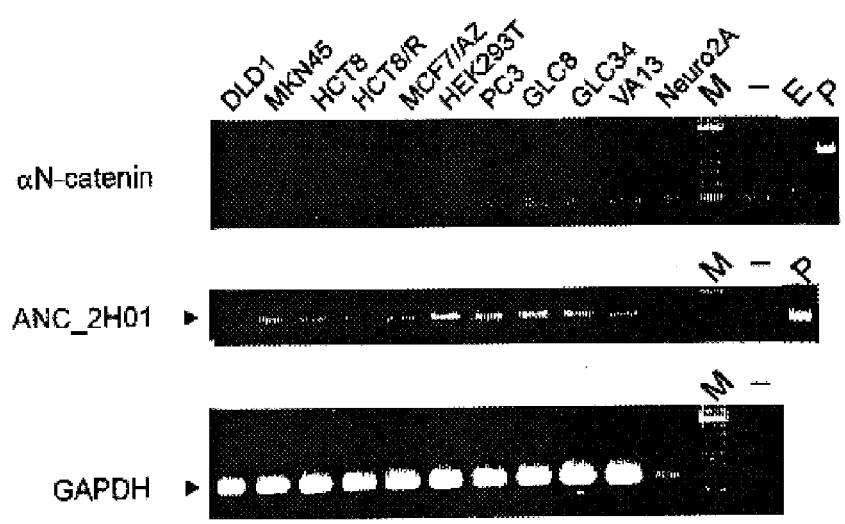
FIG. 17. Examination by RT-PCR of various human tumor cell lines and one murine cell line (Neuro 2A) for the presence of αN-catenin and ANC_2H01 mRNA. Amplification of GAPDH transcripts served as a control for the mRNA/cDNA template.

A set of ANC_2H01-specific compatible primers, FVR1686F and FVR1687R, was used in an RT-PCR experiment. Using these primers, a fragment could be amplified by RT-PCR from pools of RNA, derived from various human cell lines and one mouse cell line. All cell lines we examined scored positive (FIG. 17). We also tested for the presence of αN-catenin mRNA in these cells using specific primers FVR1762F and FVR1826R. In no case an αN-catenin specific band could be detected. The primers were also tested on a αE-catenin template to determine the specificity. No product was detected (lane E). As a positive control, a fragment was amplified from a template containing a full-length αN-catenin cDNA. A PCR using GAPDH-specific (SEQ ID NO: 157) primers (FVR1986F and FVR1987R) was performed as a positive control (FIG. 17). A band of the expected size was seen in each lane, suggesting that in each reaction the cDNA was present. All primers were developed on cDNA derived from man. This may explain the weak signals for the murine Neuro2A cell line (FIG. 17).

Western Blot Analysis

Figure 8:
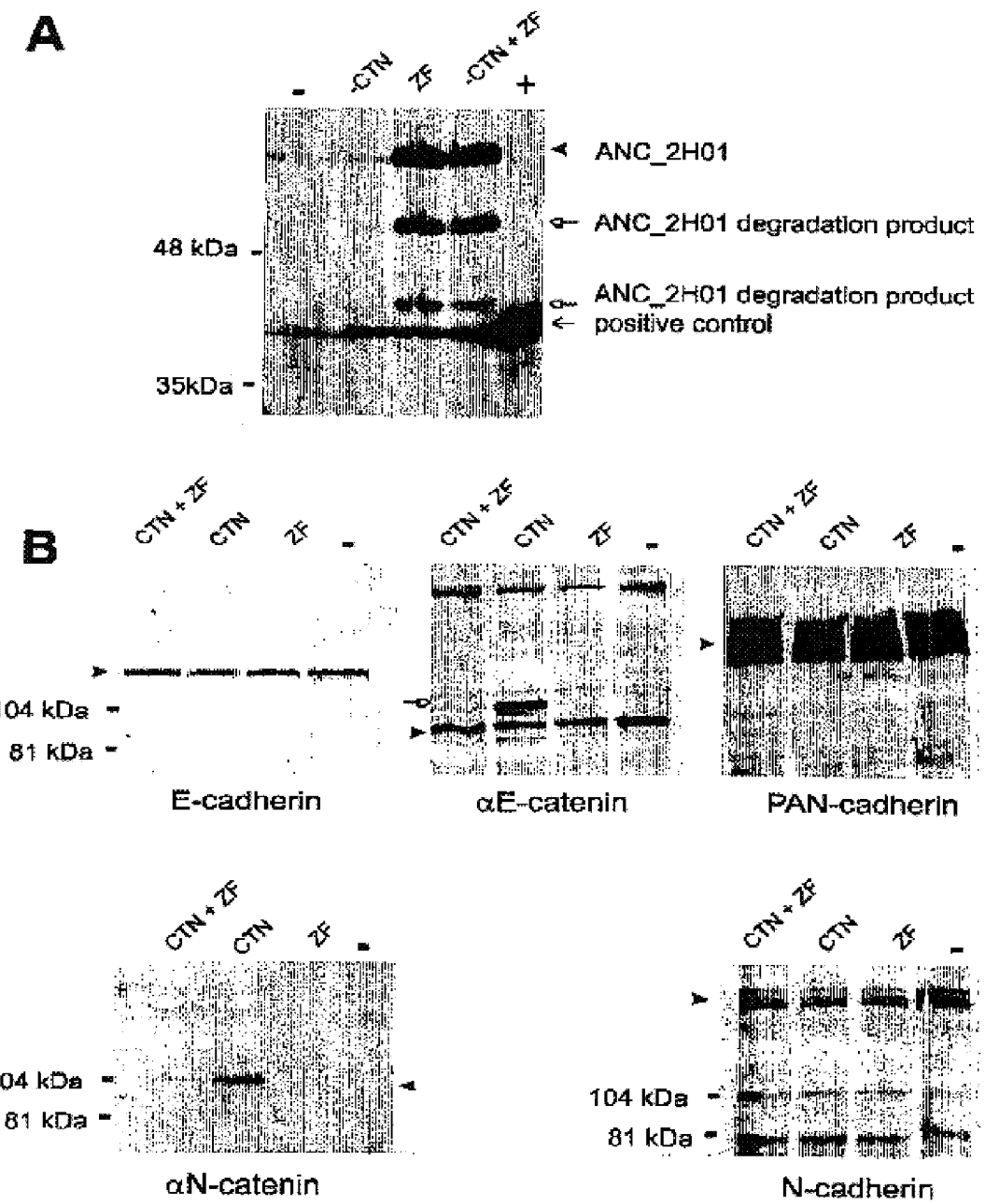
FIG. 8. Western blot analysis of transfected and untransfected HEK293T cells. The cells were transfected with either pPNhANCTN (indicated by CTN) or pEFBOSANC_2H01E (indicated by ZF) or with both plasmids. Molecular weight markers are indicated each time at the left. (A) Blots were stained with the monoclonal antibody against the E-tag. A band of approximately 60 kDa is detected (closed arrowhead), which is the expected size for the tagged ANC_2H01 protein. Two weaker bands are also detected and are thought to be degradation products (closed arrows). As a positive control, an unrelated E-tagged protein was loaded in the lane indicated with +. (B) The expression levels of several proteins of the cadherin-catenin complex (indicated by closed arrowheads) were also analyzed in these cells (E-cadherin, N-cadherin, pan-cadherin, αN- and αE-catenin), but no differences could be observed at a semi-quantitative level. The band indicated with an open arrow is presumably αN-catenin, what indicates that the anti-αE-catenin antibody used is cross-reacting with αN-catenin.

Lysates of HEK293T cells transiently transfected with pPNhANCTN and/or pEFBOSANC_2H01 were prepared 24 h after transfection and examined for the expression of the recombinant proteins. The ANC_2H01 protein was detected by the use of the E-tag. The tagged protein has a predicted molecular mass of approximately 55 kDa and such a band was indeed detectable (FIG. 8A). Two weaker bands with lower molecular weight were also observed on the blot. This may be due to proteolysis of the protein at the carboxy-terminus. The E-tag, which is fused at the amino-terminal part of the protein, is still available in protein fragments degraded at the carboxy-terminus.

The presence of αN-catenin was revealed by the use of a polyclonal antibody against αN-catenin. A single band of approximately 100 kDa was recognized by this antibody in single and double tranfected cells (FIG. 8B). The predicted molecular mass of αN-catenin is 100,686 daltons.

The presence of other cadherins and cadherin-associated molecules was also examined in these cells. E-cadherin was present in non-transfected cells as well as in single and double transfected cells (FIG. 8B). Using an anti-pan-cadherin antibody, a broad band could be observed for the different transfected cells, probably covering several cadherins. We also tried to detect αE-catenin, using an antibody against this protein. The transfected as well as the non-transfected cells showed staining for αE-catenin (FIG. 8B). When recombinant αN-catenin was expressed, the anti-αE-catenin antibody recognized also a larger band. This additional band was observed in the αN-catenin single transfectant, but was weaker in the double transfectant. We concluded that the anti-αE-catenin antibody used recognized also the recombinant αN-catenin expressed in these cells.

At a semi-quantitative level we could not detect any drastic differences in the untransfected versus the transfected cells upon staining for E-cadherin, pan-cadherin, or αE-catenin.

PAC Screening

Superpools and subsequent plate-pools from the UK-HGMP PAC library (Roswell Park Cancer Institute, Buffalo, N.Y.) were screened by PCR with ANC_2H01-specific primers FVR513F and FVR514R (Table 1). This resulted in the determination of the plate number of a 384-well microtiter plate containing a positive clone. Further PCR analysis of the pooled rows and columns pinpointed the positive clone 167024 as specific for the ANC_2H01 gene.

Chromosomal Localization of the ANC_2H01 Gene by FISH Analysis

Figure 9:
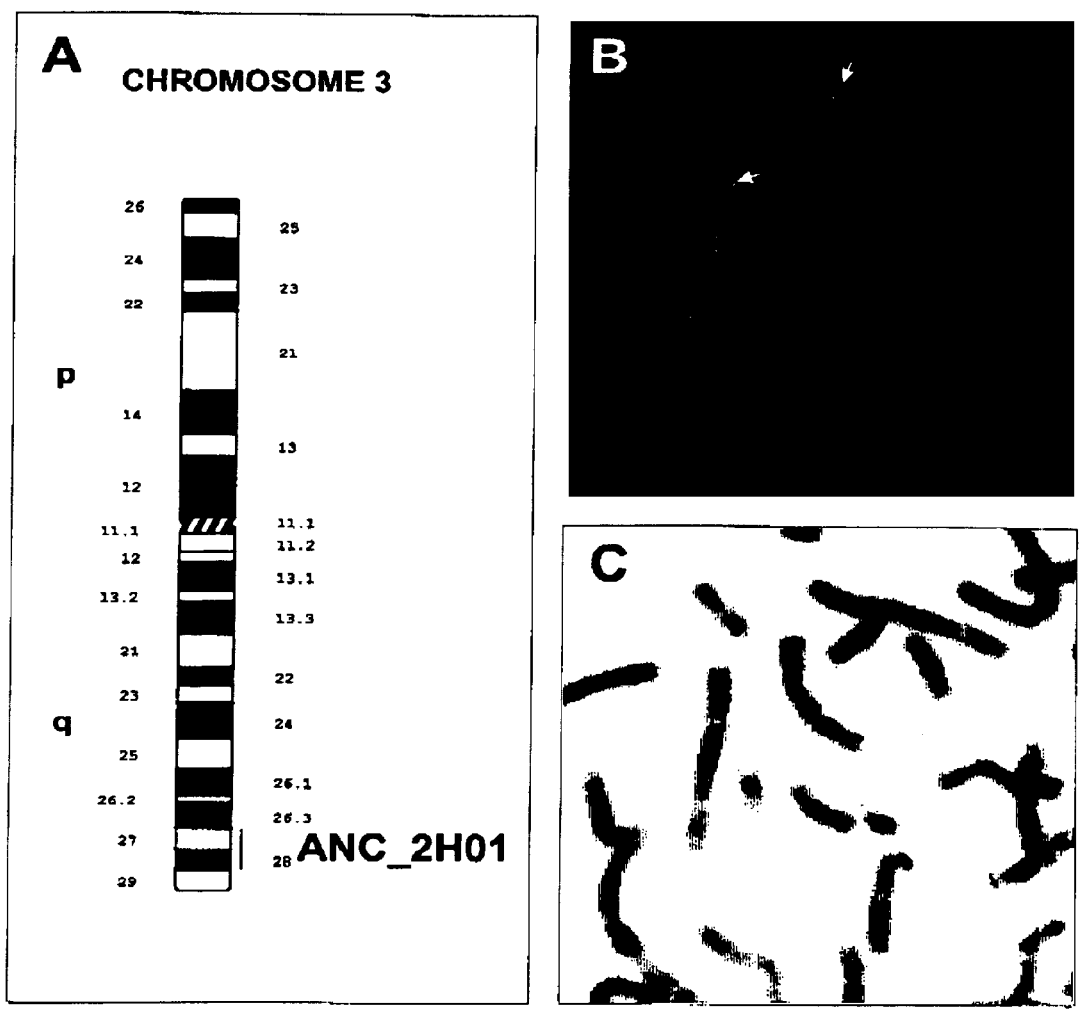
FIG. 9. Chromosomal localization of the human ANC_2H01 gene at band 3q27–28 by fluorescence in situ hybridization. (A) Ideogram of chromosome 3; (B) Fluorescence signal specific for the ANC_2H01 gene; (C) DAPI staining of the same chromosomes.

FISH was performed using the PAC clone 167O24 specific for the ANC_2H01 gene. We mapped the gene encoding the zinc finger ANC_2H01 on the chromosomal locus 3 q27–28. To this end, we analyzed 20 metaphases. Up to 15 of them revealed discrete hybridization signals on both chromosomes 3 at band 3 q27–28 (FIG. 9). The other metaphases showed signal on only one of both chromosomes 3.

Two-ybrid Analysis of the Interaction of ANC_2H01 with αE/αN-catenin Chimeras

The zinc finger protein ANC_2H01 does not interact with αE-catenin when tested in the yeast two-hybrid system. The human αE-catenin protein shows, however, 80% homology with the closely related human αN-catenin protein. In spite of this high similarity, their tissue distribution is clearly distinct. Both proteins show also identity with vinculin in three regions with higher sequence conservation, the so-called vinculin homology domains (VH) (Herrenknecht et al., 1991) (FIG. 10). In an approach to further characterize the specific interaction between αN-catenin and ANC_2H01, we made α-catenin chimeric molecules by exchanging these VH domains between αN-catenin and αE-catenin. In a first approach, we constructed six different αN/αE-chimeras fused to the GAL4 DNA binding domain (FIG. 10). The possible interaction of these six αN/αE-chimeras with the ANC_2H01 protein was analyzed using the two-hybrid system. We observed no expression of either the selection gene HIS3 or the reporter gene LacZ when either the initial ANC_2H01 two-hybrid clone or pGAD424ANC_2H01-FL was cotransformed into Y190 yeast cells with pGBT9αECTN, pGBT9αECTNVH1N, pGBT9αNCTNVH2E or pGBT9αECTNVH3N (FIG. 11). In addition, no interaction could be detected when the Y190 yeast strain was cotransformed with the initial ANC_2H01 two-hybrid clone or pGAD424ANC_2H01-FL on the one hand, and the pGBT9αNCTNVH1E and pGBT9αECTNVH2N plasmids on the other hand. However, a HIS3-positive, β-galactosidase-positive phenotype was obtained upon combination of ANC_2H01 or pGAD424ANC_2H01-FL with either pGBT9ANCTN or pGBT9αNCTNVH3E (FIG. 11).

Figure 19:
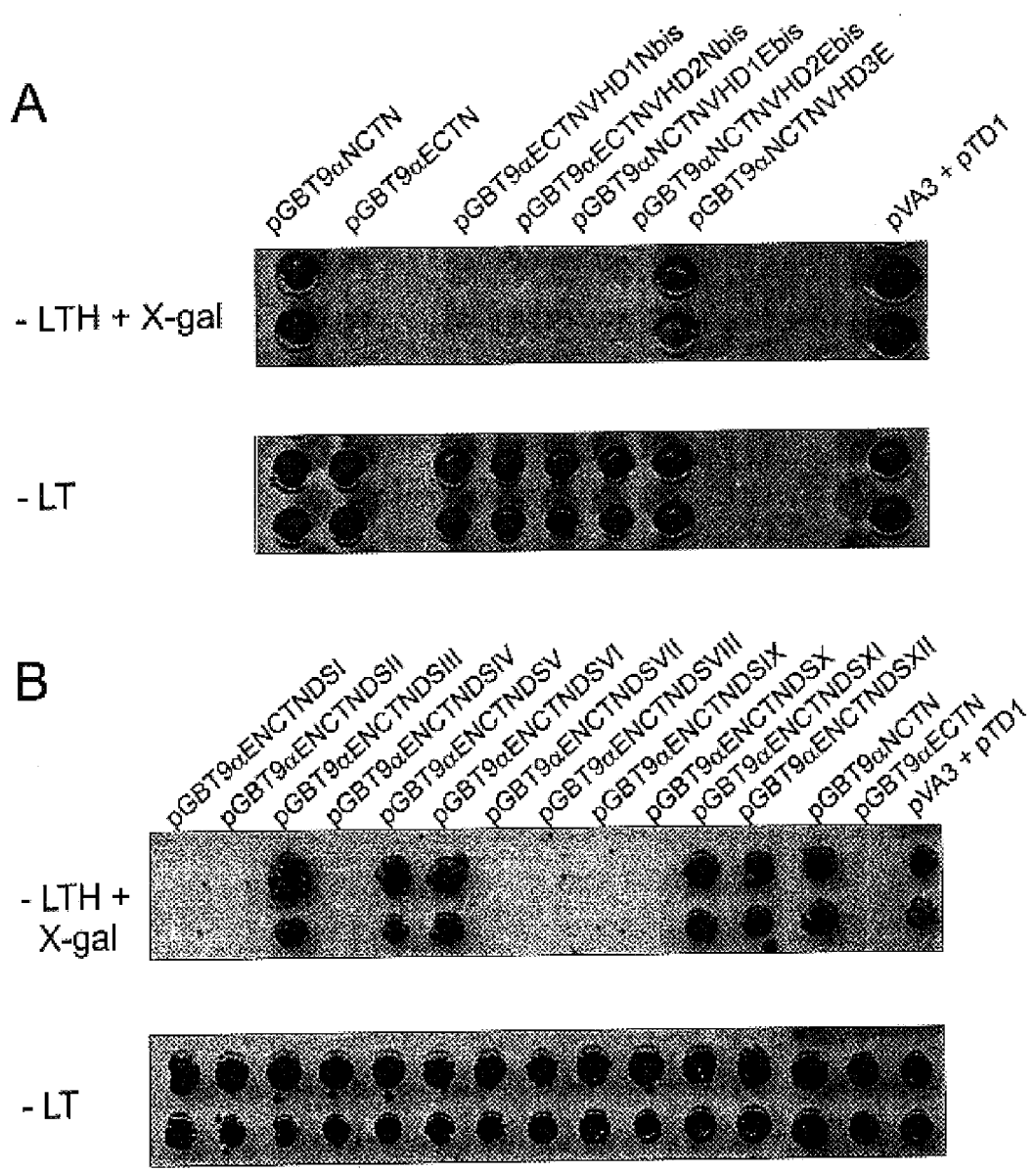
FIG. 19. The *Saccharomyces cerevisiae* strain Y190 was cotransformed with plasmid pGAD424ANC_2H01-FL encoding full-length ANC_2H01 fused to the GAL4-AD, in combination with (A) and (B) αE/αN-catenin chimeras fused to the GAL4-DBD. The plates contained the medium composition indicated at the left completed with 40 mM 3-AT and 80 mg/ml X-gal. pVA3, pTD1, and abbreviations are as in FIG. 16.

To further delineate the domains of αN-catenin responsible for the specific interaction with the ANC_2H01 protein, another set of 19 constructs was made, containing αE/αN-catenin chimeric cDNAs fused to the GAL4-DNA binding domain. The interaction of these α-catenin chimeric molecules with the full-length ANC_2H01 protein was assayed by the yeast two-hybrid system. The His3 and LacZ reporter genes were expressed when the pGAD424ANC_2H01-FL plasmid was cotransformed into the Y190 yeast cells with pGBT9αENCTN-DSIII, pGBT9αENCTN-DSVI, pGBT9αENCTN-DSVII, pGBT9αENCTN-DSXII or pGBT9αENCTN-DSXIII plasmid (FIGS. 12 and 19). However, no interaction was observed in the two-hybrid sytem between the fusion proteins encoded by the pGAD424ANC_2H01-FL plasmid on the one hand and the ones encoded by the pGBT9AαENCTN-DSI, pGBT9αENCTN-DSII, pGBT9αENCTN-DSIV, pGBT9αENCTN-DSVIII, pGBT9αENCTN-DSIX, pGBT9AENCTN-DSX, pGBT9αENCTN-DSXI plasmid on the other hand. In addition, no interaction could be detected when the yeast cells were cotransformed with the pGAD424ANC_2H01-FL plasmid on the one hand and the pGBT9αECTNVH1Nbis, the pGBT9αNCTNVH2Ebis, the pGBT9αNCTNVH1Ebis or the pGBT9αECTN-VH2Nbis plasmid on the other hand (FIG. 19).

These results enabled us to identify two separate domains of the human αN-catenin protein as the ANC_2H01-binding domains. The first ANC_2H01-binding domain comprises aa 134 to aa 279 of αN-catenin. Comparison of the sequence of this αN-catenin domain to the homologous domain of αE-catenin reveals still 58 differences in amino acid residues, which are randomly distributed (FIG. 18A). The second ANC_2H01-binding domain is situated between aa 374 and aa 549. In this second region, only 19 differences in the amino acid sequence between αN-catenin and αE-catenin could be observed (FIG. 18B). Both these domains appear to be necessary for the specific interaction between αN-catenin and the zinc finger protein ANC_2H01. In fact, replacing the corresponding domains of αE-catenin by the two ANC_2H01-binding domains of αN-catenin (construct pGBT9αENCTN-DSXIII) turns the αE-catenin protein into an αN-catenin-like molecule, at least with respect to the binding of ANC_2H01.

In Silico Analysis of the Human Genomic Clone Specific for ANC_2H01

Figure 20:
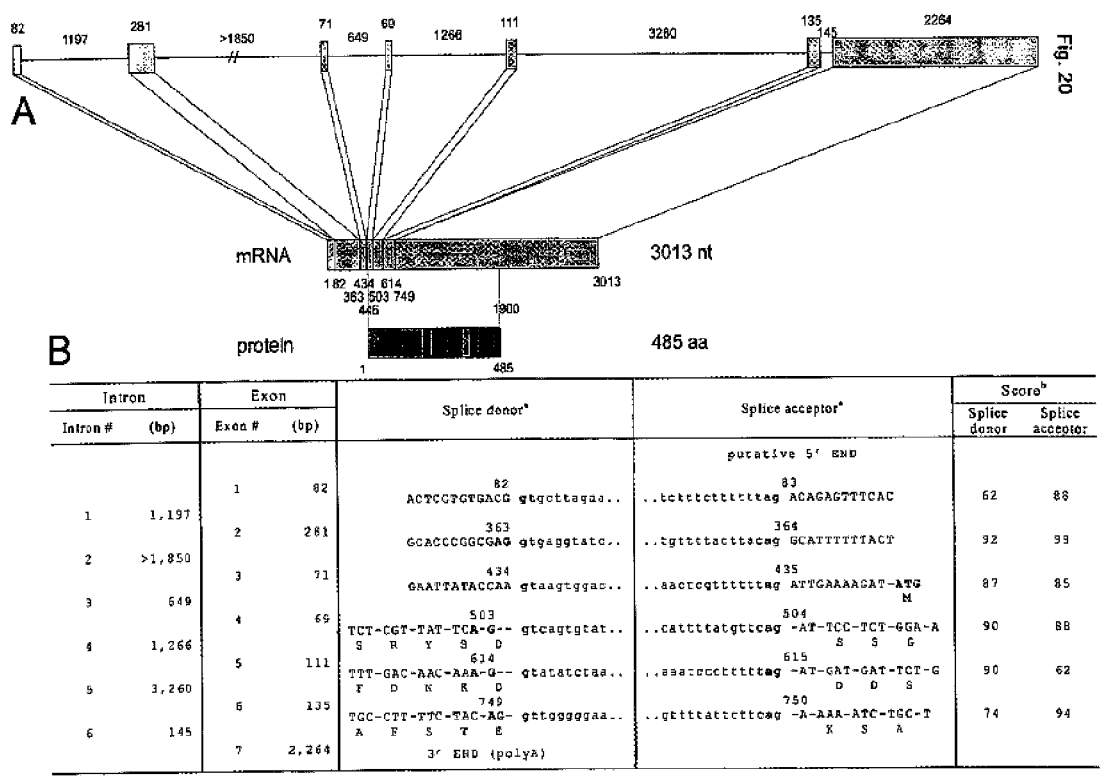
FIG. 20. (A) Schematic representation of the human ANC_2H01 gene, cDNA and protein. The gene consists of seven exons and six introns, of which the sizes are indicated in bp. Numbers below the mRNA scheme and the protein scheme refer to nucleotides (nt) in the transcript, and amino acid residues (aa) in the protein, respectively. (B) Overview of the introns, exons, and intron/exon boundaries (SEQ ID NOS: 139–150) of the human ANC_2H01 gene, [a] intron sequences in lowercase letters, exon sequences in capital letters; splice consensus sequences (ag-gt) in bold; amino acid residues (single letter codes) (under heading Splice donor, residues 16–20, 53–57 and 98–102 of SEQ ID NO: 2 are indicated) are indicated below the corresponding codons, the methionine start codon is in bold; [b] scores for donor and acceptor splice sites according to the method of Shapiro and Senapathy (1987).

An ANC_2H01-specific human genomic clone (Genbank Acc. No. AC007823) was identified on the basis of a BLASTN search analysis in the HTGS part of the GenBank database. The gene is present in a BAC vector. This BAC is localized on the human chromosomal region 3 q26.2–27. This is in accordance with our FISH results, mapping the ANC_2H01 on 3 q27–28. We performed an in silico analysis of the genomic sequence for the ANC_2H01 gene. The exon-intron boundaries of the ANC_2H01 gene could be determined by comparison of the cDNA and genomic sequences. They all turned out to be consistent with the ag-gt rule (Mount, 1982). The splice donor/acceptor probability scores were determined according to Shapiro and Senapathy (1987) (FIG. 20). The ANC_2H01 gene consists of seven exons, ranging in size between 69 bp (exon 4) and 2,264 bp (exon 7). The first three exons are non-coding. The last exon is the largest and encodes for the whole zinc finger domain of the protein plus additional aminoterminal sequences (FIG. 20).

Discussion

For a better understanding of the respective role of the two subtypes of α-catenin protein, we set up a two hybrid screen with human αN-catenin as a bait. From a human kidney cDNA library, a single clone was isolated exhibiting the desired HIS3-positive, β-galactosidase-positive phenotype. This two-hybrid clone was completely sequenced and the partial cDNA was completed by 5' RACE. This resulted in a full size cDNA of 3,013 nucleotides (nt) in correspondence with the results of the Northern blot analysis. The 3'UTR as well as the 5'UTR contain an Alu repeat region. In addition, the 3' region contains a poly-A signal and a poly-A tail, indicating that the 3'UTR is completely isolated.

The ATG start codon occurs in an adequate, although not fully optimal context according to Kozak (Kozak, 1996). The open reading frame is 1458 nt in length and encodes a protein of 485 aa. Structurally, the protein can be divided into two domains. The amino-terminal part contains no obvious protein motifs, except for a stretch of basic aa nearby the amino-terminus of the protein (PKKRKRK, aa 5–11) (SEQ ID NO: 151). This short sequence resembles the nuclear localization signal of the SV40 large T antigen (PKKKRKV) (SEQ ID NO: 151) (Kalderon et al., 1984). On the other hand, the carboxy-terminal part consists of 9 zinc fingers of the $Cys_2His_2$ type. These are clustered in two domains, separated from each other by 33 aa. Between consecutive zinc fingers, generally five aa are present. Zinc finger motifs of the $Cys_2His_2$ type were first discovered in the transcription factor TFIIIA and have DNA binding properties (Hanas et al., 1983; Miller et al., 1985). Another feature of these motifs is their autonomous folding up and their stabilization by chelation of zinc between a pair of cysteine and a pair of histidine residues. It has also been shown that in these polydactyl proteins the DNA interaction is dominated by only few of the many zinc fingers (Sun et al, 1996; Georgopoulos et al., 1997). One zinc finger of the $Cys_2His_2$ type binds typically 3 bp of a double-stranded DNA sequence, and this is called a subsite. Structural studies of such DNA-protein complex also revealed that consecutive fingers of a polydactyl protein interact with subsites directly adjacent to each other (Pavletich and Pabo, 1991 and 1993). It was also suggested that not all of the zinc fingers from a polydactyl protein contribute to DNA binding and recognition and that the remaining non-DNA-binding zinc fingers may participate in protein-protein interactions. Interactions with another protein as well as homodimerization have been reported in this context (Sun et al., 1996; Morgan et al., 1997).

In this study, we could also show that several amino-terminal fragments of ANC_2H01 do not interact with αN-catenin, at least not in the two-hybrid system. These results may suggest that the amino-terminal domain is not responsible for the interaction. We could indeed demonstrate that the zinc finger region, more specifically the fragment including zinc fingers 6 to 9 of ANC_2H01 extended with 5 aa of a 33-aa spacer separating central (1–5) from carboxyterminal (6–9) zinc fingers, was binding to αN-catenin. Using the two-hybrid system, the associating domain of αN-catenin for ANC_2H01 could be delineated at aa 4–535. In addition, the interaction of αE-catenin with the ANC_2H01 protein could not be observed in the two-hybrid system. Further studies using αE/αN-catenin chimeras showed that for the interaction with the ANC_2H01 protein, the first two vinculin homology (VH) domains of αN-catenin are needed. No interaction was observed when only the VH1 or the VH2 domain of αN-catenin was included in chimeric proteins with αE-catenin. Further the study narrowed the ANC_2H01-binding domain of αN-catenin down to two separate domains. Both domains are necessary for specific binding. Moreover, replacing the corresponding regions of αE-catenin by these domains of αN-catenin, confers αN-catenin properties to αE-catenin, at least with respect to the binding of the ANC_2H01 protein. In agreement with the aforementioned data, these results strengthen the conclusion that the interaction with the ANC_2H01 is αN-catenin-specific.

To localize the novel ANC_2H01 zinc finger protein and the αN-catenin/ANC_2H01 complex within cells, we transiently transfected expression constructs encoding these two proteins into human cells (HEK293T) and visualized the proteins by immunofluorescence. The αN-catenin was distributed throughout the cytoplasm, as reported previously (Shibuya et al., 1996). This suggests that the αN-catenin molecules are generally dissociated from cadherins, because cadherins were detected in the lysates of the HEK293T cells. Co-expression of the cDNA encoding the tagged zinc finger protein, resulted in the translocation of αN-catenin to the nucleus. The ANC_2H01 protein was consistently detected in the nucleus. This observation is in line with the presence of a putative nuclear localization signal in the ANC_2H01 protein and with the putative DNA binding nature of the zinc fingers.

The specific interaction between ANC_2H01 and αN-catenin could also be confirmed by the co-immunoprecipitation experiments and by the experiments in which mitochondrial colocalisation of ANC 2H01 and αN-catenin was achieved.

Using FISH the ANC_2H01 gene could be mapped to the q27–28 region of human chromosome 3. A study of James and coworkers (James et al., 1996) using YACs covering the human chromosomal regio 3q27, identified ESTs for five genes, including three members of the cystatin gene family and a gene thought to be involved in B-cell non-Hodgkin lymphoma. The latter was confirmed by the identification of the BCL6 (B-cell non-Hodgkin lymphoma) disease gene in this region (Chaganti et al., 1998). The p63 gene, which bears strong homology with the tumor suppressor gene p53 and p73 is also localized in the chromosomal region 3q27–29 (Yang et al., 1998). In addition, another member of this family, p73L, was also assigned to the 3q27–28 region (Senoo et al., 1998).

A genomic human BAC-sequence, deposited in the Genbank database, was found to comprise the ANC_2H01 gene, on the basis of BLASTN search analysis. Our in silico analysis of this genomic sequence revealed six introns and seven exons. Interestingly, this BAC has been localized in the human chromosomal region 3q26.2–27. This is in agreement with our FISH results.

The expression study of the ANC_2H01 gene reveals a ubiquitous transcription activity. This was observed both in RT-experiments and in a hybridisation experiment using a Multiple Tissue Northern dot blot. Moreover, expression analysis on the basis of several EST (Expressed Sequence Tag) clones with high degree of sequence similarity (low p-score) confirms these observations. These ESTs are from human origin, as well as from mouse and rat origin and are indeed derived from various tissues.

Taken together, these data show that αN-catenin regulates gene expression by a direct interaction with a novel nuclear zinc finger protein. This transcription factor, that was cloned by us, shows no identity with any cDNA or protein in the public databases, except for a number of unspecified EST clones. The ANC_2H01 protein induces a translocation of αN-catenin to the nucleus by protein-protein association, an observation that has not been reported before. The interaction of the zinc finger protein is considered to be αN-catenin-specific. It is now possible to elucidate the target genes of the transcription factor and the function of the αN-catenin/ANC_2H01 complex in cell-cell adhesion, cellular differentiation and other signalling pathways. Furthermore, it is possible to further delineate the interacting domains of ANC_2H01 and αN-catenin using the two-hybrid system and other approaches; to determine the DNA sequences to which the ANC_2H01 protein specifically binds; to identify other proteins, specifically interacting with the ANC_2H01 protein; to raise specific monoclonal and polyclonal antibodies for the ANC_2H01; and for example to perform drug screens that either enhance or reduce the interaction between the ANC_2H01 and αN-catenin or other proteins.

The Brx/proto-Lbc Protein Interacting with α-catulin
Two-hybrid Library Screening By screening a HeLa library with α-catulin as a bait, a positive clone ACTL2H_K_E2 was isolated showing an insert of 638 bp without interruption of the open reading frame. This DNA sequence turned out to be identical to part of the human Brx cDNA sequence (FIG. 26).

Indeed, the isolated cDNA sequence showed identity to two cDNA sequence submissions in GenBank, i.e. AF126008 and AF127481. The encoded human Brx (Breast cancer nuclear Receptor-binding auxilliary protein) and proto-Lbc (proto-Lymphoid Blast Crisis) proteins were discovered independently by two research groups (Rubino et al., 1998; Sterpetti et al., 1999), but are probably transcripts derived from the same gene, mapped on human chromosome 15.

Figure 21:
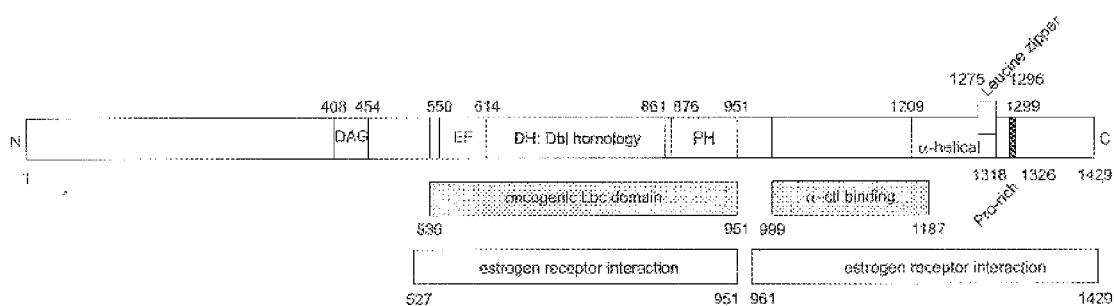
FIG. 21. Schematic representation of the Brx/proto-Lbc protein with its assigned functional domains (see text), including the novel interaction with α-catulin (α-ctl).
Figure 22:
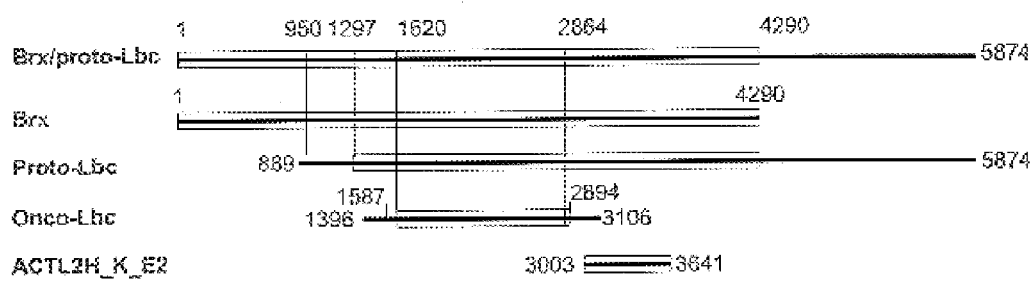

The submitted cDNA sequences for human Brx (AF126008), proto-Lbc (AF127481) and onco-Lbc (U03634) are schematically aligned in FIG. 22. The SK15 proto-Lbc mRNA is alternatively spliced at the 5' end, thus contains a stop codon and a shorter amino terminus than shown for Brx. The submitted sequence of proto-Lbc shows also an extended 3' UTR as compared to Brx (not shown), but the open reading frame remains the same at the carboxy terminus. Thus protein sequences of 1429 and 950 amino acid residues are obtained, respectively, with as only difference an extended amino-terminus for the Brx protein. For convention, the cDNA fragment isolated by us as clone ACTL2H_K_E2 in the two hybrid system will further be referred to as the Brx(3003–3641) fragment, encoding amino acid residues 999 to 1187 of the Brx protein. Known domains of the Brx and proto-Lbc proteins are summarized in FIG. 21.

Retransformation of α-catulin's Prey Brx in the Two Hybrid System

Figure 27:
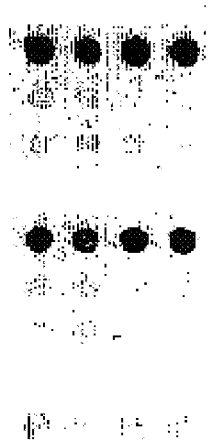
FIG. 27. Retransformation of the prey plasmid pGADGH-Brx with the original bait plasmid (designated here pGBT9ACTL) and with bait plasmids of other members of the α-catenin/vinculin family (αE-catenin and αN-catenin), as shown. The pVA3 bait plasmid and the pTD1 prey plasmid (Clontech) served as negative controls, unless combined with each other (positive control).

By using α-catulin as a bait in a two-hybrid screen, part of Brx was obtained as a prey. To confirm that the α-catulin/Brx interaction is specific for α-catulin and does not occur with other members of the α-catenin/vinculin family, the Brx prey plasmid (abbreviated as pGADGH-Brx) was re-transformed with various members of the family as bait (FIG. 27). In this way, we could prove that in the two-hybrid system the interaction between the Brx fragment and α-catulin occurs specifically and neither with αE-catenin, nor with αN-catenin, nor with αT-catenin.

Confirmation of the α-catulin/Brx Interaction by co-immunoprecipitation

After transient cotransfection of HEK293 cells with the constructs pES31-αctl(47–2247)-E and pCS2MT-Brx (3003–3541), immunoprecipitations were performed with anti-Myc and anti-E-tag antibodies. After transient transfection of HEK293 cells with the constructs pES31-αctl (47–2247)-E and pBK-RSV-Brx(142–4290), immunoprecipitations were performed with, respectively, anti-E-tag antibodies and anti-Flag or anti-Myc antibodies. In all cases, the overexpressed proteins could be co-immunoprecipitated (FIG. 7), thus confirming the abovementioned interaction between α-catulin and Brx, shown in the yeast two-hybrid system.

Discussion

The present invention demonstrates that the human α-catulin protein specifically interacts with a fragment of the C-terminal region of the Rho-GEF Brx/proto-Lbc. α-catulin can thus be used as a negative or a positive regulator of the Rho-GEF activity. Moreover, the α-catulin association may contribute to the localization of Brx/proto-Lbc to particulate fractions of the cytosol, whereas the onco-Lbc, lacking the α-catulin binding domain, is found all over the cytosol (Sterpetti et al., 1999). Binding of α-catulin may inhibit the oncogenic and transforming potential of the Brx/proto-Lbc protein. Also, α-catulin may be involved in signaling cascades involving the estrogen receptor, to which Brx/proto-Lbc is binding, thus providing a stronger response. Alternatively, it may inhibit interaction between Brx/proto-Lbc and the ER, as the binding site for α-catulin is overlapping with one of the binding sites for the ER. Further, α-catulin may be involved in linking and signaling between for example the thrombin receptor and Brx/proto-Lbc (Majumdar et al., 1999). Finally, α-catulin may contribute to cadherin-mediated cell-cell adhesion and other biological processes, that are regulated by small GTPases of the Rho subfamily (Rho, Rac, Cdc42) (Braga, 1999; Kaibuchi et al., 1999).

TABLE 1

PRIMERS USED FOR CHARACTERIZATION OF THE HUMAN ANC_2H01 CDNA

| Primer[a] | Position[b] | Application[c] | Sequence 5'→3'[d] |
|---|---|---|---|
| FVR274F | 845 | SE | actgctgaagatgttccaat (SEQ. I.D. NO. 12) |
| FVR291F | 1,215 | SE | aggatccctacatttgtaaa (SEQ. I.D. NO. 13) |
| FVR293F | 1,657 | SE | ttgtgatgactgtgggaaag (SEQ. I.D. NO. 14) |
| FVR308R | 2,766 | SE | cctgggcaacatagcgagat (SEQ. I.D. NO. 15) |
| FVR309R | 812 | SE | ggactctcctcttgggtttg (SEQ. I.D. NO. 16) |
| FVR310R | 666 | SE | tctgttctggccttgattc (SEQ. I.D. NO. 17) |
| FVR345F | 673 | CL | gcactatggccagaaacagaaatcaga (SEQ. I.D. NO. 18) |
| FVR346R | 996 | CL | ggaattcctgggcagtcacattcaaag (SEQ. I.D. NO. 19) |
| FVR347R | 1,095 | CL | ggaattccatatgctgctttaagtcag (SEQ. I.D. NO. 20) |
| FVR359R | 940 | RA | gcggttcttcatcagtttgg (SEQ. I.D. NO. 21) |
| FVR360R | 804 | RA | ctcttgggtttgctggttga (SEQ. I.D. NO. 22) |
| FVR421R | 478 | SE | aacgagaagggtgtagagtc (SEQ. I.D. NO. 23) |
| FVR462R | 2,364 | SE | tcctgtaatagtggcttcct (SEQ. I.D. NO. 24) |
| FVR463F | 1,660 | SE | tgatgactgtgggaaaggct (SEQ. I.D. NO. 25) |
| FVR464R | 135 | SE | ggaggcggaggttgtggtga (SEQ. I.D. NO. 26) |
| FVR465R | 2,459 | SE | cctccctcatcccatcttaa (SEQ. I.D. NO. 27) |
| FVR508F | 43 | SE | ccaaagcctccagcctgaga (SEQ. I.D. NO. 28) |
| FVR509R | 299 | SE | aggccgaggcgaacagatca (SEQ. I.D. NO. 29) |
| FVR510F | 327 | SE | gctgggattacaggcgtgaa (SEQ. I.D. NO. 30) |
| FVR511F | 1,343 | SE | tcaagcagtgaactctacct (SEQ. I.D. NO. 31) |
| FVR512R | 1,466 | SE | aactctattaatttacatgc (SEQ. I.D. NO. 32) |
| FVR513F | 1,499 | SE, PAC | aacaatggtgaacatggaca (SEQ. I.D. NO. 33) |
| FVR514R | 1,817 | SE, PAC | tcactacatttatgaggcaa (SEQ. I.D. NO. 34) |
| FVR515F | 1,888 | SE | ccatgagacaacttgattat (SEQ. I.D. NO. 35) |
| FVR516F | 2,098 | SE | gcgtgatagtttgtagttta (SEQ. I.D. NO. 36) |
| FVR517F | 2,298 | SE | cgaccagaactaaaatgcaa (SEQ. I.D. NO. 37) |
| FVR518F | 2,597 | SE | agatgtctcgttctgttgt (SEQ. I.D. NO. 38) |
| FVR519F | 2,864 | SE | tgcctgactcttgcccaaat (SEQ. I.D. NO. 39) |
| FVR660F | 537 | CL | atcgtcagcgacataggtcaatggaattttctctgat (SEQ. I.D. NO. 40) |
| FVR661R | 1,880 | CL | ataagaatgcggccgctgttgtctcatggactggaag (SEQ. I.D. NO. 41) |
| FVR662F | 445 | CL | ataagaatgcggccgcctatgaatgagtatcctaaaa (SEQ. I.D. NO. 42) |
| FVR663R | 728 | CL | cggatacagcatagcgtagaaaaggcagtgtggtc (SEQ. I.D. NO. 43) |
| FVR1043F | 438 | CL | cgtggatccgaaaagatatgaatgagtat (SEQ. I.D. NO. 44) |
| FVR1044F | 1,052 | CL | cctctcgagcaaagttcacatttatagag (SEQ. I.D. NO. 45) |
| FVR1045R | 1,050 | CL | ggaattcgcctctataaatgtgaactt (SEQ. I.D. NO. 46) |
| FVR1046R | 1,900 | CL | ccgctcgagaagttaaagagaataatcaa (SEQ. I.D. NO. 47) |
| FVR1237F | 447 | CL | ggaattctgaatgagtatcctaaaaaa (SEQ. I.D. NO. 48) |
| FVR1238R | 729 | CL | atgcatgctgtagaaaaggcagtgtggt (SEQ. I.D. NO. 49) |
| FVR1240F | 526 | CL | cgtcgcggccctgcagatggattcaatgga (SEQ. I.D. NO. 50) |
| FVR1242R | 1,933 | CL | tccccccggggggatgaatttattattta (SEQ. I.D. NO. 51) |
| FVR1411F | 447 | CL | tccccccgggtatgaatgagtatcctaaaaaa (SEQ. I.D. NO. 52) |

TABLE 1-continued

PRIMERS USED FOR CHARACTERIZATION OF THE HUMAN ANC_2H01 CDNA

| Primer[a] | Position[b] | Application[c] | Sequence 5'→3'[d] |
|---|---|---|---|
| FVR1412R | 1,033 | CL | aaaagtcgacggccactgctattagctctc (SEQ. I.D. NO. 53) |
| FVR1413F | 1,053 | CL | ggaattcttctataaatgtgaactttgt (SEQ. I.D. NO. 54) |
| FVR1414R | 1,900 | CL | aaaagtcgacaagttaaagagaataatcaa (SEQ. I.D. NO. 55) |

Legend to Table 1:
[a] R (Reverse) and F (Forward) refers to the sense or antisense orientation of the primers.
[b] The position of the most 5' nucleotide is given. Sequences are numbered according to the cDNA starting from the putative transcription initiation site (FIG. 1).
[c] Application of the primers: RA, 5' RACE; PAC, PCR isolation of a PAC clone; SE, sequencing; CL, cloning of cDNA fragments.
[d] Restriction sites added are underlined and in bold.
5' RACE primer set #1: FVR359R + FVR239F (Table 3)
5' RACE primer set #2: FVR360R + FVR240R (Table 3)

TABLE 2

Primers used for sequencing the inserts of two-hybrid vectors

| Primer | Vector | Sequence 5'→3' |
|---|---|---|
| FVR174F | pGAD424/pGAD10 | accactacaatggatgatgt (SEQ. I.D. NO. 56) |
| FVR175F | pGBT9/pAS2 | atcatcggaagagagtagta (SEQ. I.D. NO. 57) |
| FVR192R | pGAD424/pGAD10 | taaaagaaggcaaaacgatg (SEQ. I.D. NO. 58) |
| FVR217R | pGBT9/pAS2 | aaaatcataaatcataagaa (SEQ. I.D. NO. 59) |

TABLE 3

Primers used for 5' race

| Primer | Application | Sequence 5'→3' |
|---|---|---|
| FVR239F | 5' RACE | gaattcgtcgactagtacgggiigggiigggiig (SEQ. I.D. NO. 60) |
| FVR240F | 5' RACE | gaattcgtcgactagtac (SEQ. I.D. NO. 61) |

TABLE 4

Primers used for in-frame cloning of αN-catenin into pGBT9 and pAS2 vectors

| Primer | Position | Application | Sequence 5'→3'[a] |
|---|---|---|---|
| FVR137F | 39 | PCR, CL | acccccggggcaacttcacctatcattc (SEQ. I.D. NO. 62) |
| FVR138R | 1249 | PCR, CL | gccgccgccttccttttcattttccgctctt (SEQ. I.D. NO. 63) |

[a] Restriction sites added are underlined and in bold.

TABLE 5

M13F/R primers used for sequencing the inserts of pGEM ®-T clones

| Primer | Application | Sequence 5'→3' |
|---|---|---|
| FVR283R | SE | cgccagggttttcccagtcacgac (SEQ. I.D. NO. 64) |
| FVR284R | SE | tcacacaggaaacagctatgac (SEQ. I.D. NO. 65) |

TABLE 6

Primers used for sequencing or cloning of αE/αN-chimeras in pGBT9 two-hybrid vector

| Primer[a] | Application[b] | Sequence 5'→3'[c] |
|---|---|---|
| FVR51F | SE | cgttccgatctctatactgc (SEQ. I.D. NO. 66) |
| FVR54R | SE | atttgagtgacgaacagtgt (SEQ. I.D. NO. 67) |
| FVR157R | SE | ctggtcttcttggtcatttta (SEQ. I.D. NO. 68) |
| FVR160R | SE | ttcagatggtggcagtagag (SEQ. I.D. NO. 69) |
| FVR332R | SE | caacagatgcagccaaaaca (SEQ. I.D. NO. 70) |
| FVR738F | SE | ttggtattgattgaagctgc (SEQ. I.D. NO. 71) |
| FVR1157R | SE | tcagaagcaggacgagcgt (SEQ. I.D. NO. 72) |
| FVR1241F | PCR/CL | cggaattccgggggcaacttc (SEQ. I.D. NO. 73) |
| FVR1243R | PCR/CL | tcattaagagcatatgccagct (SEQ. I.D. NO. 74) |
| FVR1244F | PCR/CL | aattccccgggcgcccagctagc (SEQ. I.D. NO. 75) |
| FVR1245R | PCR/CL | tcctccagggacggccgaaagc (SEQ. I.D. NO. 76) |
| FVR1246F | PCR/CL | aggttccggccgtccctgca (SEQ. I.D. NO. 77) |
| FVR1247R | PCR/CL | ggaatatcggtacctgctcagc (SEQ. I.D. NO. 78) |
| FVR1248F | PCR/CL | gctgagcaggtaccgatattcc (SEQ. I.D. NO. 79) |
| FVR1249R | PCR/CL | ttggctgcaggtcgacggtatc (SEQ. I.D. NO. 80) |
| FVR1250F | PCR/CL | actggcatatgcactcaataac (SEQ. I.D. NO. 81) |
| FVR1251R | PCR/CL | cctggaagctgggtacctgttc (SEQ. I.D. NO. 82) |
| FVR1252F | PCR/CL | aacaggtacccagcttccagg (SEQ. I.D. NO. 83) |
| FVR1253R | PCR/CL | cttggctgcaggtcgactct (SEQ. I.D. NO. 84) |
| FVR1311F | SE | ctgtgtccccaggtcatcaa (SEQ. I.D. NO. 85) |
| FVR1427F | PCR/CL | tgctggcatatgtcttaatgagt (SEQ. I.D. NO. 86) |
| FVR1428F | PCR/CL | ctttcggccgtccctgga (SEQ. I.D. NO. 87) |
| FVR1479F | SE | ttgcctcttgtgaagtctgt (SEQ. I.D. NO. 88) |
| FVR1543F | PCR/CL | tgaccaagaagactcgcgactt (SEQ. I.D. NO. 89) |
| FVR1544F | PCR/CL | aaaactcgcgatctaaggagac (SEQ. I.D. NO. 90) |

TABLE 6-continued

Primers used for sequencing or cloning of αE/αN-chimeras in pGBT9 two-hybrid vector

| Primer[a] | Application[b] | Sequence 5'→3'[c] |
|---|---|---|
| FVR1545R | PCR/CL | ctgtctccttagatcgcgagttttc (SEQ. I.D. NO. 91) |
| FVR1546R | PCR/CL | gcaagtcgcgagtcttctt (SEQ. I.D. NO. 92) |
| FVR1552F | PCR/CL | ttgctctccgcggttacc (SEQ. I.D. NO. 93) |
| FVR1553R | PCR/CL | aaatcagcaaacgagtaaccgcggagagc (SEQ. I.D. NO. 94) |
| FVR1554R | PCR/CL | aagacggccgaaagcgctcc (SEQ. I.D. NO. 95) |
| FVR1778F | PCR/CL | ttattatatggcggccgctagaggaatc (SEQ. I.D. NO. 96) |
| FVR1779F | PCR/CL | ttattatattgcggccgctagagggct (SEQ. I.D. NO. 97) |
| FVR1780R | PCR/CL | atatttaatgcggccgccatctcatcc (SEQ. I.D. NO. 98) |
| FVR1781R | PCR/CL | gattcctctagcggccgccatctgatca (SEQ. I.D. NO. 99) |
| FVR2116F | PCR/CL | gcagctcgagcattcacgtag (SEQ. I.D. NO. 100) |

Legend to Table 6:
[a]R (Reverse) and F (Forward) refers to the sense or antisense orientation of the primers.
[b]Application of the primers: SE, sequencing; PCR/CL, cloning of cDNA fragments obtained by PCR.
[c]Restriction sites added are underlined and in bold.

TABLE 7

Human EST clones with high sequence homology to ANC_2H01

| EST-ID | Clone ID | NCBI-ID | Genbank-ID | P-score | Identification | Tissue |
|---|---|---|---|---|---|---|
| ab05b04.r1 | 839887 (5') | 1135840 | AA489897 | 6.50E-14 | Alu | fetal retina |
| ab05b04.s1 | 839887 (3') | 1135995 | AA490052 | 3.10E-11 | Alu | fetal retina |
| csg3803.seq.F | (5') | 887418 | AA247561 | | | fetal heart |
| EST57588 | (3') | 991663 | AA350356 | 5.50E-130 | | infant brain |
| EST67224 | (3') | 999664 | AA358286 | | | fetal lung |
| EST67225 | (5') | 999665 | AA358287 | | | fetal lung |
| HSC11E041 | c-11e04 | 69947 | Z43037 | 1.50E-122 | Zinc finger protein ZFB | total brain |
| HSC11E042 | c-11e04 | 101413 | F02513 | 7.20E-127 | | total brain |
| HSC1EA091 | c-1ea09 | 70401 | Z43511 | 4.90E-132 | | total brain |
| K7955F | K7955 (5') | 495454 | N89115 | | | fetal heart |
| ne31a10.s1 | 898938 | 1124854 | AA480224 | 7.20E-156 | | colon |
| nf73b05.s1 | 925521 | 1178920 | AA533630 | 7.30E-207 | Zinc finger protein ZFY | colon |
| ng37a06.s1 | 936946 | 1172028 | AA527388 | 1.50E-186 | Zinc finger protein ZFY | colon |
| nw21f01.s1 | 1241113 | 1422454 | AA715741 | 2.90E-109 | | germinal center B-cells |
| oa66d02.s1 | 1317219 | 1490202 | AA768457 | 9.70E-124 | | germinal center B-cells |
| o106d04.s1 | 1522663 (3') | 1636867 | AA908795 | 6.60E-194 | Zinc finger protein ZFY | lung |
| ot93e03.r1 | 1624348 (5') | 1731506 | AA993815 | 2.20E-184 | Zinc finger protein ZFY | total fetus |
| qc98a12.x1 | 1722238 (3') | | A1192390 | | Zinc finger Y protein 1 | |
| yg31a01.r1 | 33839 (5') | 189793 | R19999 | 1.04E-10 | Zinc finger protein ZFB | infant brain |
| yg31a01.s1 | 33839 (3') | 231207 | R44816 | 2.80E-89 | | infant brain |
| yj09h10.r1 | 148291 (5') | 273735 | H13821 | 3.90E-92 | Zinc finger protein ZFY | placenta |
| yj09h10.s1 | 148291 (3') | 273736 | H13822 | | | placenta |
| yj69f05.r1 | 154017 (5') | 218969 | R48904 | 1.80E-141 | Zinc finger protein ZFY | breast |
| ym44f07.r1 | 51032 (5') | 278981 | H19043 | | | infant brain |
| ym44f07.s1 | 51032 (3') | 279271 | H19333 | | | infant brain |
| ym60c04.r1 | 52828 (5') | 289963 | H29404 | 1.60E-100 | | infant brain |
| ym60c04.s1 | 52828 (3') | 289870 | H29311 | 3.10E-07 | Zinc finger protein ZFX | infant brain |
| yt86a03.r1 | 231148 (5') | 354596 | H53370 | 7.60E-09 | Zinc finger protein ZFB | pineal gland |
| yy74d04.r1 | 279271 (5') | 452804 | N47275 | 5.10E-89 | | multiple sclerosis lesions |
| zb42a04.r1 | 306222 (5') | 527257 | W20208 | | | parathyroid tumor |
| zc10d04.r1 | 321895 (5') | 545287 | W37576 | 9.20E-159 | | parathyroid tumor |
| zc10d04.s1 | 503447 (3') | 545171 | W31451 | 3.60E-135 | | parathyroid tumor |
| ze34d06.r1 | 360875 (5') | 622002 | AA011116 | 1.00E-117 | | retina |
| z130d12.r1 | 503447 (5') | 766757 | AA128260 | 2.70E-177 | | pregnant uterus |
| zo92b09.r1 | 594329 (5') | 803345 | AA164551 | 1.10E-135 | | ovarian cancer |
| zo92b09.s1 | 594329 (3') | 803346 | AA164552 | 2.00E-165 | | ovarian cancer |
| zr15c08.r1 | 663470 (5') | 863603 | AA224267 | | | brain |
| zr15c08.s1 | 663470 (3') | 863501 | AA224199 | 3.40E-174 | | brain |
| zs05b04.s1 | 684271 (3') | 875738 | AA236012 | 5.50E-192 | Zinc finger protein ZFY | germinal center B-cells |
| zs19b01.r1 | 685609 (5') | 902923 | AA261930 | 4.30E-52 | | germinal center B-cells |
| zs19b01.s1 | 685609 (3') | 896812 | AA255876 | 3.90E-134 | | germinal center B-cells |

TABLE 7-continued

Human EST clones with high sequence homology to ANC_2H01

| EST-ID | Clone ID | NCBI-ID | Genbank-ID | P-score | Identification | Tissue |
|---|---|---|---|---|---|---|
| zs38d06.r1 | 687461 (5') | 874883 | AA235027 | | | pooled melanocyte, fetal heart, pregnant uterus |
| zs38d06.s1 | 687467 (3') | 874768 | AA235044 | 4.90E-126 | Zinc finger protein ZFY | pooled melanocyte, fetal heart, pregnant uterus |
| zx10h09.r1 | 786113 (5') | 1093329 | AA448830 | 2.00E-120 | Zinc finger protein ZFX | total tetus |
| oy04b07.s1 | 1664821 (3') | | A1074908 | 3.00E-20 | Alu | senescent fibroblasts |
| qu12h01.x1 | 1964593 (3') | | A1287718 | 0 | Zinc finger proteln ZFX | |
| qt94f08.x1 | 1929951 (3') | | A1355794 | E-130 | | |
| qo34e04.x1 | 1910430 (3') | | A1348505 | 0 | Zinc finger protein ZFX | |

Legend to table 7:
EST-ID: identification number of EST (Expressed Sequence Tag);
Clone ID: identification number of the clone;
NCBI-ID: identification number according to NCBI database;
Genbank-ID: identification number according to the Genbank database;
P-score: index which indicates sequence homologies according to the BLAST algoritm (Altschul et al., 1990);
Identification: EST-clone feature;
Tissue: tissue used to isolate EST

TABLE 8

Mouse EST clones with high sequence homology to ANC_2H01

| EST-ID | Clone ID | NCBI-ID | Genbank-ID | P-score | Tissue |
|---|---|---|---|---|---|
| mh04b01.r1 | 441481 (5') | 627435 | AA013518 | | placenta |
| mh04f01.r1 | 441529 (5') | 627445 | AA013538 | 7.00E-117 | placenta |
| MM90D01 | 90D01 | 86891 | D28708 | | embryonal carcinoma cell line F9 |
| mn16c06.r1 | 538090 (5') | 759070 | AA120290 | 3.60E-165 | Beddington mouse embryonic region |
| vc56h04.s1 | 778615 (5') | 1057643 | AA413629 | 1.80E-17 | embryo |
| vc71e11.s1 | 780044 (5') | 1058954 | AA414940 | 1.70E-70 | embryo |
| vi05g03.r1 | 902932 (5') | 1162950 | AA518168 | 9.80E-135 | Barstead mouse myotubes MPLRB5 |
| vw14e12.r1 | 1243822 (5') | 1544529 | AA822672 | 2.40E-88 | thymus |
| vw50a07.r1 | 1247220 (5') | 1561565 | AA839433 | 1.20b-126 | mammary gland |
| vx63g07.r1 | 1279932 (5') | 1624581 | AA896550 | 4.70E-192 | macrophage |
| vy81c07.r1 | 1312620 (5') | 1662020 | AA931012 | 3.10E-108 | macrophage |
| mn16c06.y1 | 538090 (5') | | A1325780 | E-120 | Beddington mouse embryonic region |

Legend to table 8:
EST-ID: identification number of EST (Expressed Sequence Tag);
Clone ID: identification number of the clone;
NCBI-ID: identification number according to NCBI database;
Genbank-ID: identification number according to the Genbank database;
P-score: index which indicates sequence homologies according to the BLAST algoritm (Altschul et al., 1990);
Tissue: tissue used to isolate EST

TABLE 9 primers used for sequencing or cloning of ANC_2H01 fragments in the pGEX vectors

| Primer[a] | Application[b] | Sequence 5'→3'[c] |
|---|---|---|
| FVR357F | SE | gggctggcaagccacgtttggtg (SEQ. I.D. NO. 101) |
| FVR358R | SE | ccgggagctgcatgtgtcagagg (SEQ. I.D. NO. 102) |
| FVR1043F | PCR/CL | cgtggatccgaaaagatatgaatgagtat (SEQ. I.D. NO. 103) |
| FVR1044R | PCR/CL | cctctcgagcaaagttcacatttatagag (SEQ. I.D. NO. 104) |
| FVR1045F | PCR/CL | ggaattcgcctctataaatgtgaactt (SEQ. I.D. NO. 105) |
| FVR1046R | PCR/CL | ccgctcgagaagttaaagagaataatcaa (SEQ. I.D. NO. 152) |
| FVR1304R | PCR/CL | ccgctcgagagaggtgatcactaaaatg (SEQ. I.D. NO. 106) |
| FVR1305R | PCR/CL | cctctcgagcttatcacttaactctatta (SEQ. I.D. NO. 107) |
| FVR1306F | PCR/CL | ggaattctctattggtgtgaacagtgt (SEQ. I.D. NO. 108) |
| FVR1307F | PCR/CL | cggaattcgtaaaaacttctttgtatgt (SEQ. I.D. NO. 109) |

Legend to Table 9:
[a]R (Reverse) and F (Forward) refers to the sense or antisense orientation of the primers.
[b]Application of the primers: SE, sequencing; PCR/CL, cloning of cDNA fragments obtained by PCR.
[c]Restriction sites added are underlined and in bold.

TABLE 10 primers used for sequencing or cloning of ANC__2H01 fragments in the pCS2+ vectors

| Primer[a] | Application[b] | Sequence 5'→3'[c] |
|---|---|---|
| FVR63F | SE | taatacgactcactataggg (SEQ. I.D. NO. 110) |
| FVR736R | SE | tatttaggtgacactatag (SEQ. I.D. NO. 111) |
| FVR1686F | SE/PCR/CL | ccggaattcatgaatgagtatcctaaaaa (SEQ. I.D. NO. 112) |
| FVR1687R | PCR/CL | tgagtacgtagaaaaggcagtgtggtc (SEQ. I.D. NO. 113) |
| FVR1688F | PCR/CL | catgccatggatgagtatcctaaaaaaaga (SEQ. I.D. NO. 114) |
| FVR1689F | PCR/CL | catgccatggtctataaatgtgaactttgtga (SEQ. I.D. NO. 115) |
| FVR1690R | PCR/CL | catatccaagcctttcccacagtcatca (SEQ. I.D. NO. 116) |
| FVR1691F | PCR/CL | ccatcgatggattataaatgtgaactttgtga (SEQ. I.D. NO. 117) |

Legend to Table 10:
[a]R (Reverse) and F (Forward) refers to the sense or antisense orientation of the primers.
[b]Application of the primers: SE, sequencing; PCR/CL, cloning of cDNA fragments obtained by PCR.
[c]Restriction sites added are underlined and in bold.

TABLE 11 primers used for sequencing of ANC__2H01 constructs in the pEGFP vector

| Primer[a] | Application[b] | Sequence 5'→3'[c] |
|---|---|---|
| FVR1467R | SE | agggggaggtgtgggaggtttt (SEQ. I.D. NO. 118) |
| FVR1474F | SE | catggtcctgctggagttcgtg (SEQ. I.D. NO. 119) |

Legend to Table 11:
[a]R (Reverse) and F (Forward) refers to the sense or antisense orientation of the primers.
[b]Application of the primers: SE, sequencing; PCR/CL, cloning of cDNA fragments obtained by PCR.

TABLE 12 primers used for cloning of ANC__2H01 and αN-catenin mitochondrial targeted cDNA in the pcDNA3 vector

| Primer[a] | Application[b] | Sequence 5'→3'[c] |
|---|---|---|
| FVR1844F | PCR/CL | atcgtactcgaccccgggggaac (SEQ. I.D. NO. 120) |
| FVR1845R | PCR/CL | agcctctgggcccatcacaccagg (SEQ. I.D. NO. 121) |
| FVR1872F | PCR/CL | atcattgtactggccaagcagatg (SEQ. I.D. NO. 122) |
| FVR1873R | PCR/CL | gtccatctcgaggaaggaatccatt (SEQ. I.D. NO. 123) |

Legend to Table 12:
[a]R (Reverse) and F (Forward) refers to the sense or antisense orientation of the primers.
[b]Application of the primers: SE, sequencing; PCR/CL, cloning of cDNA fragments obtained by PCR.
[c]Restriction sites added are underlined and in bold.

TABLE 13 primers used for RT-PCR

| Primer[a] | Sequence 5'→3' |
|---|---|
| FVR1686F | ccggaattcatgaatgagtatcctaaaaa (SEQ. I.D. NO. 151) |
| FVR1687R | tgagtacgtagaaaaggcagtgtggtc (SEQ. I.D. NO. 152) |
| FVR1762F | ggtgcgactagggagaataggccgtgtacagcattgtg (SEQ. I.D. NO. 124) |
| FVR1826R | agggagcgcggccgcaacttcggcaactt (SEQ. I.D. NO. 125) |
| FVR1986F | gaaggtgaaggtcggagtc (SEQ. I.D. NO. 126) |
| FVR1987R | gaagatggtgatgggatttc (SEQ. I.D. NO. 127) |

Legend to Table 13:
[a]R (Reverse) and F (Forward) refers to the sense or antisense orientation of the primers.

References

Altschul, S. F., Warren, G., Miller, W., Myers, E. W., and Lipman, D. J. (1990) Basic local alignment search tool. J. Mol. Biol. 215, 403–410.

Bartel, P. L., Chien, C.-T., Stemglanz, R., and Fields, S. (1993). Using the two-hybrid system to detect protein-protein interactions. In Cellular Interactions in Development: A Practical Approach, D. A. Hartley, ed. (Oxford: Oxford University Press), pp. 153–179.

Beato, M., and Sánchez-Pacheco, A. (1996) Interaction of steroid hormone receptors with the transcription initiation complex. Endocr. Rev. 17, 587–609.

Becker, I., Becker, K. F., Röhrl, M. H., Minkus, G., Schütze, K., and Höfler, H. (1996). Single-cell mutation analysis of tumors from stained histologic slides. Lab. Invest. 75, 801–807.

Becker, K. F., Atkinson, M. J., Reich, U., Becker, I., Nekarda, H., Siewert, J. R., and Höfler, H. (1994). E-cadherin gene mutations provide clues to diffuse type gastric carcinomas. Cancer Res. 54, 3845–3852.

Behrens, J., Mareel, M. M., van Roy, F. M., and Birchmeier, W. (1989). Dissecting tumor cell invasion: Epithelial cells acquire invasive properties after the loss of uvomorulin-mediated cell-cell adhesion. J. Cell Biol. 108, 2435–2447.

Behrens, J., von Kries, J. P., Kühl, M., Bruhn, L., Wedlich, D., Grosschedl, R., and Birchmeier, W. (1996). Functional interaction of beta-catenin with the transcription factor LEF-1. Nature 382, 638–642.

Berx, G., Cleton-Jansen, A.-M., Nollet, F., de Leeuw, W. J. F., van de Vijver, M. J., Cornelisse, C., and van Roy, F. (1995). E-cadherin is a tumor/invasion suppressor gene mutated in human lobular breast cancers. EMBO J. 14, 6107–6115.

Berx, G., Cleton-Jansen, A.-M., Strumane, K., de Leeuw, W. J. F., Nollet, F., van Roy, F. M., and Cornelisse, C. (1996). E-cadherin is inactivated in a majority of invasive human lobular breast cancers by truncation mutations throughout its extracellular domain. Oncogene 13, 1919–1925.

Bonfield, J. K., Smith, K. F., and Staden, R. (1995). A new DNA sequence assembly program. Nucleic Acids Res. 23, 4992–4999.

Bracke, M. E., Van Larebeke, N. A., Vyncke, B. M., and Mareel, M. M. (1991). Retinoic acid modulates both invasion and plasma membrane ruffling of MCF-7 human mammary carcinoma cells in vitro, Br. J. Cancer 63, 867–872.

Braga, V. M. M., Machesky, L. M., Hall, A., and Hotchin, N. A. (1997) The small GTPases Rho and Rac are required for the establishment of cadherin-dependent cell-cell contacts. J. Cell Biol. 137, 1421–1431.

Braga, V. M. M. (1999) Small GTPases and regulation of cadherin dependent cell-cell adhesion. J. Clin. Pathol.—Mol. Pathol. 52, 197–202.

Braga, V. M. M., Del Maschio, A., Machesky, L., and Dejana, E. (1999) Regulation of cadherin function by Rho and Rac: Modulation by junction maturation and cellular context. Mol. Biol. Cell 10, 9–22.

Bubeck, P., Pistor, S., Wehland, J., and Jockusch, B. M. (1997). Ligand recruitment by vinculin domains in transfected cells, J. Cell Sci. 110, 1361–1371.

Bussemakers, M. J. G., Vandeven, W. J. M., Debruyne, F. M. J., and Schalken, J. A. (1991). Identification of High Mobility Group Protein I(Y) As Potential Progression Marker for Prostate Cancer by Differential Hybridization Analysis. Cancer Res. 51, 606–611.

Cerione, R. A., and Zheng, Y. (1996) The Dbl family of oncogenes. Curr. Opin. Cell Biol. 8, 216–222.

Chaganti, S. R., Chen, W. Parsa, N., Offit, K., Louie, D. C., Dalla-Favera, R. and Chaganti, R. S. (1998). Involvement of BCL6 in chromosomal aberrations affecting band 3 q27 in B-cell non-Hodgkin lymphoma. Genes Chromosomes and Cancer 23:323–327.

Claverie, J. M., Hardelin, J. P., Legouis, R., Levilliers, J., Bougueleret, L., Mattei, M. G., and Petit, C. (1993). Characterization and chromosomal assignment of a human cDNA encoding a protein related to the murine 102-kDa cadherin-associated protein (alpha-catenin). Genomics 15, 13–20.

Cowin, P. (1994). Unraveling the cytoplasmic interactions of the cadherin superfamily. Proc. Natl. Acad. Sci. U.S.A. 91, 10759–10761.

de Leij, L., Postmus, P. E., Buys, C. H. C. M., Elema, J. D., Ramaekers, F., Poppema, S., Brouwer, M., Van Der Veen, A. Y., and Mesander, G. (1985). Characterization of three new variant-type cell lines derived from small cell carcinoma of the lung. Cancer Res. 45, 6024–6033.

DuBridge, R. B., Tang, P., Hsia, H. C., Leong, P. M., Miller, J. H., and Calos, M. P. (1987). Analysis of mutation in human cells by using an Epstein-Barr virus shuttle system. Mol. Cell. Biol. 7, 379–387.

Frixen, U. H., Behrens, J., Sachs, M., Eberle, G., Voss, B., Warda, A., Löchner, D., and Birchmeier, W. (1991). E-cadherin-mediated cell-cell adhesion prevents invasiveness of human carcinoma cells. J. Cell Biol. 113, 173–185.

Georgopoulos, K., Winandy, S., and Avitahl, N. (1997). The role of the Ikaros gene in lymphocyte development and homeostasis. Annu. Rev. Immunol. 15, 155–176.

Gietz, D., St Jean, A., Woods, R. A., and Schiestl, R. H. (1992). Improved method for high efficiency transformation of intact yeast cells. Nucleic Acids Res. 20, 1425.

Görlich, D. and Mattaj, I. W. (1996). Nucleocytoplasmic transport. Science 271:1513–1518.

Graham, F. L., Smiley, J., Russell, W. C., and Naim, R. (1977). Characteristics of a human cell line transformed by DNA from human adenovirus type 5. J. Gen. Virol. 36, 59–72.

Habets, G. G. M., Scholtes, E. H. M., Zuydgeest, D., Van der Kammen, R. A., Stam, J. C., Bems, A., and Collard, J. G. (1994) Identification of an invasion-inducing gene, tiam-1, that encodes a protein with homology to GDP-GTP exchangers for Rho-like proteins. Cell 77, 537–549.

Hanas, J. S., Bogenhagen, D. F., and Wu, C. W. (1983a). Cooperative model for the binding of Xenopus transcription factor A to the 5S RNA gene. Proc. Natl. Acad. Sci. USA 80:2142–2145.

Hanas, J. S., Hazuda, D. J., Bogenhagen, D. F., Wu, F. Y., and Wu, C. W. (1983b). Xenopus transcription factor A requires zinc for binding to the 5S RNA gene. J. Biol. Chem. 258, 14120–14125.

He, T. C., Sparks, A. B., Rago, C., Hermeking, H., Zawel, L., da Costa, L. T., Morin, P. J., Vogelstein, B., and Kinzler, K. W. (1998). Identification of c-MYC as a target of the APC pathway. Science 281, 1509–1512.

Herrenknecht, K., Ozawa, M., Eckerskorn, C., Lottspeich, F., Lenter, M., and Kemler, R. (1991). The uvomorulin-anchorage protein alpha-catenin is a vinculin homologue. Proc. Natl. Acad. Sci. U.S.A. 88, 9156–9160.

Heusterspreute, M., Ha, T. V., Emery, S., Tournis-Gamble, S., Kennedy, N., and Davison, J. (1985). Vectors with restriction site banks.IV.pJRD184, a 3793-bp plasmid vector with 49 unique restriction sites. Gene 39, 299–304.

Hirano, S., Kimoto, N., Shimoyama, Y., Hirohashi, S., and Takeichi, M. (1992). Identification of a neural alpha-catenin as a key regulator of cadherin function and multicellular organization. Cell 70, 293–301.

Huber, O., Korn, R., McLaughlin, J., Ohsugi, M., Herrmann, B. G., and Kemler, R. (1996). Nuclear localization of beta-catenin by interaction with transcription factor LEF-1. Mech. Devel. 59, 3–10.

Ioannou, P.A. and de Jong, P.J. (1996). Construction of bacterial artificial chromosome libraries using the modified P1 (PAC) system. In: Current protocols in human genetics. Dracopoli, editor. Unit 5.15 Pub. John Wiley and Sons, New York.

James, L. A., Ogilvie, D. J., Yamakawa, K., Nakamura, Y., Stirling, C. J., and Anand, R. (1996). Walking, cloning, and mapping with YACs in 3q27: localization of five ESTs including three membrers of the cystatin gene family and identification of CpG islands. Genomics 32:425–430.

Janssens, B., Staes, K., and van Roy, F. (1999) Human alpha-catulin, a novel alpha-catenin-like molecule with conserved genomic structure, but deviating alternative splicing. Biochim. Biophys. Acta—Gene Struct. Expr. 1447, 341–347.

Kaibuchi, K., Kuroda, S., and Amano, M. (1999) Regulation of the cytoskeleton and cell adhesion by the Rho family GTPases in mammalian cells. Annu. Rev. Biochem. 68, 459–486.

Kalderon, D., Roberts, B. L., Richardson, W. D., and Smith, A. E. (1984). A short amino acid sequence able to specify nuclear location. Cell 39, 499–509.

Kemler, R. (1992). Classical cadherins. Semin. Cell Biol. 3, 149–155.

Kievits, T., Dauwerse, J. G., Wiegant, J., Devilee, P., Breuning, M. H., Cornelisse, C. J., Van Ommen, G. J., and Pearson, D. L. (1990). Rapid subchromosomal localization of cosmids by non-radioactive in situ hybridization. Cytogenet. Cell Genet. 53:134–136.

Knudson, A. G. (1985). Hereditary Cancer, Oncogenes, and Antioncogenes. Cancer Res. 45, 1437–1443.

Korman, N., Eyre, R. W., Klaus-Kovtun, V., and Stanley, J. R. (1989). Demonstration of an adhering junction molecule (plakoglobin) in the autoantigens of pemphigus foliaceous and pemphigus vulgaris. New Engl. J. Med. 321, 631–635.

Kowalczyk, A. P., Bornslaeger, E. A., Borgwardt, J. E., Palka, H. L., Dhaliwal, A. S., Corcoran, C. M., Denning, M. F., and Green, K. J. (1997). The amino-terminal domain of desmoplakin binds to plakoglobin and clusters desmosomal cadherin-plakoglobin complexes. J. Cell Biol. 139, 773–784.

Kozak, M. (1996). Interpreting cDNA sequences: Some insights from studies on translation. Mamm. Genome 7, 563–574.

Kozak, M. (1997). Recognition of AUG and alternative initiator codons is augmented by G in position +4 but is not generally affected by the nucleotides in positions +5 and +6. EMBO Journal. 16:2482–2492.

Kuroda, S., Fukata, M., Nakagawa, M., Fujii, K., Nakamura, T., Ookubo, T., Izawa, I., Nagase, T., Nomura, N., Tani, H., Shoji, I., Matsuura, Y., Yonehara, S., and Kaibuchi, K. (1998) Role of IQGAP1, a target of the small GTPases Cdc42 and Racl, in regulation of E-cadherin-mediated cell-cell adhesion. Science 281, 832–835.

Laemmli, U. K. (1970). Cleavage of structural proteins during the assembly of the head of bacteriophage T4. Nature 227, 680–685.

Love, J. J., Li, X., Case, D. A., Giese, K., Grosschedl, R., and Wright, P. E. (1995). Structural basis for DNA bending by the architectural transcription factor LEF-1. Nature 376, 791–795.

Mackay, D. J. G., and Hall, A. (1998) Rho GTPases. J. Biol. Chem. 273, 20685–20688.

Majumdar, M., Seasholtz, T. M., Buckmaster, C., Toksoz, D., and Brown, J. H. (1999) A Rho exchange factor mediates thrombin and Gal2-induced cytoskeletal responses. J. Biol. Chem. 274, 26815–26821.

Miller, J., McLachlan, A. D., and Klug, A. (1985). Repetitive zinc-binding domains in the protein transcription factor IIIA from Xenopus oocytes. EMBO J. 4, 1609–1614.

Miller, B. T., Rubino, D. M., Driggers, P. H., Haddad, B., Cisar, M., Gray, K., and Segars, J. H. (2000). Expression of Brx proto-oncogene in normal ovary and in epithelial ovarian neoplasms, Am J Obstet Gynecol 182, 286–95.

Mizushima, S., and Nagata, S. (1990). pEF-BOS: a powerful mammalian expression vector. Nucleic Acids Res. 18, 5322.

Morgan, B., Sun, L., Avitahl, N., Andrikopoulos, K., Ikeda, T., Gonzales, E., Wu, P., Neben, S., and Georgopoulos, K. (1997). Aiolos, a lymphoid restricted transcription factor that interacts with Ikaros to regulate lymphocyte differentiation. EMBO J. 16, 2004–2013.

Motoyama, T., and Watanabe, H. (1983). Carcinoembryonic antigen production in human gastric cancer cell lines in vitro and in nude mice. Gann 74(5), 679–686.

Mount, S. M. (1982). A catalogue of splice junction sequences, Nucleic Acid Res. 10, 459–472.

Nagafuchi, A., Takeichi, M., and Tsukita, S. (1991). The 102 kd cadherin-associated protein: Similarity to vinculin and posttranscriptional regulation of expression. Cell 65, 849–857.

Niwa, H., Yamamura, K., and Miyazaki, J. (1991). Efficient selection for high-expression transfectants with a novel eukaryotic vector, Gene 108, 193–9.

Oda, H., Uemura, T., Shiomi, K., Nagafuchi, A., Tsukita, S., and Takeichi, M. (1993). Identification of a Drosophila homologue of alpha-catenin and its association with the armadillo protein. J. Cell Biol. 121, 1133–1140.

Ozawa, M., Ringwald, M., and Kemler, R. (1990). Uvomorulin-catenin complex formation is regulated by a specific domain in the cytoplasmic region of the cell adhesion molecule. Proc. Natl. Acad. Sci. U.S.A. 87, 4246–4250.

Pavletich, N. P., and Pabo, C. O. (1991). Zinc Finger-DNA Recognition—Crystal Structure of a Zif268-DNA Complex at 2.1-A. Science 252, 809–817.

Pavletich, N. P., and Pabo, C. O. (1993). Crystal structure of a 5-finger GLI-DNA complex—new perspectives on zinc fingers. Science 261, 1701–1707.

Peifer, M. (1993). Cancer, catenins, and cuticle pattern—a complex connection. Science 262, 1667–1668.

Peifer, M. (1997). Cancer—beta-catenin as oncogene: The smoking gun. Science 275, 1752–1753.

Rimm, D. L., Kebriaei, P., and Morrow, J. S. (1994). Molecular cloning reveals alternative splice forms of human alpha(E)-catenin. Biochem. Biophys. Res. Commun. 203, 1691–1699.

Roth, M. B., Zahler, A. M., and Stolk, J. A. (1991). A conserved family of nuclear phosphoproteins localized to sites of polymerase II transcription, J Cell Biol 115, 587–96.

Rubino, D., Driggers, P., Arbit, D., Kemp, L., Miller, B., Coso, O., Pagliai, K., Gray, K., Gutkind, S., and Segars, J. (1998). Characterization of Brx, a novel Dbl family member that modulates estrogen receptor action, Oncogene 16, 2513–2526.

Sanger, F., Nicklen, S., and Coulson, A. (1981). DNA sequencing with chain-terminating inhibitors. Proc. Natl. Acad. Sci. U.S.A. 74, 5463.

Senoo, M. Seki, N., Ohira, M., Sugano, S., Watanabe, M., Tachibana, M., Tanaka, T., Shinkai, Y., Kato, H. (1998). A second p53-related protein, p73L, with high homology to p73. Biochem. Biophys. Res. Commun. 248:603–607.

Shapiro, M. B., and Senapathy, P. (1987). RNA splice junctions of different classes of eukaryotes: sequence statistics and functional implications in gene expression, Nucleic Acid Res. 15, 7155–7174.

Shibuya, Y, Yasuda, H., Tomatsuri, M., Mizoguchi, A., Takeichi, M., Shimada, K., and Ide, C. (1996). Alpha N-catenin expression in the normal and regenerating chick sciatic nerve. J. of Neurocytology. 25:615–624.

Sterpetti, P., Hack, A. A., Bashar, M. P., Park, B., Cheng, S. D., Knoll, J. H. M., Urano, T., Feig, L. A., and Toksoz, D. (1999) Activation of the Lbc Rho exchange factor proto-oncogene by truncation of an extended C terminus that regulates transformation and targeting (Vol 19, µg 1334, 1999). Mol. Cell. Biol. 19, 3930.

Su, L. K., Vogelstein, B., and Kinzler, K. W. (1993). Association of the APC tumor suppressor protein with catenins. Science 262, 1734–1737.

Sun, L., Liu, A., and Georgopoulos, K. (1996). Zinc finger-mediated protein interactions modulate ikaros activity, a molecular control of lymphocyte development. EMBO J. 15, 5358–5369.

Suzuki, S. T. (1996). Structural and functional diversity of cadherin superfamily: Are new members of cadherin superfamily involved in signal transduction pathway? J. Cell. Biochem. 61, 531–542.

Takaishi, K., Sasaki, T., Kotani, H., Nishioka, H., and Takai, Y. (1997) Regulation of cell-cell adhesion by Rac and Rho small G proteins in MDCK cells. J. Cell Biol. 139, 1047–1059.

Takeichi, M. (1991). Cadherin cell adhesion receptors as a morphogenetic regulator. Science 251, 1451–1455.

Tetsu, O., and McCormick, F. (1999). Beta-catenin regulates expression of cyclin D1 in colon carcinoma cells. Nature 398, 422–426.

Toksoz, D., and Williams, D. A. (1994) Novel human oncogene Lbc detected by transfection with distinct homology regions to signal transduction products. Oncogene 9, 621–628.

Turner, D. L., and Weintraub, H. (1994) Expression of achaete-scute homolog 3 in Xenopus embryos converts ectodermal cells to a neural fate. Genes Dev. 8, 1434–1447.

Uchida, N., Shimamura, K., Miyatani, S., Copeland, N. G., Gilbert, D. J., Jenkins, N. A., and Takeichi, M. (1994). Mouse alpha-N-catenin: Two isoforms, specific expression in the nervous system, and chromosomal localization of the gene. Dev. Biol. 163, 75–85.

Vleminckx, K., Vakaet Jr, L., Mareel, M., Fiers, W., and Van Roy, F. (1991). Genetic manipulation of E-cadherin expression by epithelial tumor cells reveals an invasion suppressor role. Cell 66, 107–119.

Wigler, M., Pellicer, A., Silverstein, S., and Axel, R. (1978). Biochemical transfer of single-copy eucaryotic genes using total cellular DNA as donor. Cell 14, 725–731.

Wright, W. E., Binder, M., and Funk, W. (1991). Cyclic amplification and selection of targets (CASTing) for the myogenin consensus binding site. Mol. Cell. Biol. 11, 4104–4110.

Yang, A., Kaghad M., Wang Y., Gillet E., Fleming M. D., Dotsch V., Andrews N. C., Caput D. and McKeon, F. (1998). P63, a p53 homolog at 3q27–29, encodes multiple products with transactivating death-inducing and dominant-negative activities. Moll. Cell. 2:305–316.

What is claimed is:

1. An isolated expression vector comprising an isolated nucleic acid sequence coding for a peptide sequence comprising SEQ ID NO: 2 or a fragment of SEQ ID NO: 2 that binds an αN-catenin protein.

2. The expression vector of claim 1, wherein said peptide sequence is SEQ ID NO: 2.

3. The expression vector of claim 1, wherein said fragment of SEQ ID NO: 2 comprises zinc finger fragments 4–9 corresponding to residues 289–483 of SEQ ID NO: 2.

4. The expression vector of claim 1, wherein said fragment of SEQ ID NO: 2 comprises zinc finger fragments 6–9 corresponding to residues 374–483 of SEQ ID NO: 2.

5. The expression vector of claim 1, wherein the fragment binds to the αN-catenin protein to form a complex in a cell that translocates to the cell's nucleus.

6. An isolated expression vector comprising a nucleic acid sequence encoding a protein of SEQ ID NO: 2 or a functional fragment of said protein that binds to an αN-catenin protein to form a complex in a cell, wherein said functional fragment of said protein consists of zinc finger fragments 4–9 corresponding to residues 289–483 of SEQ ID NO: 2.

7. An isolated expression vector comprising a nucleic acid sequence coding for a protein of SEQ ID NO: 2 or a functional fragment of said protein that binds to an αN-catenin protein to form a complex in a cell, wherein said functional fragment of said protein consists of zinc finger fragments 6–9 corresponding to residues 374–483 of SEQ ID NO: 2.

* * * * *

SEQUENCE LISTING

```
<160> NUMBER OF SEQ ID NOS: 158

<210> SEQ ID NO 1
<211> LENGTH: 3013
<212> TYPE: DNA
<213> ORGANISM: Homo sapiens
<220> FEATURE:
<221> NAME/KEY: CDS
<222> LOCATION: (446)..(1903)
<220> FEATURE:
<223> OTHER INFORMATION: 662-706 :  peptide used to raise polyclonal
      antibodies

<400> SEQUENCE: 1
caacgagttg tagccgcgga gagcaggcgt cgatgctggc gcccaaagcc tccagcctga      60
gagtcgcctc actcgtgtga cgacagagtt tcactcctgt tacccaggct ggaggacagt     120
gatgtgatct cgggtcacca caacctccgc ctcccggatt caggcgattc tcatgcctca     180
gcctcccgag tagctcagat tacaggcatg tgccaccacg cccggctaat tttgtatttt     240
cagtcgagac ggggtttccc catgttggtc aggctggtct tgaattcccg acctcaggtg     300
atctgttcgc ctcggcctcc caaagtgctg ggattacagg cgtgaaccac tgcacccggc     360
gaggcatttt ttactgtcta cagaaactta ttgtaattca ttttcctca ctccagtagt     420 aagaattata ccaaattgaa aagat atg aat gag tat cct aaa aaa aga aaa       472
                           Met Asn Glu Tyr Pro Lys Lys Arg Lys
                            1               5 agg aag act cta cac cct tct cgt tat tca gat tcc tct gga ata agc       520
Arg Lys Thr Leu His Pro Ser Arg Tyr Ser Asp Ser Ser Gly Ile Ser
 10              15                  20                  25 aga att gca gat gga ttc aat gga att ttc tct gat cat tgt tac agt       568
Arg Ile Ala Asp Gly Phe Asn Gly Ile Phe Ser Asp His Cys Tyr Ser
                 30                  35                  40 gtc tgt tct atg aga cag cca gat tta aaa tat ttt gac aac aaa gat       616
Val Cys Ser Met Arg Gln Pro Asp Leu Lys Tyr Phe Asp Asn Lys Asp
             45                  50                  55 gat gat tct gat acc gag acg tca aat gac ttg cca aaa ttt gca gat       664
Asp Asp Ser Asp Thr Glu Thr Ser Asn Asp Leu Pro Lys Phe Ala Asp
         60                  65                  70 gga atc aag gcc aga aac aga aat cag aac tac ctg gtt ccc agt cct       712
Gly Ile Lys Ala Arg Asn Arg Asn Gln Asn Tyr Leu Val Pro Ser Pro
     75                  80                  85 gta ctt aga att cta gac cac act gcc ttt tct aca gaa aaa tct gct       760
Val Leu Arg Ile Leu Asp His Thr Ala Phe Ser Thr Glu Lys Ser Ala
 90                  95                 100                 105 gat att gta att tgt gat gaa gag tgt gac tca cct gaa tca gtc aac       808
Asp Ile Val Ile Cys Asp Glu Glu Cys Asp Ser Pro Glu Ser Val Asn
                110                 115                 120
```

```
cag caa acc caa gag gag agt cct ata gaa gtt cac act gct gaa gat     856
Gln Gln Thr Gln Glu Glu Ser Pro Ile Glu Val His Thr Ala Glu Asp
            125                 130                 135 gtt cca att gct gta gaa gtg cat gcg att tct gag gat tat gat ata     904
Val Pro Ile Ala Val Glu Val His Ala Ile Ser Glu Asp Tyr Asp Ile
        140                 145                 150 gag aca gaa aac aat tcc tct gag agt ctc caa gac caa act gat gaa     952
Glu Thr Glu Asn Asn Ser Ser Glu Ser Leu Gln Asp Gln Thr Asp Glu
    155                 160                 165 gaa ccg cca gct aaa ctt tgt aaa att ctt gac aag agc caa gct ttg    1000
Glu Pro Pro Ala Lys Leu Cys Lys Ile Leu Asp Lys Ser Gln Ala Leu
170                 175                 180                 185 aat gtg act gcc cag cag aaa tgg cct tta ctg aga gct aat agc agt    1048
Asn Val Thr Ala Gln Gln Lys Trp Pro Leu Leu Arg Ala Asn Ser Ser
                190                 195                 200 ggc ctc tat aaa tgt gaa ctt tgt gag ttt aac agc aaa tat ttt tct    1096
Gly Leu Tyr Lys Cys Glu Leu Cys Glu Phe Asn Ser Lys Tyr Phe Ser
            205                 210                 215 gac tta aag cag cat atg atc ctg aag cat aaa cgt act gat tca aat    1144
Asp Leu Lys Gln His Met Ile Leu Lys His Lys Arg Thr Asp Ser Asn
        220                 225                 230 gtg tgt cga gta tgc aag gaa agt ttc tct acc aat atg ctt ctg ata    1192
Val Cys Arg Val Cys Lys Glu Ser Phe Ser Thr Asn Met Leu Leu Ile
    235                 240                 245 gaa cat gcc aaa ctg cat gaa gag gat ccc tac att tgt aaa tac tgt    1240
Glu His Ala Lys Leu His Glu Glu Asp Pro Tyr Ile Cys Lys Tyr Cys
250                 255                 260                 265 gat tat aag aca gta att ttt gag aac ctc agc cag cac att gca gac    1288
Asp Tyr Lys Thr Val Ile Phe Glu Asn Leu Ser Gln His Ile Ala Asp
                270                 275                 280 acc cat ttt agt gat cac ctc tat tgg tgt gaa cag tgt gat gta cag    1336
Thr His Phe Ser Asp His Leu Tyr Trp Cys Glu Gln Cys Asp Val Gln
            285                 290                 295 ttc tcc tca agc agt gaa ctc tac cta cat ttc cag gag cac agc tgt    1384
Phe Ser Ser Ser Ser Glu Leu Tyr Leu His Phe Gln Glu His Ser Cys
        300                 305                 310 gat gaa cag tac ttg tgt cag ttc tgt gaa cat gaa act aat gat cca    1432
Asp Glu Gln Tyr Leu Cys Gln Phe Cys Glu His Glu Thr Asn Asp Pro
    315                 320                 325 gaa gac ttg cat agc cat gtg gta aat gag cat gca tgt aaa tta ata    1480
Glu Asp Leu His Ser His Val Val Asn Glu His Ala Cys Lys Leu Ile
330                 335                 340                 345 gag tta agt gat aag tat aac aat ggt gaa cat gga caa tat agc ctc    1528
Glu Leu Ser Asp Lys Tyr Asn Asn Gly Glu His Gly Gln Tyr Ser Leu
                350                 355                 360 tta agc aaa att acc ttt gac aaa tgt aaa aac ttc ttt gta tgt caa    1576
Leu Ser Lys Ile Thr Phe Asp Lys Cys Lys Asn Phe Phe Val Cys Gln
            365                 370                 375 gta tgt ggt ttt cgg agt aga ctt cac aca aat gtt aac agg cat gtt    1624
Val Cys Gly Phe Arg Ser Arg Leu His Thr Asn Val Asn Arg His Val
        380                 385                 390 gct att gaa cat aca aaa att ttt cct cat gtt tgt gat gac tgt ggg    1672
Ala Ile Glu His Thr Lys Ile Phe Pro His Val Cys Asp Asp Cys Gly
    395                 400                 405 aaa ggc ttt tca agt atg cta gaa tat tgc aag cat tta aat tca cat    1720
Lys Gly Phe Ser Ser Met Leu Glu Tyr Cys Lys His Leu Asn Ser His
410                 415                 420                 425 tta tct gaa ggg att tat tta tgt caa tat tgt gaa tat tca aca gga    1768
Leu Ser Glu Gly Ile Tyr Leu Cys Gln Tyr Cys Glu Tyr Ser Thr Gly
```

-continued

```
                430                 435                 440
caa att gaa gat ctt aaa att cat cta gat ttc aag cat tca gct gac      1816
Gln Ile Glu Asp Leu Lys Ile His Leu Asp Phe Lys His Ser Ala Asp
            445                 450                 455 ttg cct cat aaa tgt agt gac tgc ttg atg agg ttt gga aat gaa agg      1864
Leu Pro His Lys Cys Ser Asp Cys Leu Met Arg Phe Gly Asn Glu Arg
            460                 465                 470 gaa tta ata agt cac ctt cca gtc cat gag aca act tga ttattctctt       1913
Glu Leu Ile Ser His Leu Pro Val His Glu Thr Thr
    475                 480                 485 taacttacag aatgttagtt taaaataata aattcatcct ttttttggag atgattaaat    1973
ggatgattgt aaacacaact tatgaaatct gcctttaaca agtaactttt ttaaattata    2033
aaattttatt ggcattgctc cattttctgt atataaatat atctttaatg tggtattttc    2093
aattgcgtga tagtttgtag tttcaaccac tcttggtgac tgtcatcctg tttcttccat    2153
attctctgat ttcatgaatt gaaagaaac aaatgtattg aagaagtgag ctacagtttt     2213
ccttccttaa ccatgggtgc tagtaacttt ttaaaactca agacaagatt agttttttat    2273
gtgtgaagtc attaaattat tacacgacca gaactaaaat gcaatataca gttaagtcca    2333
cggatactcc cattaatgag aaataacact aggaagccac tattacagga agaaaagatt    2393
tggttttcat ggcagtctgt ttttttaaaa aaaaatttt gagccactat ctattgttga     2453 atatttaag atgggatgag ggaggaacta ataagggctt acacaataaa aaataactat     2513
atcataactc attcataact tgatgtttca ttttctgttg aggaaccata aattcattca    2573
cagacttaat attttttct tagagatggt ctcgttctgt tgtccaggat ggagtgcagt     2633
ggttgatcat agctcccggg ccgtagtctc ccaggctcga gcaatcctcc cacttcaccc    2693
tcctgcatag ctaggactac aggcatgtgg caccatgccc gctaagtttt taaatttctt    2753
gtagagatga gatctcgcta tgttgcccag gccagtctca aactcctgga ctcaagcaat    2813
cctcccacct tggccttcca aatcactggg attataggca tgagccatta tgcctgactc    2873
ttgcccaaat ttctgatgtc aaattgttca ttgacagaaa acccactgaa gtatttaaag    2933
ttaggaagat ctgggagata ggggttgctg gcatgaaaat gtataactta caacatttat    2993
taataaaatg ataaattagc                                                3013
```

<210> SEQ ID NO 2
<211> LENGTH: 485
<212> TYPE: PRT
<213> ORGANISM: Homo sapiens
<220> FEATURE:
<223> OTHER INFORMATION: 662-706 :  peptide used to raise polyclonal
      antibodies

<400> SEQUENCE: 2

```
Met Asn Glu Tyr Pro Lys Lys Arg Lys Arg Lys Thr Leu His Pro Ser
  1               5                  10                  15

Arg Tyr Ser Asp Ser Ser Gly Ile Ser Arg Ile Ala Asp Gly Phe Asn
                 20                  25                  30

Gly Ile Phe Ser Asp His Cys Tyr Ser Val Cys Ser Met Arg Gln Pro
             35                  40                  45

Asp Leu Lys Tyr Phe Asp Asn Lys Asp Asp Ser Asp Thr Glu Thr
         50                  55                  60

Ser Asn Asp Leu Pro Lys Phe Ala Asp Gly Ile Lys Ala Arg Asn Arg
 65                  70                  75                  80

Asn Gln Asn Tyr Leu Val Pro Ser Pro Val Leu Arg Ile Leu Asp His
```

```
                    85                  90                  95
Thr Ala Phe Ser Thr Glu Lys Ser Ala Asp Ile Val Ile Cys Asp Glu
                100                 105                 110
Glu Cys Asp Ser Pro Glu Ser Val Asn Gln Gln Thr Gln Glu Glu Ser
                115                 120                 125
Pro Ile Glu Val His Thr Ala Glu Asp Val Pro Ile Ala Val Glu Val
                130                 135                 140
His Ala Ile Ser Glu Asp Tyr Asp Ile Glu Thr Glu Asn Asn Ser Ser
145                 150                 155                 160
Glu Ser Leu Gln Asp Gln Thr Asp Glu Glu Pro Pro Ala Lys Leu Cys
                165                 170                 175
Lys Ile Leu Asp Lys Ser Gln Ala Leu Asn Val Thr Ala Gln Gln Lys
                180                 185                 190
Trp Pro Leu Leu Arg Ala Asn Ser Ser Gly Leu Tyr Lys Cys Glu Leu
                195                 200                 205
Cys Glu Phe Asn Ser Lys Tyr Phe Ser Asp Leu Lys Gln His Met Ile
                210                 215                 220
Leu Lys His Lys Arg Thr Asp Ser Asn Val Cys Arg Val Cys Lys Glu
225                 230                 235                 240
Ser Phe Ser Thr Asn Met Leu Leu Ile Glu His Ala Lys Leu His Glu
                245                 250                 255
Glu Asp Pro Tyr Ile Cys Lys Tyr Cys Asp Tyr Lys Thr Val Ile Phe
                260                 265                 270
Glu Asn Leu Ser Gln His Ile Ala Asp Thr His Phe Ser Asp His Leu
                275                 280                 285
Tyr Trp Cys Glu Gln Cys Asp Val Gln Phe Ser Ser Ser Ser Glu Leu
                290                 295                 300
Tyr Leu His Phe Gln Glu His Ser Cys Asp Glu Gln Tyr Leu Cys Gln
305                 310                 315                 320
Phe Cys Glu His Glu Thr Asn Asp Pro Glu Asp Leu His Ser His Val
                325                 330                 335
Val Asn Glu His Ala Cys Lys Leu Ile Glu Leu Ser Asp Lys Tyr Asn
                340                 345                 350
Asn Gly Glu His Gly Gln Tyr Ser Leu Leu Ser Lys Ile Thr Phe Asp
                355                 360                 365
Lys Cys Lys Asn Phe Phe Val Cys Gln Val Cys Gly Phe Arg Ser Arg
                370                 375                 380
Leu His Thr Asn Val Asn Arg His Val Ala Ile Glu His Thr Lys Ile
385                 390                 395                 400
Phe Pro His Val Cys Asp Asp Cys Gly Lys Gly Phe Ser Ser Met Leu
                405                 410                 415
Glu Tyr Cys Lys His Leu Asn Ser His Leu Ser Glu Gly Ile Tyr Leu
                420                 425                 430
Cys Gln Tyr Cys Glu Tyr Ser Thr Gly Gln Ile Glu Asp Leu Lys Ile
                435                 440                 445
His Leu Asp Phe Lys His Ser Ala Asp Leu Pro His Lys Cys Ser Asp
450                 455                 460
Cys Leu Met Arg Phe Gly Asn Glu Arg Glu Leu Ile Ser His Leu Pro
465                 470                 475                 480
Val His Glu Thr Thr
                485

<210> SEQ ID NO 3
```

-continued

```
<211> LENGTH: 24
<212> TYPE: PRT
<213> ORGANISM: Artificial Sequence
<220> FEATURE:
<223> OTHER INFORMATION: Description of Artificial Sequence:  zinc
      finger motif ZF1

<400> SEQUENCE: 3

Tyr Lys Cys Glu Leu Cys Glu Phe Asn Ser Lys Tyr Phe Ser Asp Leu
  1               5                  10                  15

Lys Gln His Met Ile Leu Lys His
             20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence:  zinc
      finger motif ZF2

<400> SEQUENCE: 4

Asn Val Cys Arg Val Cys Lys Glu Ser Phe Ser Thr Asn Met Leu Leu
  1               5                  10                  15

Ile Glu His Ala Lys Leu His
             20

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence:  zinc
      finger motif ZF3

<400> SEQUENCE: 5

Tyr Ile Cys Lys Tyr Cys Asp Tyr Lys Thr Val Ile Phe Glu Asn Leu
  1               5                  10                  15

Ser Gln His Ile Ala Asp Thr His
             20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence:  zinc
      finger motif ZF4

<400> SEQUENCE: 6

Tyr Trp Cys Glu Gln Cys Asp Val Gln Phe Ser Ser Ser Ser Glu Leu
  1               5                  10                  15

Tyr Leu His Phe Gln Glu His
             20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence:  zinc
      finger motif ZF5

<400> SEQUENCE: 7

Tyr Leu Cys Gln Phe Cys Glu His Glu Thr Asn Asp Pro Glu Asp Leu
  1               5                  10                  15
```

His Ser His Val Val Asn Glu His
            20

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: zinc
      finger motif ZF6

<400> SEQUENCE: 8

Phe Val Cys Gln Val Cys Gly Phe Arg Ser Arg Leu His Thr Asn Val
  1               5                  10                  15

Asn Arg His Val Ala Ile Glu His
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: zinc
      finger motif ZF7

<400> SEQUENCE: 9

His Val Cys Asp Asp Cys Gly Lys Gly Phe Ser Ser Met Leu Glu Tyr
  1               5                  10                  15

Cys Lys His Leu Asn Ser His
            20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: zinc
      finger motif ZF8

<400> SEQUENCE: 10

Tyr Leu Cys Gln Tyr Cys Glu Tyr Ser Thr Gly Gln Ile Glu Asp Leu
  1               5                  10                  15

Lys Ile His Leu Asp Phe Lys His
            20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: zinc
      finger motif ZF9

<400> SEQUENCE: 11

His Lys Cys Ser Asp Cys Leu Met Arg Phe Gly Asn Glu Arg Glu Leu
  1               5                  10                  15

Ile Ser His Leu Pro Val His
            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: primer

```
      FVR274F

<400> SEQUENCE: 12
actgctgaag atgttccaat                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:  primer
      FVR291F

<400> SEQUENCE: 13
aggatcccta catttgtaaa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  primer
      FVR293F

<400> SEQUENCE: 14
ttgtgatgac tgtgggaaag                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  primer
      FVR308R

<400> SEQUENCE: 15
cctgggcaac atagcgagat                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  primer
      FVR309R

<400> SEQUENCE: 16
ggactctcct cttgggtttg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:  primer
      FVR310R

<400> SEQUENCE: 17
tctgtttctg gccttgattc                                               20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:  primer
      FVR345F
```

-continued

```
<400> SEQUENCE: 18
gcactatggc cagaaacaga aatcaga                                          27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer
      FVR346R

<400> SEQUENCE: 19
ggaattcctg ggcagtcaca ttcaaag                                          27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: primer
      FVR347R

<400> SEQUENCE: 20
ggaattccat atgctgcttt aagtcag                                          27

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer
      FVR359R

<400> SEQUENCE: 21
gcggttcttc atcagtttgg                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer
      FVR360R

<400> SEQUENCE: 22
ctcttgggtt tgctggttga                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer
      FVR421R

<400> SEQUENCE: 23
aacgagaagg gtgtagagtc                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: primer
      FVR462R
```

```
<400> SEQUENCE: 24
tcctgtaata gtggcttcct                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer
      FVR463F

<400> SEQUENCE: 25
tgatgactgt gggaaaggct                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer
      FVR464R

<400> SEQUENCE: 26
ggaggcggag gttgtggtga                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: primer
      FVR465R

<400> SEQUENCE: 27
cctccctcat cccatcttaa                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer
      FVR508F

<400> SEQUENCE: 28
ccaaagcctc cagcctgaga                                          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: primer
      FVR509R

<400> SEQUENCE: 29
aggccgaggc gaacagatca                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer
      FVR510F

<400> SEQUENCE: 30
```
gctgggatta caggcgtgaa                      20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: primer
      FVR511F

<400> SEQUENCE: 31
tcaagcagtg aactctacct                      20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: primer
      FVR512R

<400> SEQUENCE: 32
aactctatta atttacatgc                      20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: primer
      FVR513F

<400> SEQUENCE: 33
aacaatggtg aacatggaca                      20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: primer
      FVR514R

<400> SEQUENCE: 34
tcactacatt tatgaggcaa                      20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: primer
      FVR515F

<400> SEQUENCE: 35
ccatgagaca acttgattat                      20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: primer
      FVR516F

<400> SEQUENCE: 36

```
gcgtgatagt ttgtagttta                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer
      FVR517F

<400> SEQUENCE: 37
cgaccagaac taaaatgcaa                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: primer
      FVR519F

<400> SEQUENCE: 38
agatggtctc gttctgttgt                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: primer
      FVR519F

<400> SEQUENCE: 39
tgcctgactc ttgcccaaat                                              20

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: primer
      FVR660F

<400> SEQUENCE: 40
atcgtcagcg acataggtca atggaattt ctctgat                            37

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: primer
      FVR661R

<400> SEQUENCE: 41
ataagaatgc ggccgctgtt gtctcatgga ctggaag                           37

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: primer
      FVR662F

<400> SEQUENCE: 42
ataagaatgc ggccgctatg aatgagtatc ctaaaa                            36
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: primer
      FVR663R

<400> SEQUENCE: 43
cggatacagc atagcgtaga aaaggcagtg tggtc                    35

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: primer
      FVR1043F

<400> SEQUENCE: 44
cgtggatccg aaaagatatg aatgagtat                           29

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: primer
      FVR1044F

<400> SEQUENCE: 45
cctctcgagc aaagttcaca tttatagag                           29

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: primer
      FVR1045R

<400> SEQUENCE: 46
ggaattcgcc tctataaatg tgaactt                             27

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: primer
      FVR1046R

<400> SEQUENCE: 47
ccgctcgaga agttaaagag aataatcaa                           29

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: primer
      FVR1237F

<400> SEQUENCE: 48
ggaattcctg aatgagtatc ctaaaaaa                            28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: primer
      FVR1238R

<400> SEQUENCE: 49
atgcatgctg tagaaaaggc agtgtggt                                    28

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: primer
      FVR1240F

<400> SEQUENCE: 50
cgtcgcggcc ctgcagatgg attcaatgga                                  30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: primer
      FVR1242R

<400> SEQUENCE: 51
tccccccggg gggatgaatt tattatttta                                  30

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: primer
      FVR1411F

<400> SEQUENCE: 52
tcccccgggt atgaatgagt atcctaaaaa a                                31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: primer
      FVR1412R

<400> SEQUENCE: 53
aaaagtcgac ggccactgct attagctctc                                  30

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: primer
      FVR1413F

<400> SEQUENCE: 54
ggaattcttc tataaatgtg aactttgt                                    28

```
<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: primer
      FVR1414R

<400> SEQUENCE: 55
aaaagtcgac aagttaaaga gaataatcaa                                      30

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: primer
      FVR174F

<400> SEQUENCE: 56
accactacaa tggatgatgt                                                 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: primer
      FVR175F

<400> SEQUENCE: 57
atcatcggaa gagagtagta                                                 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: primer
      FVR192R

<400> SEQUENCE: 58 taaagaagg caaaacgatg                                                  20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: primer
      FVR217R

<400> SEQUENCE: 59
aaaatcataa atcataagaa                                                 20

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: primer
      FVR239F
<220> FEATURE:
<221> NAME/KEY: misc_feature
<222> LOCATION: (22)..(23)
<223> OTHER INFORMATION: modified-base:   inosine
<220> FEATURE:
<221> NAME/KEY: misc_feature
<222> LOCATION: (27)..(28)
```

<223> OTHER INFORMATION: modified-base: inosine
<220> FEATURE:
<221> NAME/KEY: misc_feature
<222> LOCATION: (32)..(33)
<223> OTHER INFORMATION: modified-base: inosine

<400> SEQUENCE: 60
gaattcgtcg actagtacgg gnngggnngg gnng                    34

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: primer
      FVR240F

<400> SEQUENCE: 61
gaattcgtcg actagtac                                      18

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: primer
      FVR137F

<400> SEQUENCE: 62 acccccggg ggcaacttca cctatcattc                          30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: primer
      FVR138R

<400> SEQUENCE: 63
gccgccgcct tcctttcat ttccgctctt                          30

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: primer
      FVR283

<400> SEQUENCE: 64
cgccagggtt ttcccagtca cgac                               24

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: primer
      FVR284

<400> SEQUENCE: 65
tcacacagga aacagctatg ac                                 22

<210> SEQ ID NO 66
<211> LENGTH: 21
<212> TYPE: DNA

```
<213> ORGANISM: Artificial Sequence
<220> FEATURE:
<223> OTHER INFORMATION: Description of Artificial Sequence: primer
      FVR51F

<400> SEQUENCE: 66
cgttccgatc tctatactg c                                          21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: primer
      FVR54R

<400> SEQUENCE: 67
atttgagtga cgaacagtgt                                           20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: primer
      FVR157R

<400> SEQUENCE: 68
ctggtcttct tggtcatttt a                                         21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: primer
      FVR160R

<400> SEQUENCE: 69
ttcagatggt ggcagtagag                                           20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: primer
      FVR332R

<400> SEQUENCE: 70
caacagatgc agccaaaaca                                           20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: primer
      FVR738F

<400> SEQUENCE: 71
ttggtattga ttgaagctgc                                           20

<210> SEQ ID NO 72
<211> LENGTH: 19
<212> TYPE: DNA
<213> ORGANISM: Artificial Sequence
```

```
<220> FEATURE:
<223> OTHER INFORMATION: Description of Artificial Sequence: primer
      FVR1157R

<400> SEQUENCE: 72
tcagaagcag gacgagcgt                                                    19

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: primer
      FVR1241F

<400> SEQUENCE: 73
cggaattccc gggggcaact tc                                                22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: primer
      FVR1243R

<400> SEQUENCE: 74
tcattaagag catatgccag ct                                                22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: primer
      FVR1244F

<400> SEQUENCE: 75
aattcccggg cgcccagcta gc                                                22

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: primer
      FVR1245R

<400> SEQUENCE: 76
tcctccaggg acggccgaaa gc                                                22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: primer
      FVR1246F

<400> SEQUENCE: 77
aggttccggc cgtccctgca                                                   20

<210> SEQ ID NO 78
<211> LENGTH: 22
<212> TYPE: DNA
<213> ORGANISM: Artificial Sequence
<220> FEATURE:
```

<223> OTHER INFORMATION: Description of Artificial Sequence: primer
      FVR1247R

<400> SEQUENCE: 78
ggaatatcgg tacctgctca gc                                              22

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: primer
      FVR1248F

<400> SEQUENCE: 79
gctgagcagg taccgatatt cc                                              22

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: primer
      FVR1249R

<400> SEQUENCE: 80
ttggctgcag gtcgacggta tc                                              22

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: primer
      FVR1250F

<400> SEQUENCE: 81
actggcatat gcactcaata ac                                              22

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: primer
      FVR1251R

<400> SEQUENCE: 82
cctggaagct gggtacctgt tc                                              22

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: primer
      FVR1252F

<400> SEQUENCE: 83
aacaggtacc cagcttccag g                                               21

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: primer -continued

FVR1253R

<400> SEQUENCE: 84
cttggctgca ggtcgactct                                               20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: FVR1311F

<400> SEQUENCE: 85
ctgtgtcccc aggtcatcaa                                               20

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: primer
      FVR1427F

<400> SEQUENCE: 86
tgctggcata tgctcttaat gagt                                          24

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: primer
      FVR1428F

<400> SEQUENCE: 87
ctttcggccg tccctgga                                                 18

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: primer
      FVR1479F

<400> SEQUENCE: 88
ttgcctcttg tgaagtctgt                                               20

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: primer
      FVR1543F

<400> SEQUENCE: 89
tgaccaagaa gactcgcgac tt                                            22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: primer
      FVR1544F

<400> SEQUENCE: 90
aaaactcgcg atctaaggag ac                                         22

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: primer
      FVR1545R

<400> SEQUENCE: 91
ctgtctcctt agatcgcgag ttttc                                      25

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: primer
      FVR1546R

<400> SEQUENCE: 92
gcaagtcgcg agtcttctt                                             19

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: primer
      FVR1552F

<400> SEQUENCE: 93
ttgctctccg cggttacc                                              18

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: primer
      FVR1553R

<400> SEQUENCE: 94
aaatcagcaa acgagtaacc gcggagagc                                  29

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: primer
      FVR1554R

<400> SEQUENCE: 95
aagacggccg aaagcgctcc                                            20

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: primer
      FVR1778F

<400> SEQUENCE: 96
ttattatatg gcggccgcta gaggaatc                              28

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: primer
      FVR1779F

<400> SEQUENCE: 97
ttattatatt gcggccgcta gagggct                               28

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: primer
      FVR1780R

<400> SEQUENCE: 98
atattttaat gcggccgcca tctcatcc                              28

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: primer
      FVR1781R

<400> SEQUENCE: 99
gattcctcta gcggccgcca tctgatca                              28

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: primer
      2116F

<400> SEQUENCE: 100
gcagctcgag tcattcacgt ag                                    22

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: primer
      FVR357F

<400> SEQUENCE: 101
gggctggcaa gccacgtttg gtg                                   23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: primer
      FVR358R

<400> SEQUENCE: 102
ccgggagctg catgtgtcag agg        23

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: primer
      FVR1043F

<400> SEQUENCE: 103
cgtggatccg aaaagatatg aatgagtat        29

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: primer
      FVR1044R

<400> SEQUENCE: 104
cctctcgagc aaagttcaca tttatagag        29

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence: primer
      FVR1045F

<400> SEQUENCE: 105
ggaattcgcc tctataaatg tgaactt        27

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: primer
      FVR1304R

<400> SEQUENCE: 106
ccgctcgaga gaggtgatca ctaaaatg        28

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: primer
      FVR1305R

<400> SEQUENCE: 107
cctctcgagc ttatcactta actctatta        29

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: primer
      FVR1306F

<400> SEQUENCE: 108
ggaattctct attggtgtga acagtgt        27

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: primer
      FVR1307F

<400> SEQUENCE: 109
cggaattcgt aaaaacttct ttgtatgt                                28

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: primer
      FVR63F

<400> SEQUENCE: 110
taatacgact cactataggg                                         20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: primer
      FVR736R

<400> SEQUENCE: 111
tatttaggtg acactatag                                          19

<210> SEQ ID NO 112
<211> LENGTH: 29
<212> TYPE: DNA
<213> ORGANISM: Artificial Sequence
<220> FEATURE:
<223> OTHER INFORMATION: Description of Artificial Sequence: primer
      FVR1686F

<400> SEQUENCE: 112
ccggaattca tgaatgagta tcctaaaaa                               29

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: primer
      FVR1687R

<400> SEQUENCE: 113
tgagtacgta gaaaaggcag tgtggtc                                 27

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: primer
      FVR1688F

<400> SEQUENCE: 114
catgccatgg atgagtatcc taaaaaaga                               30

```
<210> SEQ ID NO 115
<211> LENGTH: 32
<212> TYPE: DNA
<213> ORGANISM: Artificial Sequence
<220> FEATURE:
<223> OTHER INFORMATION: Description of Artificial Sequence: primer
      FVR1689F

<400> SEQUENCE: 115
catgccatgg tctataaatg tgaactttgt ga                                32

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: primer
      FVR1690R

<400> SEQUENCE: 116
catatccaag cctttcccac agtcatca                                     28

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: primer
      FVR1691F

<400> SEQUENCE: 117
ccatcgatgg attataaatg tgaactttgt ga                                32

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: primer
      FVR1467R

<400> SEQUENCE: 118 aggggggaggt gtgggaggtt tt                                          22

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: primer
      FVR1474F

<400> SEQUENCE: 119
catggtcctg ctggagttcg tg                                           22

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: primer
      FVR1844F

<400> SEQUENCE: 120
atcgtactcg agccccgggg gaac                                         24
```

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: primer FVR1845R

<400> SEQUENCE: 121
agcctctggg cccatcacac cagg                                    24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: primer FVR1872F

<400> SEQUENCE: 122
atcattgtac tggccaagca gatg                                    24

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: primer FVR1873R

<400> SEQUENCE: 123
gtccatctcg aggaaggaat ccatt                                   25

<210> SEQ ID NO 124
<211> LENGTH: 38
<212> TYPE: DNA
<213> ORGANISM: Artificial Sequence
<220> FEATURE:
<223> OTHER INFORMATION: Description of Artificial Sequence: primer FVR1762F

<400> SEQUENCE: 124
ggtgcgacta gggagaatag gccgtgtaca gcattgtg                     38

<210> SEQ ID NO 125
<211> LENGTH: 29
<212> TYPE: DNA
<213> ORGANISM: Artificial Sequence
<220> FEATURE:
<223> OTHER INFORMATION: Description of Artificial Sequence: primer FVR1826R

<400> SEQUENCE: 125
agggagcgcg gccgcaactt cggcaactt                               29

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: primer FVR1986F

<400> SEQUENCE: 126
gaaggtgaag gtcggagtc                                          19

<210> SEQ ID NO 127

```
<211> LENGTH: 20
<212> TYPE: DNA
<213> ORGANISM: Artificial Sequence
<220> FEATURE:
<223> OTHER INFORMATION: Description of Artificial Sequence: primer
      FVR1987R

<400> SEQUENCE: 127
gaagatggtg atgggatttc                                                  20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: primer
      FVR53F

<400> SEQUENCE: 128
cttcgggcct ctggaattta                                                  20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: primer
      FVR73R

<400> SEQUENCE: 129
cgacatcagg gtgctgtagg                                                  20

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: primer
      NM120

<400> SEQUENCE: 130
agcgctgcat ctccaggacc cgccggcgtt g                                     31

<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: primer
      NM121

<400> SEQUENCE: 131
cgcggatcct tatccggaag ttttactatc catagtgtcc                            40

<210> SEQ ID NO 132
<211> LENGTH: 639
<212> TYPE: DNA
<213> ORGANISM: Homo sapiens
<220> FEATURE:
<223> OTHER INFORMATION: Brx 3003-3641

<400> SEQUENCE: 132
ttttccggga catggctgag tgcagcaccc ctctcccaga ggattgctcc ccaacacata       60
gccctagagt tctcttccgc tccaacacag aagaggctct caaggagga cctttaatga      120 aaagtgcaat aaatgaggtg gagatccttc agggtttggt gagtggaaat ctgggaggca     180
```

```
cacttgggcc gactgtcagc agccccattg agcaagatgt ggtcggtccc gtttccctgc     240
cccggagagc agagaccttt ggaggatttg acagccatca gatgaatgct tcaaaaggag     300
gcgagaagga agaggagat gatggccaag atcttaggag aacggaatca gatagtggcc      360
taaaaaaggg tggaaatgct aacctggtat ttatgcttaa agaaacagt gagcaggttg      420 tccagagcgt tgttcatctc tacgagctcc tcagcgctct gcagggtgtg gtgctgcagc    480
aggacagcta cattgaggac cagaaactgg tgctgagcga gagggcgctc actcgcagct    540
tgtcccgccc gagctccctc attgagcagg agaagcagcg cagcctggag aagcagcgcc    600
aggacctggc caacctgcag aagcagcagg cccagtacc                           639
```

<210> SEQ ID NO 133
<211> LENGTH: 5640
<212> TYPE: DNA
<213> ORGANISM: Artificial Sequence
<220> FEATURE:
<223> OTHER INFORMATION: Description of Artificial Sequence: pLX32H-
    alpha-ctl-E clone

<400> SEQUENCE: 133

```
ttccggatct cgatcccgga aattaatacg actcactata gggagaccac aacggtttcc     60
ctctagaaat aattttgttt aactttaaga aggagatata catatgagcg ataaaattat    120
tcacctgact gacgacagtt ttgacacgga tgtactcaaa gcggacgggg cgatcctcgt    180
cgatttctgg gcagagtggt gcggtccgtg caaaatgatc gccccgattc tggatgaaat    240
cgctgacgaa tatcagggca aactgaccgt tgcaaaactg aacatcgatc aaaaccctgg    300
cactgcgccg aaatatggca tccgtggtat cccgactctg ctgctgttca aaaacggtga    360
agtggcggca accaaagtgg gtgcactgtc taaaggtcag ttgaaagagt tcctcgacgc    420
taacctggcc ggttctggtt ctggtgatga cgatgacaag agcgctgcat ctccaggacc    480
cgccggcgtt ggcggcgccg gagcagtcta cggctccggc tcttcgggct cgccctcga    540 ctcgggactg gagatcaaaa ctcgctcggt ggagcagacg ctactcccgc tggtttctca    600
gatcaccacg cttattaatc ataaagataa taccaaaaag tctgataaaa ctctgcaagc    660
aattcagcgt gtaggacaag ctgtcaactt ggcagttgga agatttgtta agtaggaga    720 agctatagcc aatgaaaact gggatttgaa agaagaaata aatattgctt gtattgaagc   780
taaacaagca ggagaaacaa ttgcagcact tacagacata accaacttga accatctgga   840
atctgatggg cagatcacaa ttttttacaga caaaacagga gtgataaagg ctgcaagatt   900
acttctttct tcagtgacaa agtgttgtt gctggcagac cgagtagtca ttaaacagat    960
aataacatca agaaataagg ttctcgcaac tatggaaaga ctagagaaag tgaatagctt  1020
tcaagagttt gtccaaatat tcagtcaatt tggaaatgaa atggtggagt tgcacatct   1080 gagtggagat agacaaaatg atttgaaaga tgaaaagaaa aagggcaaaaa tggcagcagc  1140 tagggcagtt cttgaaaagt gtacaatgat gcttctcaca gcttcaaaga catgtctgag  1200
gcatcctaac tgcgaatcag cccataaaaa caaagaagga gtatttgacc gtatgaaagt  1260
ggcattggat aaggtcattg aaattgtgac tgactgtaaa ccgaatggag agactgacat  1320
ttcatctatc agtattttta ctggaattaa ggaattcaag atgaatattg aagctcttcg  1380
ggagaatctt tattttcagt ccaaagagaa cctttctgtg acattggaag tcatcttgga  1440
gcgtatggag gactttactg attctgccta caccagccat gagcacagag aacgcatctt  1500
ggaactgtca actcaggcga gaatggaact gcagcagtta atttctgtgt ggattcaagc  1560
```

-continued

| | | |
|---|---|---|
| tcaaagcaag aaaacaaaaa gcatcgctga agaactggaa ctcagtatt tgaaaatcag | 1620 |
| tcacagtctt aatgaactta agaaagaact tcatagtaca gcgacacagc tggcagcaga | 1680 |
| tctattaaaa taccatgctg atcatgtggt tctaaaagca ttaaaactta ctggagtaga | 1740 |
| aggaaattta gaagctttgg ctgaatatgc ctgtaaactc tctgaacaga aagagcagct | 1800 |
| tgttgagacc tgtcgattgt tacgacacat atctgggaca gaacctctgg aaataacctg | 1860 |
| tatacatgca gaggagacat ttcaggtgac tggccaacag ataatttctg ctgctgaaac | 1920 |
| attgacattg catccatcta gtaaaattgc taaagaaaac ctagatgtat tttgtgaagc | 1980 |
| ttgggaatcc caaattagtg acatgtcaac actgctgaga gaaatcaatg acgtgtttga | 2040 |
| aggaagacga ggagagaagt atggctacct ttcacttcca aagccaatga gaataatgc | 2100 |
| aaacctgaaa tcattaaagc cagacaagcc tgactctgag gagcaagcca agatagcaaa | 2160 |
| gcttggactt aagctgggtt tgctcacctc tgacgctgac tgcgaaattg agaagtggga | 2220 |
| agatcaggag aatgagattg ttcaatatgg acggaacatg tccagtatgg cctattctct | 2280 |
| gtatttattt actagaggag aggggccact gaaaacttcc caggatttaa ttcatcaact | 2340 |
| agaggttttt gctgcagagg gtttaaagct tacttccagt gttcaagctt tttcaaaaca | 2400 |
| gctgaaagac gatgacaagc ttatgcttct cctggaaata aacaagctaa ttcctctatg | 2460 |
| ccaccagctc cagacagtaa ctaagacttc tttgcagaat aaagtatttc taaggttga | 2520 |
| caagtgtatt acgaagacaa gatccatgat ggctctctta gtccaacttc tttcactttg | 2580 |
| ttataaactg ctgaagaagc ttcagatgga aaataacgga tgggtctcag ttacaaataa | 2640 |
| ggacactatg gatagtaaaa cttccggagc gccggtgccg tatccagatc cgctggaacc | 2700 |
| acgtggcgcc taaggatccg agctcggtac caagcttatg catgcggccg catctagagg | 2760 |
| gcccggatcc ctcgaggtcg acgaattcga gctcggccga cttggccttc cctttagtga | 2820 |
| gggttaataa acttggtgag caataactag cataacccct tggggcctct aaacgggtct | 2880 |
| tgaggggttt tttgctgaaa ggaggaacta tatgcgctca tacgatatga acgttgagac | 2940 |
| tgccgctgag ttatcagtga gcaataacta gcataacccc ttggggcctc taaacgggtc | 3000 |
| ttgagggggtt ttttgctgaa aggaggaact atatccggcc ggatagctta tcgctagagg | 3060 |
| tcgaaattca cctcgaaagc aagctgataa accgatacaa ttaaaggctc ctttggagc | 3120 |
| ctttttttt ggagattttc aacgtgaaaa aattattatt cgcaattcca agctaattca | 3180 |
| cctcgaaagc aagctgataa accgatacaa ttaaaggctc cttttggagc ctttttttt | 3240 |
| ggagattttc aacgtgaaaa aattattatt cgcaattcca agctctgcct cgcgcgtttc | 3300 |
| ggtgatgacg gtgaaaacct ctgacacatg cagctcccta ggcaattgca tgtgagcaaa | 3360 |
| aggccagcaa aaggccagga accgtaaaaa ggccgcgttg ctggcgtttt tccataggct | 3420 |
| ccgcccccct gacgagcatc acaaaaatcg acgctcaagt cagaggtggc gaaacccgac | 3480 |
| aggactataa agataccagg cgtttccccc tggaagctcc ctcgtgcgct ctcctgttcc | 3540 |
| gaccctgccg cttaccggat acctgtccgc ctttctccct tcgggaagcg tggcgctttc | 3600 |
| tcatagctca cgctgtaggt atctcagttc ggtgtaggtc gttcgctcca agctgggctg | 3660 |
| tgtgcacgaa ccccccgttc agcccgaccg ctgcgcctta tccggtaact atcgtcttga | 3720 |
| gtccaacccg gtaagacacg acttatcgcc actggcagca gccactggta acaggattag | 3780 |
| cagagcgagg tatgtaggcg gtgctacaga gttcttgaag tggtggccta actacggcta | 3840 |
| cactagaagg acagtatttg gtatctgcgc tctgctgaag ccagttacct tcggaaaaag | 3900 |
| agttggtagc tcttgatccg gcaaacaaac caccgctggt agcggtggtt tttttgtttg | 3960 |

```
caagcagcag attacgcgca gaaaaaaagg atctcaagaa gatcctttga tcttttctac    4020
ggggtctgac gctcagtgga acgaaaactc acgttaaggg attttggtca tgagattatc    4080
aaaaaggatc ttcacctaga tccttttaaa ttaaaaatga agttttaaat caatctaaag    4140
tatatatgag taaacttggt ctgacagtta ccaatgctta atcagtgagg cacctatctc    4200
agcgatctgt ctatttcgtt catccatagt tgcctgactc cccgtcgtgt agataactac    4260
gatacgggag ggcttaccat ctggccccag tgctgcaatg ataccgcgag acccacgctc    4320
accggctcca gatttatcag caataaacca gccagccgga agggccgagc gcagaagtgg    4380
tcctgcaact ttatccgcct ccatccagtc tattaattgt tgccgggaag ctagagtaag    4440
tagttcgcca gttaatagtt tgcgcaacgt tgttgccatt gctgcaggca tcgtggtgtc    4500
acgctcgtcg tttggtatgg cttcattcag ctccggttcc caacgatcaa ggcgagttac    4560
atgatccccc atgttgtgca aaaaagcggt tagctccttc ggtcctccga tcgttgtcag    4620
aagtaagttg gccgcagtgt tatcactcat ggttatggca gcactgcata attctcttac    4680
tgtcatgcca tccgtaagat gcttttctgt gactggtgag tactcaacca agtcattctg    4740
agaatagtgt atgcggcgac cgagttgctc ttgcccggcg tcaacacggg ataataccgc    4800
gccacatagc agaactttaa aagtgctcat cattggaaaa cgttcttcgg ggcgaaaact    4860
ctcaaggatc ttaccgctgt tgagatccag ttcgatgtaa cccactcgtg cacccaactg    4920
atcttcagca tcttttactt tcaccagcgt ttctgggtga gcaaaaacag gaaggcaaaa    4980
tgccgcaaaa aagggaataa gggcgacacg gaaatgttga atactcatac tcttcctttt    5040
tcaatattat gtaagcagac agttttattg ttcatgatga tatattttta tcttgtgcaa    5100
tgtaacatca gagattttga gacacaacgt ggctttgttg aataaatcga acttttgctg    5160
agttgaagga tcagatcacg catcttcccg acaacgcaga ccgttccgtg caaagcaaa    5220 agttcaaaat caccaactgg tccacctaca acaaagctct catcaaccgt ggctccctca    5280
ctttctggct ggatgatggg gcgattcagg cctggtatga gtcagcaaca ccttcttcac    5340
gaggcagacc tcagcgccgg tgatgccggc cacgatgcgt ccggcgtaga ggatctctca    5400
cctaccaaac aatgccccc tgcaaaaaat aaattcatat aaaaaacata cagataacca    5460
tctgcggtga taaattatct ctggcggtgt tgacataaat accactggcg gtgatactga    5520
gcacatcagc aggacgcact gaccaccatg aaggtgacgc tcttaaaatt aagccctgaa    5580
gaagggcagc attcaaagca gaaggctttg gggtgtgtga tacgaaacga agcattggaa    5640
```

<210> SEQ ID NO 134
<211> LENGTH: 8033
<212> TYPE: DNA
<213> ORGANISM: Artificial sequence
<220> FEATURE:
<223> OTHER INFORMATION: Description of Artificial Sequence: pES31-
      alpha-ctl(47-2247)-E clone
<220> FEATURE:
<221> NAME/KEY: misc_feature
<222> LOCATION: (7362)..(7366)
<223> OTHER INFORMATION: modified-base:  n may be any nucleotide
<220> FEATURE:
<221> NAME/KEY: misc_feature
<222> LOCATION: (7761)..(7765)
<223> OTHER INFORMATION: modified-base:  n may be any nucleotide

<400> SEQUENCE: 134

```
gggagtcgct gcgttgcctt cgccccgtgc cccgctccgc gccgcctcgc gccgcccgcc      60
ccggctctga ctgaccgcgt tactcccaca ggtgagcggg cgggacggcc cttctcctcc     120
```

```
gggctgtaat tagcgcttgg tttaatgacg gctcgtttct tttctgtggc tgcgtgaaag    180
ccttaaaggg ctccgggagg gccctttgtg cggggggag cggctcgggg ggtgcgtgcg     240
tgtgtgtgtg cgtggggagc gccgcgtgcg gcccgcgctg cccggcggct gtgagcgctg    300
cgggcgcggc gcgggctttt gtgcgctccg cgtgtgcgcg aggggagcgc ggccgggggc    360
ggtgccccgc ggtgcggggg ggctgcgagg ggaacaaagg ctgcgtgcgg ggtgtgtgcg    420
tgggggggtg agcaggggggt gtgggcgcgg cggtcgggct gtaacccccc cctgcacccc   480
cctccccgag ttgctgagca cggcccggct tcgggtgcgg ggctccgtgc ggggcgtggc    540
gcggggctcg ccgtgccggg cggggggtgg cggcaggtgg gggtgccggg cggggcgggg    600
ccgcctcggg ccggggaggg ctcggggag gggcgcggcg gccccggagc gccggcggct     660
gtcgaggcgc ggcgagccgc agccattgcc ttttatggta atcgtgcgag agggcgcagg    720
gacttccttt gtcccaaatc tggcggagcc gaaatctggg aggcgccgcc gcaccccctc    780
tagcgggcgc gggcgaagcg gtgcggcgcc ggcaggaagg aaatgggcgg ggagggcctt    840
cgtgcgtcgc cgcgccgccg tccccttctc catctccagc ctcggggctg ccgcaggggg    900
acggctgcct tcggggggga cggggcaggg cggggttcgg cttctggcgt gtgaccggcg    960
ggntctagan cctctgctaa ccatgttcat gccttcttct ttttcctaca gctcctgggc   1020
aacgtgctgg ttattgtgct gtctcatcat tttggcaaag aattcctcga ccaccatgg    1080
ctgcatctcc aggacccgcc ggcgttggcg gcgccggagc agtctacggc tccggctctt   1140
cgggcttcgc cctcgactcg ggactggaga tcaaaactcg ctcggtggag cagacgctac   1200
tcccgctggt ttctcagatc accacgctta ttaatcataa agataatacc aaaaagtctg   1260
ataaaactct gcaagcaatt cagcgtgtag gacaagctgt caacttggca gttggaagat   1320
ttgttaaagt aggagaagct atagccaatg aaaactggga tttgaagaa gaaataaata    1380
ttgcttgtat tgaagctaaa caagcaggag aaacaattgc agcacttaca gacataacca   1440
acttgaacca tctggaatct gatgggcaga tcacaatttt tacagacaaa acaggagtga   1500
taaaggctgc aagattactt ctttcttcag tgacaaaagt gttgttgctg cagaccgag    1560
tagtcattaa acagataata acatcaagaa ataaggttct cgcaactatg aaagactag    1620
agaaagtgaa tagcttttcaa gagtttgtcc aaatattcag tcaatttgga aatgaaatgg   1680
tggagtttgc acatctgagt ggagatagac aaaatgattt gaaagatgaa aagaaaaagg   1740
caaaaatggc agcagctagg gcagttcttg aaaagtgtac aatgatgctt ctcacagctt   1800
caaagacatg tctgaggcat cctaactgcg aatcagccca taaaaacaaa aaggagtat    1860
ttgaccgtat gaaagtggca ttggataagg tcattgaaat tgtgactgac tgtaaaccga   1920
atggagagac tgacatttca tctatcagta tttttactgg aattaaggaa ttcaagatga   1980
atattgaagc tcttcgggag aatctttatt ttcagtccaa agagaacctt tctgtgacat   2040
tggaagtcat cttggagcgt atggaggact ttactgattc tgcctacacc agccatgagc   2100
acagagaacg catcttggaa ctgtcaactc aggcgagaat ggaactgcag cagttaattt   2160
ctgtgtggat tcaagctcaa agcaagaaaa caaaaagcat cgctgaagaa ctggaactca   2220
gtattttgaa aatcagtcac agtcttaatg aacttaagaa agaacttcat agtcacgca    2280
cacagctggc agcagatcta ttaaaatacc atgctgatca tgtggttcta aaagcattaa   2340
aacttactgg agtagaagga aattagaag ctttggctga atatgcctgt aaactctctg   2400
aacagaaaga gcagcttgtt gagacctgtc gattgttacg acacatatct gggacagaac   2460
```

```
ctctggaaat aacctgtata catgcagagg agacatttca ggtgactggc aacagataa    2520 tttctgctgc tgaaacattg acattgcatc catctagtaa aattgctaaa gaaaacctag   2580
atgtattttg tgaagcttgg gaatcccaaa ttagtgacat gtcaacactg ctgagagaaa   2640
tcaatgacgt gtttgaagga agacgaggag agaagtatgc ctacctttca cttccaaagc   2700
caatgaagaa taatgcaaac ctgaaatcat taaagccaga caagcctgac tctgaggagc   2760
aagccaagat agcaaagctt ggacttaagc tgggtttgct cacctctgac gctgactgcg   2820
aaattgagaa gtgggaagat caggagaatg agattgttca atatggacgg aacatgtcca   2880
gtatggccta ttctctgtat ttatttacta gaggagaggg gccactgaaa acttcccagg   2940
atttaattca tcaactagag gttttttgctg cagagggttt aaagcttact tccagtgttc   3000 aagcttttc aaaacagctg aaagacgatg acaagcttat gcttctcctg gaaataaaca   3060
agctaattcc tctatgccac cagctccaga cagtaactaa gacttctttg cagaataaag   3120
tatttctaaa ggttgacaag tgtattacga agacaagatc catgatggct ctcttagtcc   3180
aacttctttc actttgttat aaactgctga agaagcttca gatggaaaat aacggatggg   3240
tctcagttac aaataaggac actatggata gtaaaacttc cggagcgccg gtgccgtatc   3300
cagatccgct ggaaccacgt ggcgcctaag gatccgagct cggtaccaag cttaagttta   3360
aaccgctgat cagcctcgac tgtgccttct agttgccagc catctgttgt ttgcccctcc   3420
cccgtgcctt ccttgaccct ggaaggtgcc actcccactg tcctttccta ataaaatgag   3480
gaaattgcat cgcattgtct gagtaggtgt cattctattc tggggggtgg ggtggggcag   3540
gacagcaagg gggaggattg ggaagacaat agcaggcatg ctggggatgc ggtgggctct   3600
atggcttctg aggcggaaag aaccagctgg ggctctaggg ggtatcccca cgcgccctgt   3660
agcggcgcat taagcgcggc gggtgtggtg gttacgcgca gcgtgaccgc tacacttgcc   3720
agcgccctag cgcccgctcc tttcgctttc ttcccttcct ttctcgccac gttcgccggc   3780
tttccccgtc aagctctaaa tcgggggcatc cctttagggt tccgatttag tgctttacgg   3840
cacctcgacc ccaaaaaact tgattagggt gatggttcac gtagtgggcc atcgccctga   3900
tagacggttt ttcgcccttt gacgttggag tccacgttct ttaatagtgg actcttgttc   3960
caaactggaa caacactcaa ccctatctcg gtctattctt ttgatttata agggattttg   4020
gggatttcgg cctattggtt aaaaaatgag ctgatttaac aaaaatttaa cgcgaattaa   4080
ttctgtggaa tgtgtgtcag ttagggtgtg gaaagtcccc aggctcccca ggcaggcaga   4140
agtatgcaaa gcatgcatct caattagtca gcaaccaggt gtggaaagtc cccaggctcc   4200
ccagcaggca gaagtatgca aagcatgcat ctcaattagt cagcaaccat agtcccgccc   4260
ctaactccgc ccatcccgcc cctaactccg cccagttccg cccattctcc gccccatggc   4320
tgactaattt ttttttattta tgcagaggcc gaggccgcct ctgcctctga gctattccag   4380
aagtagtgag gaggcttttt tggaggccta ggcttttgca aaaagctccc gggagcttgt   4440
atatccattt tcggatctga tcagcacgtg ttgacaatta atcatcggca tagtatatcg   4500
gcatagtata atacgacaag gtgaggaact aaaccatggc caagttgacc agtgccgttc   4560
cggtgctcac cgcgcgcgac gtcgccggag cggtcgagtt ctggaccgac cggctcgggt   4620
tctcccggga cttcgtggag gacgacttcg ccggtgtggt ccgggacgac gtgaccctgt   4680
tcatcagcgc ggtccaggac caggtggtgc cggacaacac cctggcctgg gtgtgggtgc   4740
gcggcctgga cgagctgtac gccgagtggt cggaggtcgt gtccacgaac ttccgggacg   4800
cctccgggcc ggccatgacc gagatcggcg agcagccgtg ggggcgggag ttcgccctgc   4860
```

-continued

```
gcgacccggc cggcaactgc gtgcacttcg tggccgagga gcaggactga cacgtgctac   4920
gagatttcga ttccaccgcc gccttctatg aaaggttggg cttcggaatc gttttccggg   4980
acgccggctg gatgatcctc cagcgcgggg atctcatgct ggagttcttc gcccacccca   5040
acttgtttat tgcagcttat aatggttaca ataaagcaa tagcatcaca aatttcacaa    5100
ataaagcatt tttttcactg cattctagtt gtggtttgtc caaactcatc aatgtatctt   5160
atcatgtctg tataccgtcg acctctagct agagcttggc gtaatcatgg tcatagctgt   5220
ttcctgtgtg aaattgttat ccgctcacaa ttccacacaa catacgagcc ggaagcataa   5280
agtgtaaagc ctggggtgcc taatgagtga gctaactcac attaattgcg ttgcgctcac   5340
tgcccgcttt ccagtcggga aacctgtcgt gccagctgca ttaatgaatc ggccaacgcg   5400
cggggagagg cggtttgcgt attgggcgct cttccgcttc ctcgctcact gactcgctgc   5460
gctcggtcgt tcggctgcgg cgagcggtat cagctcactc aaaggcggta atacggttat   5520
ccacagaatc aggggataac gcaggaaaga acatgtgagc aaaaggccag caaaaggcca   5580
ggaaccgtaa aaaggccgcg ttgctggcgt ttttccatag gctccgcccc cctgacgagc   5640
atcacaaaaa tcgacgctca agtcagaggt ggcgaaaccc gacaggacta taaagatacc   5700
aggcgtttcc ccctggaagc tccctcgtgc gctctcctgt tccgaccctg ccgcttaccg   5760
gatacctgtc cgcctttctc ccttcgggaa gcgtggcgct ttctcaatgc tcacgctgta   5820
ggtatctcag ttcggtgtag gtcgttcgct ccaagctggg ctgtgtgcac gaaccccccg   5880
ttcagcccga ccgctgcgcc ttatccggta actatcgtct tgagtccaac ccggtaagac   5940
acgacttatc gccactggca gcagccactg gtaacaggat tagcagagcg aggtatgtag   6000
gcggtgctac agagttcttg aagtggtggc ctaactacgg ctacactaga aggacagtat   6060
ttggtatctg cgctctgctg aagccagtta ccttcggaaa aagagttggt agctcttgat   6120
ccggcaaaca aaccaccgct ggtagcggtg gtttttttgt ttgcaagcag cagattacgc   6180
gcagaaaaaa aggatctcaa gaagatcctt tgatctttc tacgggtct gacgctcagt    6240 ggaacgaaaa ctcacgttaa gggattttgg tcatgagatt atcaaaaagg atcttcacct   6300
agatcctttt aaattaaaaa tgaagtttta atcaatcta agtatatat gagtaaactt     6360 ggtctgacag ttaccaatgc ttaatcagtg aggcacctat ctcagcgatc tgtctatttc   6420
gttcatccat agttgcctga ctccccgtcg tgtagataac tacgatacgg gagggcttac   6480
catctggccc cagtgctgca atgataccgc gagacccacg ctcaccggct ccagatttat   6540
cagcaataaa ccagccagcc ggaagggccg agcgcagaag tggtcctgca actttatccg   6600
cctccatcca gtctattaat tgttgccggg aagctagagt aagtagttcg ccagttaata   6660
gtttgcgcaa cgttgttgcc attgctacag gcatcgtggt gtcacgctcg tcgtttggta   6720
tggcttcatt cagctccggt tcccaacgat caaggcgagt tacatgatcc cccatgttgt   6780
gcaaaaaagc ggttagctcc ttcggtcctc cgatcgttgt cagaagtaag ttggccgcag   6840
tgttatcact catggttatg gcagcactgc ataattctct tactgtcatg ccatccgtaa   6900
gatgcttttc tgtgactggt gagtactcaa ccaagtcatt ctgagaatag tgtatgcggc   6960
gaccgagttg ctcttgcccg gcgtcaatac gggataatac cgcgccacat agcagaactt   7020
taaaagtgct catcattgga aaacgttctt cggggcgaaa actctcaagg atcttaccgc   7080
tgttgagatc cagttcgatg taacccactc gtgcacccaa ctgatcttca gcatctttta   7140
ctttcaccag cgtttctggg tgagcaaaaa caggaaggca aaatgccgca aaaagggaa    7200
```

-continued

```
taagggcgac acggaaatgt tgaatactca tactcttcct ttttcaatat tattgaagca    7260
tttatcaggg ttattgtctc atgagcggat acatatttga atgtatttag aaaaataaac    7320 aaatagggt tccgcgcaca tttccccgaa aagtgccacc tgnnnnngtc gacattgatt     7380
attgactagt tattaatagt aatcaattac ggggtcatta gttcatagcc catatatgga    7440
gttccgcgtt acataactta cggtaaatgg cccgcctggc tgaccgccca acgaccccg     7500 cccattgacg tcaataatga cgtatgttcc catagtaacg ccaatagga ctttccattg     7560 acgtcaatgg gtggactatt tacggtaaac tgcccacttg gcagtacatc aagtgtatca    7620
tatgccaagt acgcccccta ttgacgtcaa tgacggtaaa tggcccgcct ggcattatgc    7680
ccagtacatg accttatggg actttcctac ttggcagtac atctacgtat tagtcatcgc    7740
tattaccatg gnnnnngtcg aggtgagccc cacgttctgc ttcactctcc ccatctcccc    7800
cccctcccca cccccaattt tgtatttatt tattttttaa ttatttttgtg cagcgatggg   7860 ggcggggggg ggggggcgc gcgccaggcg gggcggggcg gggcgagggg cggggcgggg    7920
cgaggcggag aggtgcggcg gcagccaatc agagcggcgc gctccgaaag tttccttta    7980 tggcgaggcg gcggcggcgg cggccctata aaaagcgaag cgcgcggcgg gcg           8033
```

<210> SEQ ID NO 135
<211> LENGTH: 180
<212> TYPE: PRT
<213> ORGANISM: Homo sapiens
<220> FEATURE:
<223> OTHER INFORMATION: alpha-E-catenin (121-301)

<400> SEQUENCE: 135

```
Arg Gly Asn Met Val Arg Ala Ala Arg Ala Leu Leu Ser Ala Val Thr
 1               5                  10                  15

Arg Leu Leu Ile Leu Ala Asp Met Ala Asp Val Tyr Lys Leu Leu Val
                20                  25                  30

Gln Leu Lys Val Val Glu Asp Gly Ile Leu Lys Leu Arg Asn Ala Gly
            35                  40                  45

Asn Glu Gln Asp Leu Gly Ile Gln Tyr Lys Ala Leu Lys Pro Glu Val
        50                  55                  60

Asp Lys Leu Asn Ile Met Ala Ala Lys Arg Gln Gln Glu Leu Lys Asp
    65                  70                  75                  80

Val Gly His Arg Asp Gln Met Ala Ala Arg Gly Ile Leu Gln Lys
                85                  90                  95

Asn Val Pro Ile Leu Tyr Thr Ala Ser Gln Ala Cys Leu Gln His Pro
            100                 105                 110

Asp Val Ala Ala Tyr Lys Ala Asn Arg Asp Leu Ile Tyr Lys Gln Val
        115                 120                 125

Gln Gln Ala Val Thr Gly Ile Ser Asn Ala Ala Gln Ala Thr Ala Ser
    130                 135                 140

Asp Asp Ala Ser Gln His Gln Gly Gly Gly Gly Glu Leu Ala Tyr
145                 150                 155                 160

Ala Leu Asn Asn Phe Asp Lys Gln Ile Ile Val Asp Pro Leu Ser Phe
                165                 170                 175

Ser Glu Glu Arg
            180
```

<210> SEQ ID NO 136
<211> LENGTH: 179
<212> TYPE: PRT
<213> ORGANISM: Homo sapiens

```
<220> FEATURE:
<223> OTHER INFORMATION: alpha-N-catenin (120-300)

<400> SEQUENCE: 136

Arg Gly Thr Met Val Arg Ala Ala Arg Ala Leu Leu Ser Ala Val Thr
  1               5                  10                  15

Arg Leu Leu Ile Leu Ala Asp Met Ala Asp Val Met Arg Leu Leu Ser
             20                  25                  30

His Leu Lys Ile Val Glu Glu Ala Leu Glu Ala Val Lys Asn Ala Thr
         35                  40                  45

Asn Glu Gln Asp Leu Ala Asn Arg Phe Lys Glu Phe Gly Lys Lys Met
     50                  55                  60

Val Lys Leu Asn Tyr Val Ala Ala Arg Gln Gln Glu Leu Lys Asp
 65                  70                  75                  80

Pro His Cys Arg Asp Glu Met Ala Ala Arg Gly Ala Leu Lys Lys
                 85                  90                  95

Asn Ala Thr Met Leu Tyr Thr Ala Ser Gln Ala Phe Leu Arg His Pro
                100                 105                 110

Asp Val Ala Ala Thr Arg Ala Asn Arg Asp Tyr Val Phe Lys Gln Val
            115                 120                 125

Gln Glu Ala Ile Ala Gly Ile Ser Asn Ala Ala Gln Ala Thr Ser Pro
        130                 135                 140

Thr Asp Glu Ala Lys Gly His Thr Gly Ile Gly Glu Leu Ala Ala Ala
145                 150                 155                 160

Leu Asn Glu Phe Asp Asn Lys Ile Ile Leu Asp Pro Met Thr Phe Ser
                165                 170                 175

Glu Ala Arg

<210> SEQ ID NO 137
<211> LENGTH: 240
<212> TYPE: PRT
<213> ORGANISM: Homo sapiens
<220> FEATURE:
<223> OTHER INFORMATION: alpha-N-catenin (359-598)

<400> SEQUENCE: 137

Gly Asp Pro Leu Asn Ile Ala Ile Asp Lys Met Thr Lys Lys Thr Arg
  1               5                  10                  15

Asp Leu Arg Arg Gln Leu Arg Lys Ala Val Met Asp His Ile Ser Asp
             20                  25                  30

Ser Phe Leu Glu Thr Asn Val Pro Leu Leu Val Leu Ile Glu Ala Ala
         35                  40                  45

Lys Ser Gly Asn Glu Lys Glu Val Lys Glu Tyr Ala Gln Val Phe Arg
     50                  55                  60

Glu His Ala Asn Lys Leu Val Glu Val Ala Asn Leu Ala Cys Ser Ile
 65                  70                  75                  80

Ser Asn Asn Glu Glu Gly Val Lys Leu Val Arg Met Ala Ala Thr Gln
                 85                  90                  95

Ile Asp Ser Leu Cys Pro Gln Val Ile Asn Ala Ala Leu Thr Leu Ala
                100                 105                 110

Ala Arg Pro Gln Ser Lys Val Ala Gln Asp Asn Met Asp Val Phe Lys
            115                 120                 125

Asp Gln Trp Glu Lys Gln Val Arg Val Leu Thr Glu Ala Val Asp Asp
        130                 135                 140

Ile Thr Ser Val Asp Asp Phe Leu Ser Val Ser Glu Asn His Ile Leu
145                 150                 155                 160
```

```
Glu Asp Val Asn Lys Cys Val Ile Ala Leu Gln Glu Gly Asp Val Asp
                165                 170                 175

Thr Leu Asp Arg Thr Ala Gly Ala Ile Arg Gly Arg Ala Ala Arg Val
            180                 185                 190

Ile His Ile Ile Asn Ala Glu Met Glu Asn Tyr Glu Ala Gly Val Tyr
        195                 200                 205

Thr Glu Lys Val Leu Glu Ala Thr Lys Leu Leu Ser Glu Thr Val Met
    210                 215                 220

Pro Arg Phe Ala Glu Gln Val Glu Val Ala Ile Glu Ala Leu Ser Ala
225                 230                 235                 240

<210> SEQ ID NO 138
<211> LENGTH: 240
<212> TYPE: PRT
<213> ORGANISM: Homo sapiens
<220> FEATURE:
<223> OTHER INFORMATION: alpha-E-catenin (361-600)

<400> SEQUENCE: 138

Ser Asp Ala Leu Asn Ser Ala Ile Asp Lys Met Thr Lys Lys Thr Arg
  1               5                  10                  15

Asp Leu Arg Arg Gln Leu Arg Lys Ala Val Met Asp His Val Ser Asp
             20                  25                  30

Ser Phe Leu Glu Thr Asn Val Pro Leu Leu Val Leu Ile Glu Ala Ala
         35                  40                  45

Lys Asn Gly Asn Glu Lys Glu Val Lys Glu Tyr Ala Gln Val Phe Arg
     50                  55                  60

Glu His Ala Asn Lys Leu Ile Glu Val Ala Asn Leu Ala Cys Ser Ile
 65                  70                  75                  80

Ser Asn Asn Glu Glu Gly Val Lys Leu Val Arg Met Ser Ala Ser Gln
                 85                  90                  95

Leu Glu Ala Leu Cys Pro Gln Val Ile Asn Ala Ala Leu Ala Leu Ala
            100                 105                 110

Ala Lys Pro Gln Ser Lys Leu Ala Gln Glu Asn Met Asp Leu Phe Lys
        115                 120                 125

Glu Gln Trp Glu Lys Gln Val Arg Val Leu Thr Asp Ala Val Asp Asp
    130                 135                 140

Ile Thr Ser Ile Asp Asp Phe Leu Ala Val Ser Glu Asn His Ile Leu
145                 150                 155                 160

Glu Asp Val Asn Lys Cys Val Ile Ala Leu Gln Glu Lys Asp Val Asp
                165                 170                 175

Gly Leu Asp Arg Thr Ala Gly Ala Ile Arg Gly Arg Ala Ala Arg Val
            180                 185                 190

Ile His Val Val Thr Ser Glu Met Asp Asn Tyr Glu Pro Gly Val Tyr
        195                 200                 205

Thr Glu Lys Val Leu Glu Ala Thr Lys Leu Leu Ser Asn Thr Val Met
    210                 215                 220

Pro Arg Phe Thr Glu Gln Val Glu Ala Ala Val Glu Ala Leu Ser Ser
225                 230                 235                 240

<210> SEQ ID NO 139
<211> LENGTH: 22
<212> TYPE: DNA
<213> ORGANISM: Homo sapiens
<220> FEATURE:
<221> NAME/KEY: exon
<222> LOCATION: (1)..(12)
```

```
<220> FEATURE:
<221> NAME/KEY: intron
<222> LOCATION: (13)..(22)

<400> SEQUENCE: 139
actcgtgtga cggtgcttag aa                                                 22

<210> SEQ ID NO 140
<211> LENGTH: 22
<212> TYPE: DNA
<213> ORGANISM: Homo sapiens
<220> FEATURE:
<221> NAME/KEY: exon
<222> LOCATION: (1)..(12)
<220> FEATURE:
<221> NAME/KEY: intron
<222> LOCATION: (13)..(22)

<400> SEQUENCE: 140
gcacccggcg aggtgaggta tc                                                 22

<210> SEQ ID NO 141
<211> LENGTH: 22
<212> TYPE: DNA
<213> ORGANISM: Homo sapiens
<220> FEATURE:
<221> NAME/KEY: exon
<222> LOCATION: (1)..(12)
<220> FEATURE:
<221> NAME/KEY: intron
<222> LOCATION: (13)..(22)

<400> SEQUENCE: 141
gaattatacc aagtaagtgg ac                                                 22

<210> SEQ ID NO 142
<211> LENGTH: 23
<212> TYPE: DNA
<213> ORGANISM: Homo sapiens
<220> FEATURE:
<223> OTHER INFORMATION: exon 1-13; intron 14-23

<400> SEQUENCE: 142
tctcgttatt caggtcagtg tat                                                23

<210> SEQ ID NO 143
<211> LENGTH: 23
<212> TYPE: DNA
<213> ORGANISM: Homo sapiens
<220> FEATURE:
<223> OTHER INFORMATION: exon 1-13; intron 14-23

<400> SEQUENCE: 143
tttgacaaca aggtatatc taa                                                 23

<210> SEQ ID NO 144
<211> LENGTH: 24
<212> TYPE: DNA
<213> ORGANISM: Homo sapiens
<220> FEATURE:
<223> OTHER INFORMATION: exon 1-14; intron 15-24

<400> SEQUENCE: 144
tgccttttct acaggttggg ggaa                                               24

<210> SEQ ID NO 145
<211> LENGTH: 26
```

```
<212> TYPE: DNA
<213> ORGANISM: Homo sapiens
<220> FEATURE:
<223> OTHER INFORMATION: intron 1-14; exon 15-26

<400> SEQUENCE: 145
tctttctttt ttagacagag tttcag                                              26

<210> SEQ ID NO 146
<211> LENGTH: 26
<212> TYPE: DNA
<213> ORGANISM: Homo sapiens
<220> FEATURE:
<223> OTHER INFORMATION: intron 1-14; exon 15-26

<400> SEQUENCE: 146
tgttttactt acaggcattt tttact                                              26

<210> SEQ ID NO 147
<211> LENGTH: 28
<212> TYPE: DNA
<213> ORGANISM: Homo sapiens
<220> FEATURE:
<223> OTHER INFORMATION: intron 1-14; exon 15-28

<400> SEQUENCE: 147
aactcgtttt ttagattgaa aagatatg                                            28

<210> SEQ ID NO 148
<211> LENGTH: 26
<212> TYPE: DNA
<213> ORGANISM: Homo sapiens
<220> FEATURE:
<223> OTHER INFORMATION: intron 1-14; exon 15-26

<400> SEQUENCE: 148
cattttatgt tcagattcct ctggaa                                              26

<210> SEQ ID NO 149
<211> LENGTH: 26
<212> TYPE: DNA
<213> ORGANISM: Homo sapiens
<220> FEATURE:
<223> OTHER INFORMATION: intron 1-14; exon 15-26

<400> SEQUENCE: 149 aaatccctttt ttagatgatg attctg                                             26

<210> SEQ ID NO 150
<211> LENGTH: 25
<212> TYPE: DNA
<213> ORGANISM: Homo sapiens
<220> FEATURE:
<223> OTHER INFORMATION: intron 1-14; exon 15-25

<400> SEQUENCE: 150
gttttattct tcagaaaaat ctgct                                               25

<210> SEQ ID NO 151
<211> LENGTH: 7
<212> TYPE: PRT
<213> ORGANISM: Artificial sequence
<220> FEATURE:
<223> OTHER INFORMATION: Description of Artificial Sequence: nuclear
      localization signal

<400> SEQUENCE: 151
```

```
Pro Lys Lys Arg Lys Arg Lys
  1               5
```

<210> SEQ ID NO 152
<211> LENGTH: 29
<212> TYPE: DNA
<213> ORGANISM: Artificial sequence
<220> FEATURE:
<223> OTHER INFORMATION: Description of Artificial Sequence: primer
      FVR1046R

<400> SEQUENCE: 152
ccgctcgaga agttaaagag aataatcaa                                      29

<210> SEQ ID NO 153
<211> LENGTH: 25
<212> TYPE: DNA
<213> ORGANISM: Artificial sequence
<220> FEATURE:
<223> OTHER INFORMATION: Description of Artificial Sequence: primer FVR
      415

<400> SEQUENCE: 153
tcccagatat gtgtcgtaac aatcg                                          25

<210> SEQ ID NO 154
<211> LENGTH: 20
<212> TYPE: DNA
<213> ORGANISM: Artificial sequence
<220> FEATURE:
<223> OTHER INFORMATION: Description of Artificial Sequence: primer FVR
      416

<400> SEQUENCE: 154
ggccagtcac ctgaaatgtc                                                20

<210> SEQ ID NO 155
<211> LENGTH: 30
<212> TYPE: DNA
<213> ORGANISM: Artificial sequence
<220> FEATURE:
<223> OTHER INFORMATION: Description of Artificial Sequence: primer
      FVR711

<400> SEQUENCE: 155 aggggggcagt ggctgaagaa agaagatatc                                    30

<210> SEQ ID NO 156
<211> LENGTH: 29
<212> TYPE: DNA
<213> ORGANISM: Artificial sequence
<220> FEATURE:
<223> OTHER INFORMATION: Description of Artificial Sequence: primer
      FVR725

<400> SEQUENCE: 156
tattagatat cgcctctccc ggacccgcc                                      29

<210> SEQ ID NO 157
<211> LENGTH: 5
<212> TYPE: PRT
<213> ORGANISM: Artificial sequence
<220> FEATURE:
<223> OTHER INFORMATION: Description of Artificial Sequence: positive
      control fragment of protein for primers FVR1986F and FVR1987R

<400> SEQUENCE: 157

-continued

```
Gly Ala Pro Asp His
  1               5

<210> SEQ ID NO 158
<211> LENGTH: 15
<212> TYPE: PRT
<213> ORGANISM: Homo sapiens
<220> FEATURE:
<223> OTHER INFORMATION: residues 73-87 of ANC_2H01 protein

<400> SEQUENCE: 158

Asp Gly Ile Lys Ala Arg Asn Arg Asn Gln Asn Tyr Leu Val Pro
  1               5                  10                  15
```